(12) United States Patent
Rosbash et al.

(10) Patent No.: US 11,946,082 B2
(45) Date of Patent: Apr. 2, 2024

(54) COMPOSITIONS AND METHODS FOR IDENTIFYING RNA BINDING POLYPEPTIDE TARGETS

(71) Applicant: Brandeis University, Waltham, MA (US)

(72) Inventors: Michael Rosbash, Waltham, MA (US); Aoife McMahon, Waltham, MA (US); Weijin Xu, Waltham, MA (US); Hua Jin, Waltham, MA (US)

(73) Assignee: Brandeis University, Waltham, MA (US)

( * ) Notice: Subject to any disclaimer, the term of this patent is extended or adjusted under 35 U.S.C. 154(b) by 0 days.

(21) Appl. No.: 17/743,859

(22) Filed: May 13, 2022

(65) Prior Publication Data

US 2023/0045462 A1 Feb. 9, 2023

Related U.S. Application Data

(63) Continuation of application No. 16/317,749, filed as application No. PCT/US2016/054525 on Sep. 29, 2016, now Pat. No. 11,401,514.

(60) Provisional application No. 62/364,170, filed on Jul. 19, 2016.

(51) Int. Cl.
| | | |
|---|---|---|
| *C12N 9/78* | (2006.01) | |
| *C07K 14/47* | (2006.01) | |
| *C12N 7/00* | (2006.01) | |
| *C12N 15/86* | (2006.01) | |

(52) U.S. Cl.
CPC ............... *C12N 9/78* (2013.01); *C07K 14/47* (2013.01); *C12N 7/00* (2013.01); *C12N 15/86* (2013.01); *C12Y 305/04004* (2013.01); *C12Y 305/04005* (2013.01); *C07K 2319/20* (2013.01); *C07K 2319/85* (2013.01); *C12N 2750/14122* (2013.01)

(58) Field of Classification Search
None
See application file for complete search history.

(56) References Cited

U.S. PATENT DOCUMENTS

| | | |
|---|---|---|
| 2011/0223687 A1 | 9/2011 | Nakamura et al. |
| 2019/0390186 A1 | 12/2019 | Rosbash et al. |

FOREIGN PATENT DOCUMENTS

| | | |
|---|---|---|
| JP | 2010501200 A | 1/2010 |
| JP | 2011039069 A | 2/2011 |
| JP | 2013074866 A | 9/2011 |
| JP | 2016108249 A | 6/2016 |
| WO | 2008024499 A2 | 2/2008 |
| WO | 2010132092 A1 | 11/2010 |

OTHER PUBLICATIONS

Bhardwaj, A. et al.; "Characterizing TDP-43 interaction with its RNA targets"; Nucleic Acids Research, vol. 41, Issue No. 9; 2013; pp. 5062-5074.
European Search Report for European Application 16909733.4; Filing Date: Feb. 2, 2019; dated Mar. 1, 2020; 7 pages.
International Search Report and Written Opinion for International Application PCT/US2016/054525; International Filing Date: Sep. 29, 2016; dated Mar. 10, 2017; 13 pages.
Kuttan, A. et al.; "Mechanistic insights into editing—site specificity of ADARs"; PNAS, vol. 109, Issue No. 48; 2012; pp. E3295-E3304; doi: 10.1073/pnas.1212548109.
Liu, Y. et al.; "Chimeric double-stranded RNA-specific adenosine deaminase ADAR1 proteins reveal functional selectivity of double-stranded RNA-binding domains from ADAR1 and protein kinase PLR"; PNAS, vol. 97, Issue No. 23; 2000; pp. 12541-12546; doi: 10.1073/pnas.97.23.12541.
MacMahon, A. et al.; "TRIBE: Hijacking an RNA-Editing Enzyme to Identify Cell-Specific Targets of RNA-Binding Proteins"; Cell, vol. 165, Issue No. 3; 2016; pp. 742-753.
Montiel-Gonzalez, M. et al.; "Correction of mutations within the cystic fibrosis transmembrane conductance regulator by site-directed RNA editing"; PNAS, vol. 110, Issue No. 45; 2013; pp. 18285-18290.
Southall, T. et al.; "Cell-Type-Specific Profiling of Gene Expression and Chromatin Binding without Cell Isolation: Assaying RNA Pol II Occupancy in Neural Stem Cells"; Developmental Cell, vol. 26; 2013; pp. 101-112.
Steensel, B. et al.; "Identification of in vivo DNA targets of chromatin proteins using tethered Dam methyltransferase"; Nature Biotechnology, vol. 18; 2000; pp. 424-428.
Yamashita, T. et al.; "Rescue of amyotrophic lateral sclerosis phenotype in a mouse model by intravenous AAV9-ADAR2 delivery to motor neurons"; EMBO Molecular Medicine, vol. 5, Issue No. 11; 2013; pp. 1710-1719.

*Primary Examiner* — Richard G Hutson
(74) *Attorney, Agent, or Firm* — Karen A. LeCuyer; DeWitt LLP

(57) ABSTRACT

The present invention features fusion polypeptides comprising an RNA binding polypeptide operationally linked to an RNA modifying enzyme (e.g., adenosine deaminase, cytidine deaminase), and methods of use therefore.

3 Claims, 26 Drawing Sheets

Specification includes a Sequence Listing.

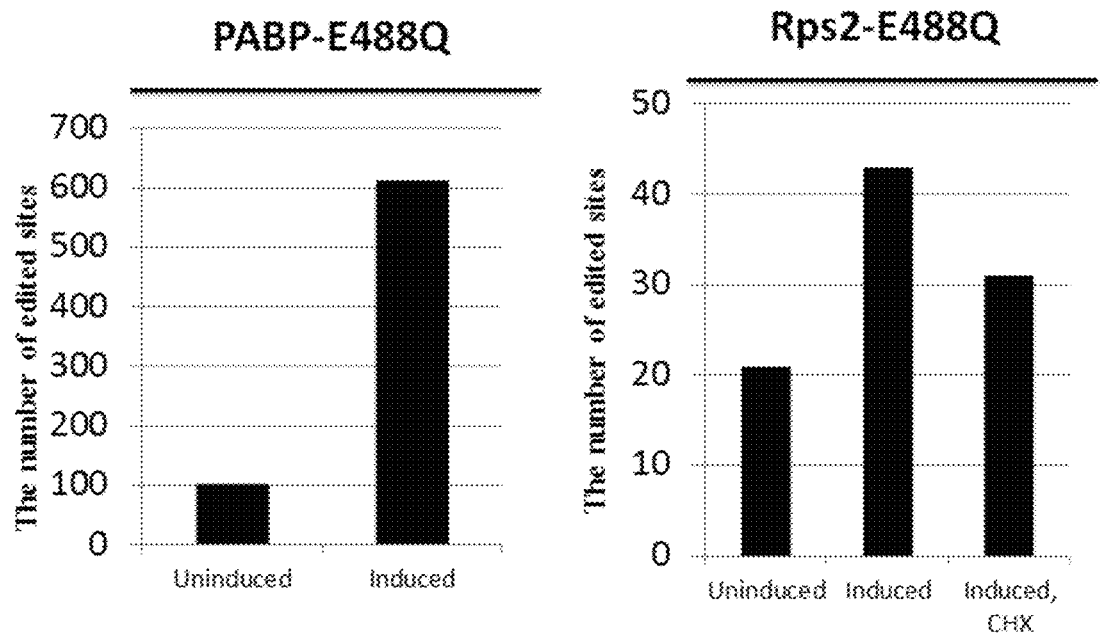

FIG. 15H

TABLE 5: GENE ONTOLOGY (GO) ANALYSIS OF COMMON TARGETS OF 4E-BP OF 4E-BP IN RAPAMYCIN AND TORIN 1 TREATMENT CONDITIONS

| Term | RT | Genes | Count | % | P-Value |
|---|---|---|---|---|---|
| Structural constituent of ribosome ← Ribosome subunit | RT | | 42 | 7.7 | 1.1E-17 |
| Structural molecule activity | RT | | 51 | 9.3 | 2.9E-8 |
| Translation factor activity, nucleic acid binding ←Translation factor | RT | | 14 | 2.6 | 1.6E-4 |
| SUMO binding | RT | | 12 | 2.2 | 2.5E-4 |
| Small conjugating protein binding | RT | | 12 | 2.2 | 2.9E-4 |
| mRNA binding | RT | | 20 | 3.7 | 1.6E-3 |
| Translation initiation factor activity ←Translation initiation factor | RT | | 10 | 1.8 | 1.7E-3 |
| Aminoacyl-tRNA ligase activity | RT | | 9 | 1.6 | 1.9E-3 |
| Ligase activity, forming carbon-oxygen bonds | RT | | 9 | 1.6 | 1.9E-3 |
| Ligase activity, forming aminoacyl-tRNA and related compounds | RT | | 9 | 1.6 | 1.9E-3 |
| Small protein activating enzyme activity | RT | | 5 | 0.9 | 2.0E-3 |
| Nucleotide binding | RT | | 80 | 14.6 | 2.3E-3 |
| ATPase activity, coupled to transmembrane movement of ions, phosphorylative mechanism | RT | | 11 | 2.0 | 3.1E-3 |
| ATPase activity, coupled to transmembrane movement of ions | RT | | 11 | 2.0 | 4.5E-3 |

FIG. 16

SEQUENCE LISTING

<160> NUMBER OF SEQ ID NOS: 57

<210> SEQ ID NO 1
<211> LENGTH: 334
<212> TYPE: PRT
<213> ORGANISM: Drosophila melanogaster

<400> SEQUENCE: 1

```
Met Asn Gly Tyr Asn Arg Lys Leu Pro Gln Lys Arg Gly Tyr Glu Met
1               5                   10                  15

Pro Lys Tyr Ser Asp Pro Lys Lys Met Cys Lys Glu Arg Ile Pro
            20                  25                  30

Gln Pro Lys Asn Thr Val Ala Met Leu Asn Glu Leu Arg His Gly Leu
            35                  40                  45

Ile Tyr Lys Leu Glu Ser Gln Thr Gly Pro Val His Ala Pro Leu Phe
    50                  55                  60

Thr Ile Ser Val Glu Val Asp Gly Gln Lys Tyr Leu Gly Gln Gly Arg
65                  70                  75                  80

Ser Lys Lys Val Ala Arg Ile Glu Ala Ala Thr Ala Leu Arg Ser
                85                  90                  95

Phe Ile Gln Phe Lys Asp Gly Ala Val Leu Ser Pro Leu Lys Pro Ala
            100                 105                 110

Gly Asn Leu Asp Phe Thr Ser Asp Glu His Leu Glu Asn Asp Val Ser
            115                 120                 125

Lys Ser Ala Ile Thr Val Asp Gly Gln Lys Lys Val Pro Asp Lys Gly
    130                 135                 140

Pro Val Met Leu Leu Tyr Glu Leu Phe Asn Asp Val Asn Phe Glu Cys
145                 150                 155                 160

Ile Asn Ile Asp Gly Ala Gln Asn Asn Cys Arg Phe Lys Met Thr Val
                165                 170                 175

Thr Ile Asn Glu Lys Lys Phe Asp Gly Thr Gly Pro Ser Lys Lys Thr
            180                 185                 190

Ala Lys Asn Ala Ala Lys Ala Ala Leu Ala Ser Leu Cys Asn Ile
    195                 200                 205

Ser Tyr Ser Pro Met Val Val Pro Gln Lys Asn Val Pro Leu Pro Ile
210                 215                 220

Asp Asp Lys Ser Ser Met Glu Leu Pro Gln Ile His Ala Asp Thr
225                 230                 235                 240

Ile Gly Arg Leu Val Leu Glu Lys Phe Met Glu Val Ile Lys Gly Gln
            245                 250                 255

Glu Ala Tyr Ser Arg Arg Lys Val Leu Ala Gly Ile Val Met Thr Glu
            260                 265                 270

Asn Met Asn Phe Cys Glu Ala Lys Val Ile Ser Val Ser Thr Gly Thr
        275                 280                 285

Lys Cys Val Ser Gly His Met Ser Val Asn Gly Ala Val Leu Asn
    290                 295                 300

Asp Ser His Ala Glu Ile Val Ser Arg Arg Cys Leu Leu Lys Tyr Leu
305                 310                 315                 320

Tyr Ala Gln Leu Asp Leu Gln Cys Asn Gln Gly Ile Val Val
            325                 330
```

<210> SEQ ID NO 2
<211> LENGTH: 1851
<212> TYPE: DNA
<213> ORGANISM: Drosophila melanogaster

<400> SEQUENCE: 2

| | | | | | |
|---|---|---|---|---|---|
| tattgtgata | actgctcaca | tcgctagatt | ccgagcaaca | aaaaagcgac | gaagggtcat | 60 |
| tgttattttt | tctaatgcaa | tgtaatgcag | caaatgtgca | gatttgaaca | agtgtaacgc | 120 |
| gatttatgtt | taatccgcat | cgaggaacca | aatcgaagta | aacgcgcggc | cagagaaaag | 180 |
| agcagcaccg | caccgaagat | aaacaaaca | agcattgatt | tgtttgtccg | gccatgtcag | 240 |
| tgtgtgtgtc | acaagggctt | gcaagtgtgt | gcgtgtgtcc | gtgcgtgtac | gtgggtgctt | 300 |
| tttttttct | cccgagtgcc | gccaagtgaa | atatgcaatt | gcacgccact | gcagttgcag | 360 |
| ccacacaaat | cctatcctaa | tcgacgaaac | agcgaagcga | ggaggctaga | atcggctgcc | 420 |
| caacgaagag | agcagaaccg | ttaacaaatg | acactctgcc | gatacagcga | agtaaaaatc | 480 |
| aataattaga | gcaaaaagcc | ggtgagtgca | ccatccgata | tcaacatgaa | tggctataac | 540 |
| cgaaaattgc | cacaaaaacg | tggctatgag | atgccaaaat | actctgatcc | aaaaaagaaa | 600 |
| atgtgcaagg | agcgcattcc | ccagccgaag | aacacggtgg | ccatgctgaa | tgagctaaga | 660 |
| catggactga | tttacaaatt | ggagtcacag | actggtccgg | tacacgcacc | tctattcacg | 720 |
| atatccgtgg | aggtcgatgg | acagaaatac | ttgggccagg | gccgtagtaa | aaaagttgca | 780 |
| cgcatcgaag | cagcagcaac | tgcactgcgc | agctttatac | agtttaagga | tggagcagtt | 840 |
| ctgtcgcctc | tgaagccggc | gggcaacttg | gactttacca | gcgatgaaca | tcttgaaaat | 900 |
| gatgtcagca | aaagtgctat | tactgttgac | ggtcagaaga | aggttccaga | taagggtcct | 960 |
| gtcatgctcc | tctacgaatt | atttaatgac | gttaatttcg | aatgcattaa | tattgacggc | 1020 |
| gcccagaaca | attgtcgctt | caaaatgacc | gtcacaatca | acgaaaagaa | gttcgatgga | 1080 |
| acaggtcctt | ccaaaaagac | ggcgaaaaat | gcggcagcta | aggcggcact | tgcttcgtta | 1140 |
| tgcaatattt | cctacagtcc | aatggtggtg | ccacagaaga | acgtacccct | gccaatcgac | 1200 |
| gacaagtcgt | catcgatgga | gttgcctcag | atacacgcgg | atacgattgg | tcggttggtc | 1260 |
| ttagaaaagt | tcatggaagt | aatcaagggc | caggaggctt | actcgcgtcg | aaaggtatta | 1320 |
| gcgggcattg | taatgactga | aaacatgaat | ttttgtgaag | ccaaagttat | ttcagtttcg | 1380 |
| acgggcacca | agtgtgtcag | cggtgagcat | atgagtgtga | acggagctgt | cctaaatgat | 1440 |
| tcccatgctg | aaatagtctc | caggcgttgt | cttctcaaat | atttatatgc | acagctggac | 1500 |
| cttcagtgca | atcagggtat | agttgtttga | tgtatatgct | aagttcagtt | tacgtatact | 1560 |
| aataatacca | tagaacttaa | atctaagagt | aatgcataat | ctagttgtta | aatgttgata | 1620 |
| tcgaaaatgt | acgctttacc | agcaagaatt | gcctacatag | aagctaaagt | tccgatttgt | 1680 |
| gctcattaac | cgtatacgag | cacaaacttt | tatttttct | ttcttttaca | cattataaac | 1740 |
| aagcacttta | agctaactta | tgttttcccc | gtctgatcgt | tttagaaggt | gtttatacaa | 1800 |
| aattaaattt | taagggcaaa | ccatcttaaa | aataaacaat | ttgtaaacat | t | 1851 |

<210> SEQ ID NO 3
<211> LENGTH: 905
<212> TYPE: PRT
<213> ORGANISM: Homo sapiens

<400> SEQUENCE: 3

```
Met Ala Glu Ile Lys Glu Lys Ile Cys Asp Tyr Leu Phe Asn Val Ser
 1               5                  10                  15

Asp Ser Ser Ala Leu Asn Leu Ala Lys Asn Ile Gly Leu Thr Lys Ala
             20                  25                  30

Arg Asp Ile Asn Ala Val Leu Ile Asp Met Glu Arg Gln Gly Asp Val
         35                  40                  45

Tyr Arg Gln Gly Thr Thr Pro Pro Ile Trp His Leu Thr Asp Lys Lys
 50                  55                  60

Arg Glu Arg Met Gln Ile Lys Arg Asn Thr Asn Ser Val Pro Glu Thr
 65                  70                  75                  80

Ala Pro Ala Ala Ile Pro Glu Thr Lys Arg Asn Ala Glu Phe Leu Thr
                 85                  90                  95

Cys Asn Ile Pro Thr Ser Asn Ala Ser Asn Asn Met Val Thr Thr Glu
             100                 105                 110

Lys Val Glu Asn Gly Gln Glu Pro Val Ile Lys Leu Glu Asn Arg Gln
         115                 120                 125

Glu Ala Arg Pro Glu Pro Ala Arg Leu Lys Pro Val His Tyr Asn
     130                 135                 140

Gly Pro Ser Lys Ala Gly Tyr Val Asp Phe Glu Asn Gly Gln Trp Ala
145                 150                 155                 160

Thr Asp Asp Ile Pro Asp Asp Leu Asn Ser Ile Arg Ala Ala Pro Gly
                 165                 170                 175

Glu Phe Arg Ala Ile Met Glu Met Pro Ser Phe Tyr Ser His Gly Leu
             180                 185                 190

Pro Arg Cys Ser Pro Tyr Lys Lys Leu Thr Glu Cys Gln Leu Lys Asn
         195                 200                 205

Pro Ile Ser Gly Leu Leu Glu Tyr Ala Gln Phe Ala Ser Gln Thr Cys
 210                 215                 220

Glu Phe Asn Met Ile Glu Gln Ser Gly Pro Pro His Glu Pro Arg Phe
225                 230                 235                 240

Lys Phe Gln Val Val Ile Asn Gly Arg Glu Phe Pro Pro Ala Glu Ala
                 245                 250                 255

Gly Ser Lys Lys Val Ala Lys Gln Asp Ala Ala Met Lys Ala Met Thr
             260                 265                 270

Ile Leu Leu Glu Glu Ala Lys Ala Lys Asp Ser Gly Lys Ser Glu Glu
         275                 280                 285

Ser Ser His Tyr Ser Thr Glu Lys Glu Ser Glu Lys Thr Ala Glu Ser
 290                 295                 300

Gln Thr Pro Thr Pro Ser Ala Thr Ser Phe Phe Ser Gly Lys Ser Pro
305                 310                 315                 320

Val Thr Thr Leu Leu Glu Cys Met His Lys Leu Gly Asn Ser Cys Glu
                 325                 330                 335

Phe Arg Leu Leu Ser Lys Glu Gly Pro Ala His Glu Pro Lys Phe Gln
             340                 345                 350

Tyr Cys Val Ala Val Gly Ala Gln Thr Phe Pro Ser Val Ser Ala Pro
         355                 360                 365

Ser Lys Lys Val Ala Lys Gln Met Ala Ala Glu Glu Ala Met Lys Ala
 370                 375                 380

Leu His Gly Glu Ala Thr Asn Ser Met Ala Asp Asn Gln Pro Glu
385                 390                 395                 400

Gly Met Ile Ser Glu Ser Leu Asp Asn Leu Glu Ser Met Met Pro Asn
                 405                 410                 415

Lys Val Arg Lys Ile Gly Glu Leu Val Arg Tyr Leu Asn Thr Asn Pro
```

-continued

```
                420             425             430
Val Gly Gly Leu Leu Glu Tyr Ala Arg Ser His Gly Phe Ala Ala Glu
            435                 440                 445

Phe Lys Leu Val Asp Gln Ser Gly Pro Pro His Glu Pro Lys Phe Val
        450                 455                 460

Tyr Gln Ala Lys Val Gly Arg Trp Phe Pro Ala Val Cys Ala His
465                 470                 475                 480

Ser Lys Lys Gln Gly Lys Gln Glu Ala Ala Asp Ala Ala Leu Arg Val
                485                 490                 495

Leu Ile Gly Glu Asn Glu Lys Ala Glu Arg Met Gly Phe Thr Glu Leu
            500                 505                 510

Pro Leu Thr Gly Ser Thr Phe His Asp Gln Ile Ala Met Leu Ser His
        515                 520                 525

Arg Cys Phe Asn Thr Leu Thr Asn Ser Phe Gln Pro Ser Leu Leu Gly
        530                 535                 540

Arg Lys Ile Leu Ala Ala Ile Ile Met Lys Lys Asp Ser Glu Asp Met
545                 550                 555                 560

Gly Val Val Ser Leu Gly Thr Gly Asn Arg Cys Val Lys Gly Asp
                565                 570                 575

Ser Leu Ser Leu Lys Gly Glu Thr Val Asn Asp Cys His Ala Glu Ile
            580                 585                 590

Ile Ser Arg Arg Gly Phe Ile Arg Phe Leu Tyr Ser Glu Leu Met Lys
        595                 600                 605

Tyr Asn Ser Gln Thr Ala Lys Asp Ser Ile Phe Glu Pro Ala Lys Gly
        610                 615                 620

Gly Glu Lys Leu Gln Ile Lys Lys Thr Val Ser Phe His Leu Tyr Ile
625                 630                 635                 640

Ser Thr Ala Pro Cys Gly Asp Gly Ala Leu Phe Asp Lys Ser Cys Ser
                645                 650                 655

Asp Arg Ala Met Glu Ser Thr Glu Ser Arg His Tyr Pro Val Phe Glu
            660                 665                 670

Asn Pro Lys Gln Gly Lys Leu Arg Thr Lys Val Glu Asn Gly Glu Gly
        675                 680                 685

Thr Ile Pro Val Glu Ser Ser Asp Ile Val Pro Thr Trp Asp Gly Ile
        690                 695                 700

Arg Leu Gly Glu Arg Leu Arg Thr Met Ser Cys Ser Asp Lys Ile Leu
705                 710                 715                 720

Arg Trp Asn Val Leu Gly Leu Gln Gly Ala Leu Leu Thr His Phe Leu
                725                 730                 735

Gln Pro Ile Tyr Leu Lys Ser Val Thr Leu Gly Tyr Leu Phe Ser Gln
            740                 745                 750

Gly His Leu Thr Arg Ala Ile Cys Cys Arg Val Thr Arg Asp Gly Ser
        755                 760                 765

Ala Phe Glu Asp Gly Leu Arg His Pro Phe Ile Val Asn His Pro Lys
        770                 775                 780

Val Gly Arg Val Ser Ile Tyr Asp Ser Lys Arg Gln Ser Gly Lys Thr
785                 790                 795                 800

Lys Glu Thr Ser Val Asn Trp Cys Leu Ala Asp Gly Tyr Asp Leu Glu
                805                 810                 815

Ile Leu Asp Gly Thr Arg Gly Thr Val Asp Gly Pro Arg Asn Glu Leu
            820                 825                 830

Ser Arg Val Ser Lys Lys Asn Ile Phe Leu Leu Phe Lys Lys Leu Cys
        835                 840                 845
```

Ser Phe Arg Tyr Arg Arg Asp Leu Leu Arg Leu Ser Tyr Gly Glu Ala
    850                 855                 860

Lys Lys Ala Ala Arg Asp Tyr Glu Thr Ala Lys Asn Tyr Phe Lys Lys
865                 870                 875                 880

Gly Leu Lys Asp Met Gly Tyr Gly Asn Trp Ile Ser Lys Pro Gln Glu
                885                 890                 895

Glu Lys Asn Phe Tyr Leu Cys Pro Val
            900                 905

<210> SEQ ID NO 4
<211> LENGTH: 674
<212> TYPE: PRT
<213> ORGANISM: Homo sapiens

<400> SEQUENCE: 4

Met Asp Ile Glu Asp Glu Glu Asn Met Ser Ser Ser Thr Asp Val
1               5                   10                  15

Lys Glu Asn Arg Asn Leu Asp Asn Val Ser Pro Lys Asp Gly Ser Thr
                20                  25                  30

Pro Gly Pro Gly Glu Gly Ser Gln Leu Ser Asn Gly Gly Gly Gly Gly
            35                  40                  45

Pro Gly Arg Lys Arg Pro Leu Glu Glu Gly Ser Asn Gly His Ser Lys
50                  55                  60

Tyr Arg Leu Lys Lys Arg Arg Lys Thr Pro Gly Pro Val Leu Pro Lys
65                  70                  75                  80

Asn Ala Leu Met Gln Leu Asn Glu Ile Lys Pro Gly Leu Gln Tyr Thr
                85                  90                  95

Leu Leu Ser Gln Thr Gly Pro Val His Ala Pro Leu Phe Val Met Ser
            100                 105                 110

Val Glu Val Asn Gly Gln Val Phe Glu Gly Ser Gly Pro Thr Lys Lys
        115                 120                 125

Lys Ala Lys Leu His Ala Ala Glu Lys Ala Leu Arg Ser Phe Val Gln
    130                 135                 140

Phe Pro Asn Ala Ser Glu Ala His Leu Ala Met Gly Arg Thr Leu Ser
145                 150                 155                 160

Val Asn Thr Asp Phe Thr Ser Asp Gln Ala Asp Phe Pro Asp Thr Leu
                165                 170                 175

Phe Asn Gly Phe Glu Thr Pro Asp Lys Ala Glu Pro Pro Phe Tyr Val
            180                 185                 190

Gly Ser Asn Gly Asp Asp Ser Phe Ser Ser Gly Asp Leu Ser Leu
        195                 200                 205

Ser Ala Ser Pro Val Pro Ala Ser Leu Ala Gln Pro Pro Leu Pro Val
    210                 215                 220

Leu Pro Pro Phe Pro Pro Ser Gly Lys Asn Pro Val Met Ile Leu
225                 230                 235                 240

Asn Glu Leu Arg Pro Gly Leu Lys Tyr Asp Phe Leu Ser Glu Ser Gly
                245                 250                 255

Glu Ser His Ala Lys Ser Phe Val Met Ser Val Val Val Asp Gly Gln
            260                 265                 270

Phe Phe Glu Gly Ser Gly Arg Asn Lys Lys Leu Ala Lys Ala Arg Ala
        275                 280                 285

Ala Gln Ser Ala Leu Ala Ala Ile Phe Asn Leu His Leu Asp Gln Thr
    290                 295                 300

Pro Ser Arg Gln Pro Ile Pro Ser Glu Gly Leu Gln Leu His Leu Pro

```
             305                 310                 315                 320
        Gln Val Leu Ala Asp Ala Val Ser Arg Leu Val Leu Gly Lys Phe Gly
                        325                 330                 335

Asp Leu Thr Asp Asn Phe Ser Ser Pro His Ala Arg Arg Lys Val Leu
                        340                 345                 350

Ala Gly Val Val Met Thr Thr Gly Thr Asp Val Lys Asp Ala Lys Val
                        355                 360                 365

Ile Ser Val Ser Thr Gly Thr Lys Cys Ile Asn Gly Glu Tyr Met Ser
                        370                 375                 380

Asp Arg Gly Leu Ala Leu Asn Asp Cys His Ala Glu Ile Ile Ser Arg
        385                 390                 395                 400

Arg Ser Leu Leu Arg Phe Leu Tyr Thr Gln Leu Glu Leu Tyr Leu Asn
                        405                 410                 415

Asn Lys Asp Asp Gln Lys Arg Ser Ile Phe Gln Lys Ser Glu Arg Gly
                        420                 425                 430

Gly Phe Arg Leu Lys Glu Asn Val Gln Phe His Leu Tyr Ile Ser Thr
                        435                 440                 445

Ser Pro Cys Gly Asp Ala Arg Ile Phe Ser Pro His Glu Pro Ile Leu
                        450                 455                 460

Glu Glu Pro Ala Asp Arg His Pro Asn Arg Lys Ala Arg Gly Gln Leu
        465                 470                 475                 480

Arg Thr Lys Ile Glu Ser Gly Glu Gly Thr Ile Pro Val Arg Ser Asn
                        485                 490                 495

Ala Ser Ile Gln Thr Trp Asp Gly Val Leu Gln Gly Glu Arg Leu Leu
                        500                 505                 510

Thr Met Ser Cys Ser Asp Lys Ile Ala Arg Trp Asn Val Val Gly Ile
                        515                 520                 525

Gln Gly Ser Leu Leu Ser Ile Phe Val Glu Pro Ile Tyr Phe Ser Ser
                        530                 535                 540

Ile Ile Leu Gly Ser Leu Tyr His Gly Asp His Leu Ser Arg Ala Met
        545                 550                 555                 560

Tyr Gln Arg Ile Ser Asn Ile Glu Asp Leu Pro Pro Leu Tyr Thr Leu
                        565                 570                 575

Asn Lys Pro Leu Leu Ser Gly Ile Ser Asn Ala Glu Ala Arg Gln Pro
                        580                 585                 590

Gly Lys Ala Pro Asn Phe Ser Val Asn Trp Thr Val Gly Asp Ser Ala
                        595                 600                 605

Ile Glu Val Ile Asn Ala Thr Thr Gly Lys Asp Glu Leu Gly Arg Ala
        610                 615                 620

Ser Arg Leu Cys Lys His Ala Leu Tyr Cys Arg Trp Met Arg Val His
        625                 630                 635                 640

Gly Lys Val Pro Ser His Leu Leu Arg Ser Lys Ile Thr Lys Pro Asn
                        645                 650                 655

Val Tyr His Glu Ser Lys Leu Ala Ala Lys Glu Tyr Gln Ala Ala Lys
                        660                 665                 670

Val His

<210> SEQ ID NO 5
<211> LENGTH: 118
<212> TYPE: PRT
<213> ORGANISM: Homo sapiens

<400> SEQUENCE: 5

Met Ser Gly Gly Ser Ser Cys Ser Gln Thr Pro Ser Arg Ala Ile Pro
```

```
            1               5                  10                 15
         Ala Thr Arg Arg Val Val Leu Gly Asp Gly Val Gln Leu Pro Pro Gly
                        20                  25                  30

Asp Tyr Ser Thr Thr Pro Gly Gly Thr Leu Phe Ser Thr Thr Pro Gly
                        35                  40                  45

Gly Thr Arg Ile Ile Tyr Asp Arg Lys Phe Leu Met Glu Cys Arg Asn
                        50                  55                  60

Ser Pro Val Thr Lys Thr Pro Pro Arg Asp Leu Pro Thr Ile Pro Gly
          65                 70                  75                  80

Val Thr Ser Pro Ser Ser Asp Glu Pro Pro Met Glu Ala Ser Gln Ser
                        85                  90                  95

His Leu Arg Asn Ser Pro Glu Asp Lys Arg Ala Gly Gly Glu Glu Ser
                       100                 105                 110

Gln Phe Glu Met Asp Ile
                       115
```

<210> SEQ ID NO 6
<211> LENGTH: 877
<212> TYPE: DNA
<213> ORGANISM: Homo sapiens

<400> SEQUENCE: 6

```
ggggcgaggc ggagcgaggc tggaggcgcg ggagggcagc gagaggttcg cgggtgcagc        60
gcacaggaga ccatgtccgg gggcagcagc tgcagccaga ccccaagccg ggccatcccc       120
gccactcgcc gggtggtgct cggcgacggc gtgcagctcc cgcccgggga ctacagcacg       180
acccccggcg gcacgctctt cagcaccacc ccggaggta ccaggatcat ctatgaccgg        240
aaattcctga tggagtgtcg gaactcacct gtgaccaaaa caccccccaag ggatctgccc      300
accattccgg gggtcaccag cccttccagt gatgagcccc ccatggaagc cagccagagc       360
cacctgcgca atagcccaga agataagcgg gcgggcggtg aagagtcaca gtttgagatg       420
gacatttaaa gcaccagcca tcgtgtggag cactaccaag gggcccctca gggccttcct       480
gggaggagtc ccaccagcca ggccttatga aagtgatcat actgggcagg cgttggcgtg       540
gggtcggaca ccccagccct ttctccctca ctcagggcac ctgccccctc ctcttcgtga       600
acaccagcag atacctcctt gtgcctccac tgatgcagga gctgccaccc caaggggagt       660
gaccccctgcc agcacaccct gcagccaagg gccaggaagt ggacaagaac gaaccccttcc    720
ttccgaatga tcagcagttc cagccccctcg ctgctggggg cgcaaccacc ccttccttag      780
gttgatgtgc ttgggaaagc tccctccccc tccttcccca agagaggaaa taaaagccac       840
cttcgcccta gggccaagaa aaaaaaaaa aaaaaaa                                  877
```

<210> SEQ ID NO 7
<211> LENGTH: 632
<212> TYPE: PRT
<213> ORGANISM: Homo sapiens

<400> SEQUENCE: 7

```
         Met Glu Glu Leu Val Val Glu Val Arg Gly Ser Asn Gly Ala Phe Tyr
          1               5                  10                  15

Lys Ala Phe Val Lys Asp Val His Glu Asp Ser Ile Thr Val Ala Phe
                        20                  25                  30

Glu Asn Asn Trp Gln Pro Asp Arg Gln Ile Pro Phe His Asp Val Arg
                        35                  40                  45

Phe Pro Pro Pro Val Gly Tyr Asn Lys Asp Ile Asn Glu Ser Asp Glu
```

```
            50                  55                  60
Val Glu Val Tyr Ser Arg Ala Asn Glu Lys Glu Pro Cys Cys Trp Trp
 65                  70                  75                  80

Leu Ala Lys Val Arg Met Ile Lys Gly Glu Phe Tyr Val Ile Glu Tyr
                 85                  90                  95

Ala Ala Cys Asp Ala Thr Tyr Asn Glu Ile Val Thr Ile Glu Arg Leu
                100                 105                 110

Arg Ser Val Asn Pro Asn Lys Pro Ala Thr Lys Asp Thr Phe His Lys
                115                 120                 125

Ile Lys Leu Asp Val Pro Glu Asp Leu Arg Gln Met Cys Ala Lys Glu
                130                 135                 140

Ala Ala His Lys Asp Phe Lys Lys Ala Val Gly Ala Phe Ser Val Thr
145                 150                 155                 160

Tyr Asp Pro Glu Asn Tyr Gln Leu Val Ile Leu Ser Ile Asn Glu Val
                165                 170                 175

Thr Ser Lys Arg Ala His Met Leu Ile Asp Met His Phe Arg Ser Leu
                180                 185                 190

Arg Thr Lys Leu Ser Leu Ile Met Arg Asn Glu Glu Ala Ser Lys Gln
                195                 200                 205

Leu Glu Ser Ser Arg Gln Leu Ala Ser Arg Phe His Glu Gln Phe Ile
210                 215                 220

Val Arg Glu Asp Leu Met Gly Leu Ala Ile Gly Thr His Gly Ala Asn
225                 230                 235                 240

Ile Gln Gln Ala Arg Lys Val Pro Gly Val Thr Ala Ile Asp Leu Asp
                245                 250                 255

Glu Asp Thr Cys Thr Phe His Ile Tyr Gly Glu Asp Gln Asp Ala Val
                260                 265                 270

Lys Lys Ala Arg Ser Phe Leu Glu Phe Ala Glu Asp Val Ile Gln Val
                275                 280                 285

Pro Arg Asn Leu Val Gly Lys Val Ile Gly Lys Asn Gly Lys Leu Ile
                290                 295                 300

Gln Glu Ile Val Asp Lys Ser Gly Val Val Arg Val Arg Ile Glu Ala
305                 310                 315                 320

Glu Asn Glu Lys Asn Val Pro Gln Glu Glu Ile Met Pro Pro Asn
                325                 330                 335

Ser Leu Pro Ser Asn Asn Ser Arg Val Gly Pro Asn Ala Pro Glu Glu
                340                 345                 350

Lys Lys His Leu Asp Ile Lys Glu Asn Ser Thr His Phe Ser Gln Pro
                355                 360                 365

Asn Ser Thr Lys Val Gln Arg Val Leu Val Ala Ser Val Val Ala
370                 375                 380

Gly Glu Ser Gln Lys Pro Glu Leu Lys Ala Trp Gln Gly Met Val Pro
385                 390                 395                 400

Phe Val Phe Val Gly Thr Lys Asp Ser Ile Ala Asn Ala Thr Val Leu
                405                 410                 415

Leu Asp Tyr His Leu Asn Tyr Leu Lys Glu Val Asp Gln Leu Arg Leu
                420                 425                 430

Glu Arg Leu Gln Ile Asp Glu Gln Leu Arg Gln Ile Gly Ala Ser Ser
                435                 440                 445

Arg Pro Pro Pro Asn Arg Thr Asp Lys Glu Lys Ser Tyr Val Thr Asp
                450                 455                 460

Asp Gly Gln Gly Met Gly Arg Gly Ser Arg Pro Tyr Arg Asn Arg Gly
465                 470                 475                 480
```

```
His Gly Arg Arg Gly Pro Gly Tyr Thr Ser Gly Thr Asn Ser Glu Ala
            485                 490                 495

Ser Asn Ala Ser Glu Thr Glu Ser Asp His Arg Asp Glu Leu Ser Asp
        500                 505                 510

Trp Ser Leu Ala Pro Thr Glu Glu Arg Glu Ser Phe Leu Arg Arg
        515                 520                 525

Gly Asp Gly Arg Arg Gly Gly Gly Arg Gly Gln Gly Gly Arg
        530                 535                 540

Gly Arg Gly Gly Phe Lys Gly Asn Asp Asp His Ser Arg Thr Asp
545                 550                 555                 560

Asn Arg Pro Arg Asn Pro Arg Glu Ala Lys Gly Arg Thr Thr Asp Gly
                565                 570                 575

Ser Leu Gln Ile Arg Val Asp Cys Asn Asn Glu Arg Ser Val His Thr
            580                 585                 590

Lys Thr Leu Gln Asn Thr Ser Ser Glu Gly Ser Arg Leu Arg Thr Gly
            595                 600                 605

Lys Asp Arg Asn Gln Lys Lys Glu Lys Pro Asp Ser Val Asp Gly Gln
        610                 615                 620

Gln Pro Leu Val Asn Gly Val Pro
625                 630

<210> SEQ ID NO 8
<211> LENGTH: 4828
<212> TYPE: DNA
<213> ORGANISM: Homo sapiens

<400> SEQUENCE: 8
actttgaagt ggtcatcaaa gagatcagtt agaagaactg atctgcagtg tgtgacagac      60
caggaaagtg atatccagag gattgccacc atgaagttgt cattttttagt ggagaggaag    120 caggagacca gaaagtgacc aaggatctgt ccatttagtt ccaggagata tgactgccag    180
agtggtatcc ttagtgggct gaatgttcag tggtcttact ttagtgacca agcaacaaga    240
cagtagggca tggtcagtaa cttttcagtca atttttgctt actaggataa agcaaaaata    300
agcttataca tttttagata cattttttgt aacttgctga gtacccaagg aaagtgtgct    360
tgtatttatg ggcgtctatt ttcagagcac taattattgc tgaattagaa cagaaatata    420
ggaaaactga tttttacaag gagcttcaaa gcaatctcag gtagtttctg attatgtatc    480
tctgcctacc tcggggtaca tagacagggt tacaatttgg ttgaggatat atgacatgtg    540
gtttttaaag acacctaggg gcattttaag aaaatttcct cgatatctga aaatctgtag    600
atttcaaaat tatgttaatc atgaaatatt ctgtgttgta attttttgtgt aggtgtattc    660 cagagcaaat gaaaagagc cttgctgttg gtggttagct aaagtgagga tgataaaggg    720
tgaggtagga aaatgcctat ttaaattttt ttcttatatt gtttcctttt tttaaaccca    780
ggttgtacat tcccgtgtgg atttctattt tgaagtaata tctaattttg agtaatttaa    840
ttaaaatgtt ttcactatgt gttcagtatg tttctgttgg tcataaattt tttcacatag    900
attatttatt ttaaaataac tgaatagggga gaacttctta ttcttacttt aaaaattgtg    960
attagaagtg acttttattt atttctcagt tttatgtgat agaatatgca gcatgtgatg   1020
caacttacaa tgaaattgtc acaattgaac gtctaagatc tgttaatccc aacaaacctg   1080
ccacaaaaga tactttccat aagatcaagc tggatgtgcc agaagactta cggcaaatgt   1140
gtgccaaaga ggcggcacat aaggatttta aaaaggcagt tggtgccttt tctgtaactt   1200
```

```
atgatccaga aaattatcag cttgtcattt tgtccatcaa tgaagtcacc tcaaagcgag    1260
cacatatgct gattgacatg cactttcgga gtctgcgcac taagttgtct ctgataatga    1320
gaaatgaaga agctagtaag cagctggaga gttcaaggca gcttgcctcg agatttcatg    1380
aacagtttat cgtaagagaa gatctgatgg gtctagctat tggtactcat ggtgctaata    1440
ttcagcaagc tagaaaagta cctggggtca ctgctattga tctagatgaa gatacctgca    1500
catttcatat ttatggagag gatcaggatg cagtgaaaaa agctagaagc tttctcgaat    1560
ttgctgaaga tgtaatacaa gttccaagga acttagtagg caaagtaata ggaaaaaatg    1620
gaaagctgat tcaggagatt gtggacaagt caggagttgt gagggtgagg attgaggctg    1680
aaaatgagaa aaatgttcca caagaagagg aaattatgcc accaaattcc cttccttcca    1740
ataattcaag ggttggacct aatgccccag aagaaaaaaa acatttagat ataaaggaaa    1800
acagcaccca ttttctcaa cctaacagta caaaagtcca gaggggtatg gtaccatttg     1860
tttttgtggg aacaaaggac agcatcgcta atgccactgt tcttttggat tatcacctga    1920
actatttaaa ggaagtagac cagttgcgtt tggagagatt acaaattgat gagcagttgc    1980
gacagattgg agctagttct agaccaccac caaatcgtac agataaggaa aaaagctatg    2040
tgactgatga tggtcaagga atgggtcgag gtagtagacc ttacagaaat aggggcacg     2100
gcagacgcgg tcctggatat acttcaggaa ctaattctga agcatcaaat gcttctgaaa    2160
cagaatctga ccacagagac gaactcagtg attggtcatt agctccaaca gaggaagaga    2220
gggagagctt cctgcgcaga ggagacggac ggcggcgtgg aggggagga agaggacaag      2280
gaggaagagg acgtggagga ggcttcaaag gaaacgacga tcactcccga acagataatc    2340
gtccacgtaa tccaagagag gctaaaggaa gaacaacaga tggatcccctt cagatcagag   2400
ttgactgcaa taatgaaagg agtgtccaca ctaaaacatt acagaatacc tccagtgaag    2460
gtagtcggct gcgcacgggt aaagatcgta accagaagaa agagaagcca gacagcgtgg    2520
atggtcagca accactcgtg aatggagtac cctaaactgc ataattctga agttatatt    2580
cctataccat ttccgtaatt cttattccat attagaaaac tttgttaggc caaagacaaa    2640
tagtaggcaa gatggcacag gcatgaaat gaacacaaat tatgctaaga attttttatt     2700
ttttggtatt ggccataagc aacaattttc agattgcac aaaaagatac cttaaaattt     2760
gaaacattgc ttttaaaact acttagcact tcagggcaga ttttagtttt atttctaaa     2820
gtactgagca gtgatattct tgttaatttt ggaccatttt cctgcattgg gtgatcattc    2880
accagtacat tctcagtttt tcttaatata tagcatttat ggtaatcata ttagacttct    2940
gttttcaatc tcgtatagaa gtcttcatga aatgctatgt catttcatgt cctgtgtcag    3000
tttatgtttt ggtccacttt tccagtattt tagtggaccc tgaaatgtgt gtgatgtgac    3060
atttgtcatt tcattagca aaaaaagttg tatgatctgt gccttttta tcttggca        3120
ggtaggaata ttatatttgg atgcagagtt cagggaagat aagttggaaa cactaaatgt    3180
taaagatgta gcaaaccctg tcaaacatta gtactttata gaaagaatgca tgctttccat   3240
attttttcc ttacataaac atcaggttag gcagtataaa gaataggact tgttttgtt      3300
tttgttttgt tgcactgaag tttgataaat agtgttattg agagagatgt gtaattttc     3360
tgtatagaca ggagaagaaa gaactatctt catctgagag aggctaaaat gttttcagct    3420
aggaacaaat cttcctggtc gaaagttagt aggatatgcc tgctctttgg cctgatgacc    3480
aattttaact tagagctttt tttttttaat tttgtctgcc ccaagttttg tgaaattttt    3540
catatttaa tttcaagctt attttggaga gataggaagg tcatttccat gtatgcataa     3600
```

```
taatcctgca aagtacaggt actttgtcta agaaacattg gaagcaggtt aaatgttttg    3660
taaactttga atatatggt ctaatgttta agcagaattg gaaaagacta agatcggtta    3720
acaaataaca acttttttt cttttttct tttgttttt gaagtgttgg ggtttggttt    3780
tgttttttga gtcttttttt ttaagtgaaa tttattgagg aaaaatatgt gaaggacctt    3840
cactctaaga tgttatattt ttcttaaaaa gtaactccta gtaggggtac cactgaatct    3900
gtacagagcc gtaaaaactg aagttctgcc tctgatgtat tttgtgagtt tgtttctttg    3960
aattttcatt ttacagttac ttttccttgc atacaaacaa gcatataaaa tggcaacaaa    4020
ctgcacatga tttcacaaat attaaaaagt cttttaaaaa gtattgccaa acattaatgt    4080
tgatttctag ttatttattc tgggaatgta tagtattgaa aacagaaatt ggtaccttgc    4140
acacatcatc tgtaagctgt ttggttttaa aatactgtag ataattaacc aaggtagaat    4200
gaccttgtaa tgtaactgct cttgggcaat attctctgta catattagcg acaacagatt    4260
ggattttatg ttgacatttg tttggttata gtgcaatata ttttgtatgc aagcagtttc    4320
aataaagttt gatcttcctc tgctaaattg atgttgatgc aatccttaca aatgattgct    4380
tttaaaattt taagctagga aaagaaatct atagaaagtg ttctgttaca aaatgtaact    4440
gttaccattg gaaatttcac gtcataggaa gttagccttt atctaccaac tttcaagaac    4500
ttgtttaata aagcgaaaaa ctcaaccaaa tggtacaaaa ccacagtgta ccattaaaat    4560
atgcactaag tctcttttt acaaaggctg tattcagcaa ggcgctaact tgcttaaatg    4620
tgaattacta acttctaaaa ctgtactttg attcacatgt tttcaaatgg agttggagtt    4680
cattcatatt acaatatttg tgtgctaaac gtgtatgttt ttcagttcaa agtcatgatg    4740
tttttaaaat cttattaaag tttcaaaaat ctgaagattg tttatctaga tgtaaatttt    4800
tattaaaaag ttgcacttat gaaaaagc                                       4828
```

<210> SEQ ID NO 9
<211> LENGTH: 526
<212> TYPE: PRT
<213> ORGANISM: Homo sapiens

<400> SEQUENCE: 9

```
Met Ala Ser Asn Asp Tyr Thr Gln Gln Ala Thr Gln Ser Tyr Gly Ala
1               5                   10                  15

Tyr Pro Thr Gln Pro Gly Gln Gly Tyr Ser Gln Gln Ser Ser Gln Pro
            20                  25                  30

Tyr Gly Gln Gln Ser Tyr Ser Gly Tyr Ser Gln Ser Thr Asp Thr Ser
        35                  40                  45

Gly Tyr Gly Gln Ser Ser Tyr Ser Ser Tyr Gly Gln Ser Gln Asn Thr
    50                  55                  60

Gly Tyr Gly Thr Gln Ser Thr Pro Gln Gly Tyr Gly Ser Thr Gly Gly
65                  70                  75                  80

Tyr Gly Ser Ser Gln Ser Ser Gln Ser Ser Tyr Gly Gln Gln Ser Ser
                85                  90                  95

Tyr Pro Gly Tyr Gly Gln Gln Pro Ala Pro Ser Ser Thr Ser Gly Ser
            100                 105                 110

Tyr Gly Ser Ser Ser Gln Ser Ser Ser Tyr Gly Gln Pro Gln Ser Gly
        115                 120                 125

Ser Tyr Ser Gln Gln Pro Ser Tyr Gly Gly Gln Gln Ser Tyr Gly
    130                 135                 140

Gln Gln Gln Ser Tyr Asn Pro Pro Gln Gly Tyr Gly Gln Gln Asn Gln
```

-continued

| | | | 145 | | | | 150 | | | | 155 | | | | 160 |
|---|---|---|---|---|---|---|---|---|---|---|---|---|---|---|---|
|Tyr|Asn|Ser|Ser|Ser|Gly|Gly|Gly|Gly|Gly|Gly|Gly|Gly|Gly|Gly|Asn|
| | | | | | 165 | | | | 170 | | | | 175 | | |

Tyr Gly Gln Asp Gln Ser Ser Met Ser Gly Gly Ser Gly Gly
            180              185            190

Gly Tyr Gly Asn Gln Asp Gln Ser Gly Gly Gly Ser Gly Gly Tyr
        195            200            205

Gly Gln Gln Asp Arg Gly Gly Arg Gly Arg Gly Ser Gly Gly Gly
210                215            220

Gly Gly Gly Gly Gly Gly Tyr Asn Arg Ser Ser Gly Gly Tyr Glu
225            230              235            240

Pro Arg Gly Arg Gly Gly Arg Gly Arg Gly Gly Met Gly Gly
            245              250            255

Ser Asp Arg Gly Gly Phe Asn Lys Phe Gly Gly Pro Arg Asp Gln Gly
        260            265            270

Ser Arg His Asp Ser Glu Gln Asp Asn Ser Asp Asn Asn Thr Ile Phe
        275            280            285

Val Gln Gly Leu Gly Glu Asn Val Thr Ile Glu Ser Val Ala Asp Tyr
    290            295            300

Phe Lys Gln Ile Gly Ile Ile Lys Thr Asn Lys Lys Thr Gly Gln Pro
305              310            315            320

Met Ile Asn Leu Tyr Thr Asp Arg Glu Thr Gly Lys Leu Lys Gly Glu
        325            330            335

Ala Thr Val Ser Phe Asp Asp Pro Pro Ser Ala Lys Ala Ala Ile Asp
            340            345            350

Trp Phe Asp Gly Lys Glu Phe Ser Gly Asn Pro Ile Lys Val Ser Phe
        355            360            365

Ala Thr Arg Arg Ala Asp Phe Asn Arg Gly Gly Gly Asn Gly Arg Gly
    370            375            380

Gly Arg Gly Arg Gly Gly Pro Met Gly Arg Gly Gly Tyr Gly Gly Gly
385              390            395            400

Gly Ser Gly Gly Gly Gly Arg Gly Gly Phe Pro Ser Gly Gly Gly Gly
            405            410            415

Gly Gly Gly Gln Gln Arg Ala Gly Asp Trp Lys Cys Pro Asn Pro Thr
            420            425            430

Cys Glu Asn Met Asn Phe Ser Trp Arg Asn Glu Cys Asn Gln Cys Lys
        435            440            445

Ala Pro Lys Pro Asp Gly Pro Gly Gly Pro Gly Gly Ser His Met
    450            455            460

Gly Gly Asn Tyr Gly Asp Asp Arg Arg Gly Gly Arg Gly Gly Tyr Asp
465              470            475            480

Arg Gly Gly Tyr Arg Gly Arg Gly Gly Asp Arg Gly Gly Phe Arg Gly
            485            490            495

Gly Arg Gly Gly Gly Asp Arg Gly Gly Phe Gly Pro Gly Lys Met Asp
            500            505            510

Ser Arg Gly Glu His Arg Gln Asp Arg Arg Glu Arg Pro Tyr
        515            520            525

<210> SEQ ID NO 10
<211> LENGTH: 5119
<212> TYPE: DNA
<213> ORGANISM: Homo sapiens

<400> SEQUENCE: 10

```
acttaagctt cgacgcagga ggcggggctg ctcagtcctc caggcgtcgg tactcagcgg      60
tgttggaact tcgttgcttg cttgcctgtg cgcgcgtgcg cggacatggc ctcaaacgat     120
tatacccaac aagcaaccca aagctatggg gcctacccca cccagcccgg gcagggctat     180
tcccagcaga gcagtcagcc ctacggacag cagagttaca gtggttatag ccagtccacg     240
gacacttcag gctatggcca gagcagctat tcttcttatg ccagagccga gaacacaggc     300
tatgaactc agtcaactcc ccagggatat ggctcgactg cgggctatgg cagtagccag      360
agctcccaat cgtcttacgg gcagcagtcc tcctaccctg gctatggcca gcagccagct     420
cccagcagca cctcgggaag ttacggtagc agttctcaga gcagcagcta tgggcagccc     480
cagagtggga gctacagcca gcagcctagc tatggtggac agcagcaaag ctatggacag     540
cagcaaagct ataatccccc tcagggctat ggacagcaga accagtacaa cagcagcagt     600
ggtggtggag gtggaggtgg aggtggaggt aactatggcc aagatcaatc ctccatgagt     660
agtggtggtg gcagtggtgg cggttatggc aatcaagacc agagtggtgg aggtggcagc     720
ggtggctatg gacagcagga ccgtgaggc cgcggcaggg gtggcagtgg tggcggcggc      780
ggcggcggcg gtggtggtta caaccgcagc agtggtggct atgaacccag aggtcgtgga     840
ggtggccgtg gaggcagagg tggcatgggc ggaagtgacc gtggtggctt caataaattt     900
ggtggccctc gggaccaagg atcacgtcat gactccgaac aggataattc agacaacaac     960
accatctttg tgcaaggcct gggtgagaat gttacaattg agtctgtggc tgattacttc    1020
aagcagattg gtattattaa gacaaacaag aaaacgggac agcccatgat taatttgtac    1080
acagacaggg aaactggcaa gctgaaggga gaggcaacgg tctcttttga tgacccacct    1140
tcagctaaag cagctattga ctggtttgat ggtaaagaat tctccggaaa tcctatcaag    1200
gtctcatttg ctactcgccg ggcagacttt aatcggggtg gtggcaatgg tcgtggaggc    1260
cgagggcgag gaggacccat gggccgtgga ggctatggag gtggtggcag tggtggtggt    1320
ggccgaggag gatttcccag tggaggtggt ggcggtggag gacagcagcg agctggtgac    1380
tggaagtgtc ctaatcccac ctgtgagaat atgaacttct cttggaggaa tgaatgcaac    1440
cagtgtaagg cccctaaacc agatggccca ggagggggac caggtggctc tcacatgggg    1500
ggtaactacg gggatgatcg tcgtggtggc agaggaggct atgatcgagg cggctaccgg    1560
ggccgcggcg gggaccgtgg aggcttccga ggggccgggg gtggtgggga cagaggtggc    1620
tttggccctg gcaagatgga ttccaggggt gagcacagac aggatcgcag ggagaggccg    1680
tattaattag cctggctccc caggttctgg aacagctttt tgtcctgtac ccagtgttac    1740
cctcgttatt ttgtaacctt ccaattcctg atcacccaag ggttttttg tgtcggacta     1800
tgtaattgta actatacctc tggttcccat taaaagtgac cattttagtt aaattttgtt    1860
cctcttcccc cttttcactt tcctggaaga tcgatgtccc gatcaggaag gtagagagtt    1920
ttcctgttca gattaccctg cccagcagga actggaatac agtgttcggg gagaaggcca    1980
aatgatatcc ttgagagcag agattaaact tttctgtcat ggggaaagtt ggtgtataaa    2040
tgagaaatga agaacatggg atgtcatgag tgttggccta aatttgccca gctatgggga    2100
attttttcctt taccacattt atttgcatac tggtcttagt ttatttgcag cagtttatcc    2160
cttttttaaga actctttgat cttttggccc ttttaatggt gaggctcaaa caaactacat    2220
ttaaatgggg cagtattcag atttgaccat ggtggagagc gcttagccac tctgggtctt    2280
tcacaggaag gagagtaact gagtgctgca ggagtttgtg gagtggagtc aggatctagg    2340
aggtgagtga ctcccttcct agctgccctg gtgaacagcg cttgggtaga tacctgctat    2400
```

```
aaggagactg gtctggctgg gttactttca catcctgcct gtactcagag ggcttgaggt    2460
cattgacatt atgagatttt aggcttgatc ccttttgat tggagggtgg aaggccctcc     2520
taagggaatg ataagtgata agaggggaa ggggttgcag ccaatgagtt aaaaccttag     2580
agcagtgctc ctcagcctct taccatgtgg ttgtaaactt gcacgtacct gccaaccagt    2640
tatttagcat gcttttatt ttagttacac agagcgtaac attaacccaa gagcagaaag     2700
gttttattta cagggttttc gaacttggtt tgtaagacac tgccatcac aagcatagct     2760 tacaaatgtg ctggggaccc ctaattggga agtgctttcc tctcaaattt ttattttta    2820 tttttagaga cagagtcttg ctctgtcatc caggctggag tgcagtggcg tgatctcggc    2880
tcactgtagc ctctgcctcc tgagtttaag cgattctcct gcctcaggag aatcccagct    2940
tctgagtagc tgagactaca ggcgtgggcc accatgccca cctagttttt gcattttag    3000 tggaggtgtg gtttcactgt gttggccagg ctggtctctt aactcctgac ctcaggtgat    3060
ccacctgcct tggcctccca aagtgctgga attacaggca tgagccgctg catctggcca    3120
tcctctcaaa ttttcaagtg ttccacaagt atgttctcta ctgaagagtt gctgcatcct    3180
tgaatcttgg gtgatttgag gcacagaaac tatgactta ttttttgaga tggagttttg     3240
ctcttgttgc ccaggctgga gtgcaatggc acgttttcg gcttaccgca actgccgcct     3300
cctgggttca agcgatagct gggattacag gcatgcgcca ccatgcccag ctaatttatt    3360 tgtatttta gtagagacgg ggtttctcca tgttggtcag gctggtctcg aactcccgac     3420
ctcaggtgat gtgcacacct cagcctccca ataaaccatg acttttaaga ggaatagcag    3480
gtttacttcc cctgccagca ttggggtgct ctctaagcaa cagtaggcgg agagtggtct    3540
ggcgtattaa aaacaaagga tcgtcaagtg ggccttccca ggcattgctt tgacttagta    3600
catgtagagg atgtggcagt tctctccgtc cctgccactg ctggtttctt tgttaaatgt    3660
ttagttgaaa tggcctgata cgatatttga gtagttcact gttggtgctt tgcctagcag    3720
gattctaatc ttgctttggt tgtggtcccc tgatgccctc ctgttaggag tggaggaggt    3780
cgaagctcct tgtaagatat gattactggg accattagtg tcaagttcct gtgtccttca    3840
aatggcatat gtgattggcc ttgaccttaa aaggaaatag ggtcccaggt gactgtttag    3900
tgggtaggtc cagttggggg ggatcttcca ggagaatgga tagagacacc tagcagcaga    3960
gagaacattg gtgcctctca agccaacctc ccacctcagc ctcccaagta gctgggacta    4020
caggtgcttc ctcgctacca cacctgggta attttttttt taattacttt ttttttta     4080 agaaacaggg tttcactggg ttgcccaggc tggtcttgaa ctggcctcaa gtgacctgcc    4140
tgcctcagcc tcccaaagtg ctgggatcac aggtgtgacc cactgcgttt ggccagaata    4200
ctctattctt actgaatgat tgaaatctgt cttgaagcat taggtgtccc attttgtga     4260 gttggaattg ggacaggcta agtaggaagt gaggagggtg gggagagctg tgctgtaggt    4320
ctgtttgtcc cttccttgat gtagccttca gttagccctt tcagcttttt tccccatctt    4380
gtgccgggcc ttcctgggtt tcagtacttg gatgtagggc tgcagttatg tcagtggtgg    4440
gtagattgac caggaattaa ggtctagggt ccagcccatg tgagacttga ctcactgatc    4500
tacctttagg catgtcttcc ttccagtctc atccttttta aatttttttt ttttttttga    4560
gacggtctca ctctcaccca ggctggattg cagtggtgtg atctcgacca actgcaacct    4620
ctgcctccca cccgcaagct atctgcccac ctcagcctct ggagtagctg ggacgggact    4680
acaggcacct gccaccatga ctggctaatt tttttttgta tttttgtgg agatggggtc     4740
```

-continued

```
ttgccatgtt gctcaggctg gtctggtctc aaaactgctc tgggctcaag tgattgtccc      4800
actttggcct cccagagtgc tgggattaag gtgtgagata ctgtgtccgg ctatgaaaat      4860
tttattttta attaacttgt atatatttat ggggtacaat gtcctatttc tgtacatgta      4920
cacattgtgg aatcaaatca ggctaatata tccatcactt catatcatta gcatgaatga      4980
gaacatacaa agccactctt agaaaatttt gaaatttatg ttatttcagc ccttttatgc      5040
tggaggttgc aaatgttttg tgaataatca gaccaaaaat aaaaacaaaa aatgattgac      5100
ttcagtcatt cagtaagaa                                                   5119
```

<210> SEQ ID NO 11
<211> LENGTH: 332
<212> TYPE: PRT
<213> ORGANISM: Homo sapiens

<400> SEQUENCE: 11

```
Met Ser Glu Ala Gly Glu Glu Gln Pro Met Glu Thr Thr Gly Ala Thr
1               5                   10                  15

Glu Asn Gly His Glu Ala Val Pro Glu Gly Glu Ser Pro Ala Gly Ala
            20                  25                  30

Gly Thr Gly Ala Ala Ala Gly Ala Gly Gly Ala Thr Ala Ala Pro Pro
        35                  40                  45

Ser Gly Asn Gln Asn Gly Ala Glu Gly Asp Gln Ile Asn Ala Ser Lys
    50                  55                  60

Asn Glu Glu Asp Ala Gly Lys Met Phe Val Gly Gly Leu Ser Trp Asp
65                  70                  75                  80

Thr Ser Lys Lys Asp Leu Lys Asp Tyr Phe Thr Lys Phe Gly Glu Val
                85                  90                  95

Val Asp Cys Thr Ile Lys Met Asp Pro Asn Thr Gly Arg Ser Arg Gly
            100                 105                 110

Phe Gly Phe Ile Leu Phe Lys Asp Ala Ala Ser Val Glu Lys Val Leu
        115                 120                 125

Asp Gln Lys Glu His Arg Leu Asp Gly Arg Val Ile Asp Pro Lys Lys
    130                 135                 140

Ala Met Ala Met Lys Lys Asp Pro Val Lys Ile Phe Val Gly Gly
145                 150                 155                 160

Leu Asn Pro Glu Ala Thr Glu Glu Lys Ile Arg Glu Tyr Phe Gly Glu
                165                 170                 175

Phe Gly Glu Ile Glu Ala Ile Glu Leu Pro Met Asp Pro Lys Leu Asn
            180                 185                 190

Lys Arg Arg Gly Phe Val Phe Ile Thr Phe Lys Glu Glu Pro Val
        195                 200                 205

Lys Lys Val Leu Glu Lys Lys Phe His Thr Val Ser Gly Ser Lys Cys
    210                 215                 220

Glu Ile Lys Val Ala Gln Pro Lys Glu Val Tyr Gln Gln Gln Tyr
225                 230                 235                 240

Gly Ser Gly Gly Arg Gly Asn Arg Asn Arg Gly Asn Arg Gly Ser Gly
                245                 250                 255

Gly Gly Gly Gly Gly Gly Gln Ser Gln Ser Trp Asn Gln Gly Tyr
            260                 265                 270

Gly Asn Tyr Trp Asn Gln Gly Tyr Gly Tyr Gln Gln Gly Tyr Gly Pro
        275                 280                 285

Gly Tyr Gly Gly Tyr Asp Tyr Ser Pro Tyr Gly Tyr Tyr Gly Tyr Gly
    290                 295                 300
```

```
Pro Gly Tyr Asp Tyr Ser Gln Gly Ser Thr Asn Tyr Gly Lys Ser Gln
305                 310                 315                 320

Arg Arg Gly Gly His Gln Asn Asn Tyr Lys Pro Tyr
                325                 330

<210> SEQ ID NO 12
<211> LENGTH: 1837
<212> TYPE: DNA
<213> ORGANISM: Homo sapiens

<400> SEQUENCE: 12
aaagggcgcc acgagtcggc attgtcaggc ggcggcaccg cgcgggacgg agcttggctg      60
ttggtcggtg ggttcccgtg cggcggcggc caaggaggag gagacacagt tggagcagct     120
ccgtgggctg actggggcga ggcctcagca gcgcgagctt gagtgcggcc gagcctgcgg     180
cgccttcccc tgcgggtggg gacgagcggg ccccgcggcg tcatcggcgg cgaggagccg     240
ccgcgcctcg gcctagcatg tcggaagcgg gcgaggagca gcccatggag acgacgggcg     300
ccaccgagaa cggacatgag gccgtccccg aaggcgagtc gccggccggg gctggcacgg     360
gcgccgcggc gggggctgga ggcgcgaccg cggcgccccc gagcgggaat cagaacggcg     420
ccgagggcga ccagatcaac gccagcaaga acgaggagga cgcgggaaaa atgttcgttg     480
gtggcctgag ctgggatact agcaaaaaag atttaaaaga ctattttact aaatttggag     540
aggtcgttga ctgtacaata aaaatggatc caacactgg acggtcaaga gggtttgggt      600
ttatcctgtt caaagatgca gccagtgtgg agaaggtcct agaccagaag gagcacaggc     660
tggatggccg tgtcattgac cctaaaaagg ccatggctat gaagaaggac ccggtgaaga     720
aaatcttcgt tgggggtctg aatcctgaag ccactgagga aagatcagg gagtactttg      780 gcgagtttgg ggagattgag gccattgaat gccaatgga tccaaagttg aacaaaagac      840
gaggttttgt gtttatcacc tttaaagaag aagaacccgt gaagaaggtt ctggagaaaa     900
agttccatac tgtcagtgga agcaagtgtg agatcaaggt ggcccagccc aaagaagtct     960
atcagcagca gcagtatggc tctgggggcc gtggaaaccg caaccgaggg aaccgaggca    1020
gcggaggtgg tggtggaggt ggaggtcaga gtcagagttg gaatcagggc tacggcaact    1080
actggaacca gggctacggc taccagcagg gctacgggcc tggctatggc ggctacgact    1140
actcgcccta tggctattac ggctacggcc ccggctacga ctacagtcag ggtagtacaa    1200
actacggcaa gagccagcga cgtggtggcc atcagaataa ctacaagcca tactgaggcg    1260
gcagcaggag cgaccaactg atcgcacaca tgctttgttt ggatatggag tgaacacaat    1320
tatgtaccaa atttaacttg caaactttc tattgcctgt cccatgtgca tcttatttaa      1380
aatttccccc atgaaaatca ctctcctgtt gactatttcc agagctctag gtgtttaggc    1440
agcgtgtggt gtctgagagg ccatagcgcc atcatgggct gatttttatt accaggtccc    1500
ccagaagcag gtgggaggct ctgcttcctg ctgccgctct gcagcctgga cctgtggacc    1560
ctggttgtaa agagtaaatt gtatcttagg aaaccagtgt cacctttttt tcaccttta    1620 attttatatt atttgcgtca tacatttcct gtaacggaag tgttaatttt actgtacttt    1680
ttggtacctt ttgggaatct aatgtattgt aaggtatttt acacgtgtcc tgattttgcc    1740
acaacctgga tattgaagct atccaagctt ttgaaataaa atttaaaaac ccccaagcct    1800
gggtgagtgt gggataaaaa aaaaaaaaa aaaaaa                                1837

<210> SEQ ID NO 13
<211> LENGTH: 326
```

```
<212> TYPE: PRT
<213> ORGANISM: Homo sapiens

<400> SEQUENCE: 13

Met Ser Asn Gly Tyr Glu Asp His Met Ala Glu Asp Cys Arg Gly Asp
1               5                   10                  15

Ile Gly Arg Thr Asn Leu Ile Val Asn Tyr Leu Pro Gln Asn Met Thr
            20                  25                  30

Gln Asp Glu Leu Arg Ser Leu Phe Ser Ser Ile Gly Val Glu Ser
        35                  40                  45

Ala Lys Leu Ile Arg Asp Lys Val Ala Gly His Ser Leu Gly Tyr Gly
    50                  55                  60

Phe Val Asn Tyr Val Thr Ala Lys Asp Ala Glu Arg Ala Ile Asn Thr
65                  70                  75                  80

Leu Asn Gly Leu Arg Leu Gln Ser Lys Thr Ile Lys Val Ser Tyr Ala
                85                  90                  95

Arg Pro Ser Ser Glu Val Ile Lys Asp Ala Asn Leu Tyr Ile Ser Gly
            100                 105                 110

Leu Pro Arg Thr Met Thr Gln Lys Asp Val Glu Asp Met Phe Ser Arg
        115                 120                 125

Phe Gly Arg Ile Ile Asn Ser Arg Val Leu Val Asp Gln Thr Thr Gly
130                 135                 140

Leu Ser Arg Gly Val Ala Phe Ile Arg Phe Asp Lys Arg Ser Glu Ala
145                 150                 155                 160

Glu Glu Ala Ile Thr Ser Phe Asn Gly His Lys Pro Pro Gly Ser Ser
                165                 170                 175

Glu Pro Ile Thr Val Lys Phe Ala Ala Asn Pro Asn Gln Asn Lys Asn
            180                 185                 190

Val Ala Leu Leu Ser Gln Leu Tyr His Ser Pro Ala Arg Arg Phe Gly
        195                 200                 205

Gly Pro Val His His Gln Ala Gln Arg Phe Arg Phe Ser Pro Met Gly
210                 215                 220

Val Asp His Met Ser Gly Leu Ser Gly Val Asn Val Pro Gly Asn Ala
225                 230                 235                 240

Ser Ser Gly Trp Cys Ile Phe Ile Tyr Asn Leu Gly Gln Asp Ala Asp
                245                 250                 255

Glu Gly Ile Leu Trp Gln Met Phe Gly Pro Phe Gly Ala Val Thr Asn
            260                 265                 270

Val Lys Val Ile Arg Asp Phe Asn Thr Asn Lys Cys Lys Gly Phe Gly
        275                 280                 285

Phe Val Thr Met Thr Asn Tyr Glu Glu Ala Ala Met Ala Ile Ala Ser
290                 295                 300

Leu Asn Gly Tyr Arg Leu Gly Asp Lys Ile Leu Gln Val Ser Phe Lys
305                 310                 315                 320

Thr Asn Lys Ser His Lys
                325

<210> SEQ ID NO 14
<211> LENGTH: 6075
<212> TYPE: DNA
<213> ORGANISM: Homo sapiens

<400> SEQUENCE: 14
ggtcgtgcgc gctgaggagg agccgctgcc gccgtcgccg tcgccgccac cgccgccacc       60
gctaccgagg ccgagcggag ccgttagcgc cgcgccgccg ccgcctcccg cccgccccgg      120
```

-continued

```
agcagcccccg ggcccgcccg cccgcatcca gattttttgaa aaatacaatg tctaatggtt    180
atgaagacca catggccgaa gactgcaggg gtgacatcgg gagaacgaat ttgatcgtca    240
actacctccc tcagaacatg acccaggatg agttacgaag cctgttcagc agcattggtg    300
aagttgaatc tgcaaaactt attcgggata agtagcagg acacagcttg ggctatggct    360
ttgtgaacta cgtgaccgcg aaggatgcag agagagcgat caacacgctg aacggcttga    420
ggctccagtc aaaaaccatt aaggtgtcgt atgctcgccc gagctcagag gtgatcaaag    480
acgccaactt gtacatcagc gggctcccgc ggaccatgac ccagaaggac gtagaagaca    540
tgttctctcg gtttgggcgg atcatcaact cgcgggtcct cgtggatcag actacaggtt    600
tgtccagagg ggttgcgttt atccggtttg acaaacggtc ggaggcagaa gaggcaatta    660
ccagtttcaa tggtcataaa cccccaggtt cctctgagcc catcacagtg aagtttgcag    720
ccaaccccaa ccagaacaaa aacgtggcac tcctctcgca gctgtaccac tcgccagcgc    780
gacggttcgg aggccccgtt caccaccagg cgcagagatt caggttctcc cccatgggcg    840
tcgatcacat gagcgggctc tctggcgtca acgtgccagg aaacgcctcc tccggctggt    900
gcattttcat ctacaacctg gggcaggatg ccgacgaggg gatcctctgg cagatgtttg    960
ggccgtttgg tgccgtcacc aatgtgaaag tgatccgcga cttcaacacc aacaagtgca   1020
aagggtttgg ctttgtgacc atgacaaact atgaagaagc cgcgatggcc atagccagcc   1080
tgaacggcta ccgcctgggg gacaaaatct acaggtttc cttcaaaacc aacaagtccc   1140
acaaataact cgctcatgct tttttttgta cggaatagat aattaagagt gaaggagttg   1200
aaacttttct tgttagtgta caactcattt tgcgccaatt ttcacaagtg tttgtctttg   1260
tctgaatgag aagtgagaag gttttttatac tctgggatgc aaccgacatg ttcaaatgtt   1320
tgaaatccca caatgttaga ccaatcttaa gtttcgtaag ttatttcctt taagatatat   1380
attaaacaga aatctaagta gaactgcatt gactaaccag tccctctgga tggtggtgaa   1440
cctgaagcat gctttaacct ctaagactgt ctaacacgcg tttcattcaa tgtctccaca   1500
gactgggtag caaaaaaatc acctttagt tttagttttt aatctaaaga tgttagacag   1560
atgctgagtg tgcgttttct caaccgcttc aacattgtaa gcgatgtatg ctttggttga   1620
caggaagttc cttttccagg caggtcccgt tgccacctcc tgctcactca gtcccgggct   1680
ctgccgagtg gtcctgggaa tggcggcggg cccgtccagc gtgggccacc actggggccg   1740
ggggccacgg gctgcatgct gggcgggccc tccagagaag gacacaaacg tgtttcgtaa   1800
gcccaggcac caatgggaat ggaccaaaga gtttcaggga aactccagta tattccagag   1860
tcagatctaa gctccaggca cgcctgaaga tgtgttgcta ctctgacatc ccgagtttct   1920
gtccacacat tgcatgcaca cgcccccaca cattggatac tgttgttcac gataatttct   1980
cccgttttcc agagcattta acatagcttg gaggcgtaaa atggctctgt attttaataa   2040
cacagaaaca tttgagcatt gtatttctcg catcccttct cgtgagcgct tagacccttt   2100
tctatttag tcggattttg ttttggaatt ttgcttttgt atgaacactc agcagaaaag   2160
tacttacttc ttgccagtta tctattaacc aaaacctttg atttgtagtt ttaaagatta   2220
accctcaaag ttctcttcat aactgccttg acatttggg ttgttctgtt ctgttaattt   2280
tcttttgctt ttttgtgttt tttgtttgtt ttactttttg catttaagac cattaaattt   2340
gattttgttt tgctcgaatt ttgttttgtt tttattttta cctttttcttt cttttttggct   2400
agggaaggtg caggtggccc agcattcagg gaggagtcgt aagatcttaa gaaaccaatc   2460
```

```
cttgcctcaa gcaaaagcat ttctgaatct gtgacgcaag aatgtgcagt tacaggctgg    2520
tggcttttaa accaggagcc cggaggaagg gtgaaagaga aagcctgtga aataggcagg    2580
gccagatcac ccaaaactcc tcaggactgg gatctggcgt ttataaataa ctagtttaca    2640
gagagaatca caaacaggat aacttagtac cagcagtttt taaccttgac gtgagactaa    2700
aacgtgaccg taggctgttt tttagttatt gctctcatga gatgatggct gtatttatct    2760
gtttatttat acctatttat gtatttattt attgaagtgt gaaattgagc aataggcagg    2820
caccaccgtc cccagagcag gtcagcgtct cgagaggccc ctggacaatt gaggatgccc    2880 atccctccc cttccctga tcttttactg aggggctgtg tgcgcgatcc ttgcaaattg    2940
atgatgttgc catccgtacc caggctgtgt ctcataaaag tcggcctggt gccagagagg    3000
acctcctttc tcccacagaa tcccagatcc tcaggaaaag ccaaaaccga ggcccattgc    3060
ccggattcga cacaaaagag ggtccctgct ctgttgcccg agagcagtct gcatcctggg    3120
accagaatgc tttcctggaa aaagaagcct tcaggtttc cctgggccag catcttctga    3180
tggaaggtgg gagccaacac ccttctgatg gaaggtggga gccaacaccc ttctgatgga    3240
aggtgggagc caacaccctt ctgatggaag gtgggagcca acaccttct gatggaaggt    3300 gggagccaac accttctga tggaaggcgg gattcccgct tctgaaactc cccctggagt    3360
ctcactccca cacatgccca tagctagcat tcaacagaga actctgtctt aagcttcaac    3420
tgtgaaaatg atgacgggct gtagcacct cagcttcttt cctcgccccc ttttatctga    3480
atcctatcaa ttattctgat gctgggacag gtgagaagaa actgtgaagt atatgagcct    3540
ttgaaagttc cctgaagttt ctcagttcag gaacattctc attgtatgtg gtctccgctg    3600
tttgaacagc cttctagcta aaaaattcca aagcctttat ttgggagtct tagcttgcaa    3660
gcttgtggaa ggatttagct taacaactgt cactcctgaa aagcaatctc tgttccatca    3720
aggttctagt tgctggccct gtgtcctcaa agttcattac atcttatcaa ggcctgttg    3780 caaggggag atccctttc ttaaaaaagg ctcaacccaa aagaaaccat tcttaaaaa    3840 attttacata gatcagttgt atttctattt agcaaaaatg agtgctctgc ttttatttgg    3900
gaatttcgat gaaaaagcgt tcagagtaga taatgttcat ttatcaaaaa tctggtttgg    3960
gaaataccaa agaggctttg attgaattcc cttttgaccc gtgtgtaact tcctctggta    4020
gttagacccc aggcagctcc gaatttgtga acctgcttcc tgatgaattc tcccttgttc    4080
ccccttggct ctgccattat ttcgtttca gtgtaatttg ccaagccgca gttttctgtg    4140
ctggctgtgc ctctagtcgc agctctgtga ctgattccct cccgggtgct gagtcccctc    4200
cccggccacc atcctgcgtg aatatcctga aattcatggg cttcctcggg ggcccgcccg    4260
caggtggtgc tgggtgggtt ccgccacctt ctcctggaag gtgagccttt tcctggccaa    4320
gggcagctgc cttaacctct gagagtctgc gcttggcctt agtcctggag acccagcctc    4380
cagggactga accgtgctgc tgttgggagc caagaccggc cctttggagc cggcagccca    4440
ggggtccctg ctggatcaga gaaatagaag cacccgaaga cggttagtgg caattccttg    4500
acccggtttg cttccaaatg aaggccattt gtccaccagg cattgaaaag acatgactta    4560
cccagtccgg catcggactt gaaaaatcga aattgacatc actcagctgt tacatttcac    4620
atccgattca gcccccttt atttccatgt gcttttcgca gccttcctgt gttggatgaa    4680
agagaataag aattcagctg acaggaggcc tctatcctgt ccctccaccc caccctccac    4740
ctcaatcccc tcccatcttc cccagaccta cctcacctac taggacctga ggcagctcct    4800
tagcagagac ccctgggggtt tagctgactc tgggggtcag gggttcctgt ccccaaactt    4860
```

-continued

```
cgcaagacag ccctgaagtc acaagtgctt tcttttaagt ggcattggca attggcgtgt    4920
aatgatggca gtagaatctg aatctcggat cccaggcagg gttcacattt ccaaaccttt    4980
ttgatttccc ctgacctcta atggctggat cctattttc tacaaccttt cagtgacatc    5040
gttcaggttt ctttcttggc catttaaaaa aacaaatttt ttttttctca cttgtaagtc    5100
accgccagta cctaagttag gctaacggag actttgacag gactggattt ttcttccacc    5160
agaagagaag ccttttccgt tggtttgggg ccacctcttt gaccatgacc atgtgatgtt    5220
ccgtttacag tgacttgctt tggggagggg gaggctctct taaccgattc ccatgttgta    5280
cagtagatgg ttagaccttt tgtatattag tgtgttttaa gttattgatt tgttttatat    5340
aaaataattt attttcagg tgccatttt catttaact ttgttttac atgggtttgt        5400 tttcaataaa gtctgacact ggtgtccaaa agtcaacaat aaaatgaatc ccattgtgtt    5460
cttttgaaga tgcctatgta acttttaagc tttttaaatt attttcagaa aaaaaaaag     5520 aaaagccctt atcagttttc catcagccca ttgccttttt attttttttt tttaatcctt    5580
gtgaataaat gttctttagt gttttaggag gaaaagcaa acctagattt tgataaccca     5640
gaagacttca gattaataaa gaagctttga aagaagacca ttttcaaaa ttttagtgaa     5700 gtgtgaatat ttttgtcaa tggctttctc aaagagaatg aaactttgc accattttca      5760 gagtttttat agagatgcca aattgatata tttacatgta atggaaacat gaaaagttt     5820 tattaaacaa ttgttcatag ctgtgtagac attttaattc agtttccaaa gctctcaaaa    5880
aatcgtattt ttgaagtacg gagtgatgcg gtttggggcg tggcttacag ttccaacgac    5940
tcaattgtcc cgatactcag ttctttctac aggtatcagg ttcgtgttaa acgctgtatg    6000
ttaactatga ctggaattct gtgatatttt ggtaataaat gaagtgggat cattgcgaaa    6060
aaaaaaaaaa aaaaa                                                     6075
```

<210> SEQ ID NO 15
<211> LENGTH: 471
<212> TYPE: PRT
<213> ORGANISM: Homo sapiens

<400> SEQUENCE: 15

Met Gln Ser Asn Lys Thr Phe Asn Leu Glu Lys Gln Asn His Thr Pro
1               5                   10                  15

Arg Lys His Gln His His His Gln Gln His His Gln Gln Gln
                20                  25                  30

Gln Gln Gln Pro Pro Pro Pro Ile Pro Ala Asn Gly Gln Gln Ala
            35                  40                  45

Ser Ser Gln Asn Glu Gly Leu Thr Ile Asp Leu Lys Asn Phe Arg Lys
    50                  55                  60

Pro Gly Glu Lys Thr Phe Thr Gln Arg Ser Arg Leu Phe Val Gly Asn
65                  70                  75                  80

Leu Pro Pro Asp Ile Thr Glu Glu Met Arg Lys Leu Phe Glu Lys
                85                  90                  95

Tyr Gly Lys Ala Gly Glu Val Phe Ile His Lys Asp Lys Gly Phe Gly
                100                 105                 110

Phe Ile Arg Leu Glu Thr Arg Thr Leu Ala Glu Ile Ala Lys Val Glu
            115                 120                 125

Leu Asp Asn Met Pro Leu Arg Gly Lys Gln Leu Arg Val Arg Phe Ala
        130                 135                 140

Cys His Ser Ala Ser Leu Thr Val Arg Asn Leu Pro Gln Tyr Val Ser

```
        145                 150                 155                 160
Asn Glu Leu Leu Glu Glu Ala Phe Ser Val Phe Gly Gln Val Glu Arg
                    165                 170                 175

Ala Val Val Ile Val Asp Asp Arg Gly Arg Pro Ser Gly Lys Gly Ile
                180                 185                 190

Val Glu Phe Ser Gly Lys Pro Ala Ala Arg Lys Ala Leu Asp Arg Cys
            195                 200                 205

Ser Glu Gly Ser Phe Leu Leu Thr Thr Phe Pro Arg Pro Val Thr Val
        210                 215                 220

Glu Pro Met Asp Gln Leu Asp Asp Glu Glu Gly Leu Pro Glu Lys Leu
225                 230                 235                 240

Val Ile Lys Asn Gln Gln Phe His Lys Glu Arg Gln Pro Pro Arg
                245                 250                 255

Phe Ala Gln Pro Gly Ser Phe Glu Tyr Glu Tyr Ala Met Arg Trp Lys
            260                 265                 270

Ala Leu Ile Glu Met Glu Lys Gln Gln Gln Asp Gln Val Asp Arg Asn
        275                 280                 285

Ile Lys Glu Ala Arg Glu Lys Leu Glu Met Glu Met Glu Ala Ala Arg
    290                 295                 300

His Glu His Gln Val Met Leu Met Arg Gln Asp Leu Met Arg Arg Gln
305                 310                 315                 320

Glu Glu Leu Arg Arg Met Glu Glu Leu His Asn Gln Glu Val Gln Lys
                325                 330                 335

Arg Lys Gln Leu Glu Leu Arg Gln Glu Glu Arg Arg Arg Arg Glu
            340                 345                 350

Glu Glu Met Arg Arg Gln Gln Glu Glu Met Met Arg Arg Gln Gln Glu
        355                 360                 365

Gly Phe Lys Gly Thr Phe Pro Asp Ala Arg Glu Gln Glu Ile Arg Met
    370                 375                 380

Gly Gln Met Ala Met Gly Gly Ala Met Gly Ile Asn Asn Arg Gly Ala
385                 390                 395                 400

Met Pro Pro Ala Pro Val Pro Ala Gly Thr Pro Ala Pro Pro Gly Pro
                405                 410                 415

Ala Thr Met Met Pro Asp Gly Thr Leu Gly Leu Thr Pro Pro Thr Thr
            420                 425                 430

Glu Arg Phe Gly Gln Ala Ala Thr Met Glu Gly Ile Gly Ala Ile Gly
        435                 440                 445

Gly Thr Pro Pro Ala Phe Asn Arg Ala Ala Pro Gly Ala Glu Phe Ala
    450                 455                 460

Pro Asn Lys Arg Arg Arg Tyr
465                 470

<210> SEQ ID NO 16
<211> LENGTH: 1229
<212> TYPE: DNA
<213> ORGANISM: Homo sapiens

<400> SEQUENCE: 16
atgcagagta ataaaacttt taacttggag aagcaaaaacc atactccaag aaagcatcat      60
caacatcacc accagcagca gcaccaccag cagcaacagc agcagccgcc accaccgcca     120
atacctgcaa atgggcaaca ggccagcagc caaaatgaag gcttgactat tgacctgaag     180 aatttttagaa aaccaggaga gaagaccttc acccaacgaa gccgtctttt tgtgggaaat     240
cttcctcccg acatcactga ggaagaaatg aggaaactat ttgagaaata tggaaaggca     300
```

```
ggcgaagtct tcattcataa ggataaagga tttggcttta tccgcttgga aacccgaacc    360
ctagcggaga ttgccaaagt ggagctggac aatatgccac tccgtggaaa ccagctgctc    420
ggaaagctct ggacagatgc agtgaaggct ccttcctgct aaccacattt cctcgtcctg    480
tgactgtgga gcccatggac cagttagatg atgaagaggg acttccagag aagctggtta    540
taaaaaacca gcaatttcac aaggaacgag agcagccacc cagatttgca cagcctggct    600
cctttgagta tgaatatgcc atgcgctgga aggcactcat tgagatggag aagcagcagc    660
aggaccaagt ggaccgcaac atcaaggagg ctcgtgagaa gctggagatg agatggaag    720 ctgcacgcca tgagcaccag gtcatgctaa tgagacagga tttgatgagg cgccaagaag    780
aacttcggag gatggaagag ctgcacaacc aagaggtgca aaaacgaaag caactggagc    840
tcaggcagga ggaagagcgc aggcgccgtg aagaagagat gcggcggcag caagaagaaa    900
tgatgcggcg acagcaggaa ggattcaagg gaaccttccc tgatgcgaga gagcaggaga    960
ttcggatggg tcagatggct atgggaggtg ctatgggcat aaacaacaga ggtgccatgc   1020
cccctgctcc tgtgccagct ggtaccccag ctcctccagg acctgccact atgatgccgg   1080
atggaacttt gggattgacc ccaccaacaa ctgaacgctt tggtcaggct gctacaatgg   1140
aaggaattgg ggcaattggt ggaactcctc ctgcattcaa ccgtgcagct cctggagctg   1200
aatttgcccc aaacaaacgt cgccgatac                                     1229
```

<210> SEQ ID NO 17
<211> LENGTH: 636
<212> TYPE: PRT
<213> ORGANISM: Homo sapiens

<400> SEQUENCE: 17

```
Met Asn Pro Ser Ala Pro Ser Tyr Pro Met Ala Ser Leu Tyr Val Gly
1               5                   10                  15

Asp Leu His Pro Asp Val Thr Glu Ala Met Leu Tyr Glu Lys Phe Ser
            20                  25                  30

Pro Ala Gly Pro Ile Leu Ser Ile Arg Val Cys Arg Asp Met Ile Thr
        35                  40                  45

Arg Arg Ser Leu Gly Tyr Ala Tyr Val Asn Phe Gln Gln Pro Ala Asp
    50                  55                  60

Ala Glu Arg Ala Leu Asp Thr Met Asn Phe Asp Val Ile Lys Gly Lys
65                  70                  75                  80

Pro Val Arg Ile Met Trp Ser Gln Arg Asp Pro Ser Leu Arg Lys Ser
                85                  90                  95

Gly Val Gly Asn Ile Phe Ile Lys Asn Leu Asp Lys Ser Ile Asp Asn
            100                 105                 110

Lys Ala Leu Tyr Asp Thr Phe Ser Ala Phe Gly Asn Ile Leu Ser Cys
        115                 120                 125

Lys Val Val Cys Asp Glu Asn Gly Ser Lys Gly Tyr Gly Phe Val His
    130                 135                 140

Phe Glu Thr Gln Glu Ala Ala Glu Arg Ala Ile Glu Lys Met Asn Gly
145                 150                 155                 160

Met Leu Leu Asn Asp Arg Lys Val Phe Val Gly Arg Phe Lys Ser Arg
                165                 170                 175

Lys Glu Arg Glu Ala Glu Leu Gly Ala Arg Ala Lys Glu Phe Thr Asn
            180                 185                 190

Val Tyr Ile Lys Asn Phe Gly Glu Asp Met Asp Asp Glu Arg Leu Lys
        195                 200                 205
```

```
Asp Leu Phe Gly Lys Phe Gly Pro Ala Leu Ser Val Lys Val Met Thr
    210                 215                 220

Asp Glu Ser Gly Lys Ser Lys Gly Phe Gly Phe Val Ser Phe Glu Arg
225                 230                 235                 240

His Glu Asp Ala Gln Lys Ala Val Asp Glu Met Asn Gly Lys Glu Leu
                245                 250                 255

Asn Gly Lys Gln Ile Tyr Val Gly Arg Ala Gln Lys Val Glu Arg
            260                 265                 270

Gln Thr Glu Leu Lys Arg Lys Phe Glu Gln Met Lys Gln Asp Arg Ile
        275                 280                 285

Thr Arg Tyr Gln Gly Val Asn Leu Tyr Val Lys Asn Leu Asp Asp Gly
    290                 295                 300

Ile Asp Asp Glu Arg Leu Arg Lys Glu Phe Ser Pro Phe Gly Thr Ile
305                 310                 315                 320

Thr Ser Ala Lys Val Met Met Glu Gly Gly Arg Ser Lys Gly Phe Gly
                325                 330                 335

Phe Val Cys Phe Ser Ser Pro Glu Glu Ala Thr Lys Ala Val Thr Glu
                340                 345                 350

Met Asn Gly Arg Ile Val Ala Thr Lys Pro Leu Tyr Val Ala Leu Ala
                355                 360                 365

Gln Arg Lys Glu Glu Arg Gln Ala His Leu Thr Asn Gln Tyr Met Gln
    370                 375                 380

Arg Met Ala Ser Val Arg Ala Val Pro Asn Pro Val Ile Asn Pro Tyr
385                 390                 395                 400

Gln Pro Ala Pro Pro Ser Gly Tyr Phe Met Ala Ala Ile Pro Gln Thr
                405                 410                 415

Gln Asn Arg Ala Ala Tyr Tyr Pro Pro Ser Gln Ile Ala Gln Leu Arg
            420                 425                 430

Pro Ser Pro Arg Trp Thr Ala Gln Gly Ala Arg Pro His Pro Phe Gln
        435                 440                 445

Asn Met Pro Gly Ala Ile Arg Pro Ala Ala Pro Arg Pro Pro Phe Ser
    450                 455                 460

Thr Met Arg Pro Ala Ser Ser Gln Val Pro Arg Val Met Ser Thr Gln
465                 470                 475                 480

Arg Val Ala Asn Thr Ser Thr Gln Thr Met Gly Pro Arg Pro Ala Ala
                485                 490                 495

Ala Ala Ala Ala Ala Thr Pro Ala Val Arg Thr Val Pro Gln Tyr Lys
                500                 505                 510

Tyr Ala Ala Gly Val Arg Asn Pro Gln Gln His Leu Asn Ala Gln Pro
            515                 520                 525

Gln Val Thr Met Gln Gln Pro Ala Val His Val Gln Gly Gln Glu Pro
        530                 535                 540

Leu Thr Ala Ser Met Leu Ala Ser Ala Pro Gln Glu Gln Lys Gln
545                 550                 555                 560

Met Leu Gly Glu Arg Leu Phe Pro Leu Ile Gln Ala Met His Pro Thr
                565                 570                 575

Leu Ala Gly Lys Ile Thr Gly Met Leu Leu Glu Ile Asp Asn Ser Glu
                580                 585                 590

Leu Leu His Met Leu Glu Ser Pro Glu Ser Leu Arg Ser Lys Val Asp
            595                 600                 605

Glu Ala Val Ala Val Leu Gln Ala His Gln Ala Lys Glu Ala Ala Gln
    610                 615                 620
```

Lys Ala Val Asn Ser Ala Thr Gly Val Pro Thr Val
625                 630                 635

<210> SEQ ID NO 18
<211> LENGTH: 2869
<212> TYPE: DNA
<213> ORGANISM: Homo sapiens

<400> SEQUENCE: 18

| | | | | | |
|---|---|---|---|---|---|
| cccttctccc | cggcggttag | tgctgagagt | gcggagtgtg | tgctccgggc | tcggaacaca | 60 |
| catttattat | taaaaaatcc | aaaaaaaatc | taaaaaaatc | ttttaaaaaa | ccccaaaaaa | 120 |
| atttacaaaa | aatccgcgtc | tccccgccg | gagacttta | ttttttttct | tcctctttta | 180 |
| taaaataacc | cggtgaagca | gccgagaccg | acccgcccgc | ccgcggcccc | gcagcagctc | 240 |
| caagaaggaa | ccaagagacc | gaggccttcc | cgctgcccgg | acccgacacc | gccaccctcg | 300 |
| ctccccgccg | gcagccggca | gccagcggca | gtggatcgac | cccgttctgc | ggccgttgag | 360 |
| tagttttcaa | ttccggttga | tttttgtccc | tctgcgcttg | ctccccgctc | ccctcccccc | 420 |
| ggctccggcc | cccagccccg | gcactcgctc | tcctcctctc | acggaaaggt | cgcggcctgt | 480 |
| ggccctgcgg | gcagccgtgc | cgagatgaac | cccagtgccc | ccagctaccc | catggcctcg | 540 |
| ctctacgtgg | gggacctcca | ccccgacgtg | accgaggcga | tgctctacga | gaagttcagc | 600 |
| ccggccgggc | ccatcctctc | catccgggtc | tgcagggaca | tgatcacccg | ccgctccttg | 660 |
| ggctacgcgt | atgtgaactt | ccagcagccg | gcggacgcgg | agcgtgcttt | ggacaccatg | 720 |
| aattttgatg | ttataaaggg | caagccagta | cgcatcatgt | ggtctcagcg | tgatccatca | 780 |
| cttcgcaaaa | gtggagtagg | caacatattc | attaaaaatc | tggacaaatc | cattgataat | 840 |
| aaagcactgt | atgatacatt | ttctgctttt | ggtaacatcc | tttcatgtaa | ggtggtttgt | 900 |
| gatgaaaatg | gttccaaggg | ctatggattt | gtacactttg | agacgcagga | agcagctgaa | 960 |
| agagctattg | aaaaaatgaa | tggaatgctc | ctaaatgatc | gcaaagtatt | tgttggacga | 1020 |
| tttaagtctc | gtaaagaacg | agaagctgaa | cttggagcta | gggcaaaaga | attcaccaat | 1080 |
| gtttacatca | agaattttgg | agaagacatg | gatgatgagc | gccttaagga | tctctttggc | 1140 |
| aagtttgggc | ctgccttaag | tgtgaaagta | atgactgatg | aaagtggaaa | atccaaagga | 1200 |
| tttggatttg | taagctttga | aaggcatgaa | gatgcacaga | aagctgtgga | tgagatgaac | 1260 |
| ggaaaggagc | tcaatggaaa | acaaatttat | gttggtcgag | ctcagaaaaa | ggtggaacgg | 1320 |
| cagacggaac | ttaagcgcaa | atttgaacag | atgaaacaag | ataggatcac | cagataccag | 1380 |
| ggtgttaatc | tttatgtgaa | aaatcttgat | gatggtattg | atgatgaacg | tctccggaaa | 1440 |
| gagttttctc | catttggtac | aatcactagt | gcaaaggtta | tgatggaggg | tggtcgcagc | 1500 |
| aaagggtttg | gttttgtatg | tttctcctcc | ccagaagaag | ccactaaagc | agttacagaa | 1560 |
| atgaacggta | gaattgtggc | cacaaagcca | ttgtatgtag | ctttagctca | gcgcaaagaa | 1620 |
| gagcgccagg | ctcacctcac | taaccagtat | atgcagagaa | tggcaagtgt | acgagctgtt | 1680 |
| cccaaccctg | taatcaaccc | ctaccagcca | gcacctcctt | caggttactt | catggcagct | 1740 |
| atcccacaga | ctcagaaccg | tgctgcatac | tatcctccta | gccaaattgc | tcaactaaga | 1800 |
| ccaagtcctc | gctggactgc | tcagggtgcc | agacctcatc | cattccaaaa | tatgcccggt | 1860 |
| gctatccgcc | cagctgctcc | tagaccacca | tttagtacta | tgagaccagc | ttcttcacag | 1920 |
| gttccacgag | tcatgtcaac | acagcgtgtt | gctaacacat | caacagacaa | aatgggtcca | 1980 |
| cgtcctgcag | ctgcagccgc | tgcagctact | cctgctgtcc | gcaccgttcc | acagtataaa | 2040 |

-continued

```
tatgctgcag gagttcgcaa tcctcagcaa catcttaatg cacagccaca agttacaatg   2100
caacagcctg ctgttcatgt acaaggtcag gaacctttga ctgcttccat gttggcatct   2160
gcccctcctc aagagcaaaa gcaaatgttg ggtgaacggc tgtttcctct tattcaagcc   2220
atgcacccta ctcttgctgg taaaatcact ggcatgttgt tggagattga taattcagaa   2280
cttcttcata tgctcgagtc tccagagtca ctccgttcta aggttgatga agctgtagct   2340
gtactacaag cccaccaagc taagaggct gcccagaaag cagttaacag tgccaccggt    2400
gttccaactg tttaaaattg atcagggacc atgaaaagaa acttgtgctt caccgaagaa   2460
aaatatctaa acatcgaaaa acttaaatat tatggaaaaa aaacattgca aaatatataaa  2520 taaataaaaa aaggaaagga aactttgaac cttatgtacc gagcaaatgc caggtctagc   2580
aaacataatg ctagtcctag attacttatt gatttaaaaa caaaaaaaca caaaaaaata   2640
gtaaaatata aaaacaaatt aatgttttat agaccctggg aaaaagaatt ttcagcaaag   2700
tacaaaaatt taaagcattc ctttctttaa ttttgtaatt ctttactgtg aatagctca    2760 gaatgtcagt tctgttttaa gtaacagaat tgataactga gcaaggaaac gtaatttgga   2820
ttataaaatt cttgctttaa taaaaattcc ttaaacagtg aaaaaaaaa                2869
```

<210> SEQ ID NO 19
<211> LENGTH: 293
<212> TYPE: PRT
<213> ORGANISM: Homo sapiens

<400> SEQUENCE: 19

```
Met Ala Asp Asp Ala Gly Ala Ala Gly Gly Pro Gly Gly Pro Gly Gly
  1               5                  10                  15

Pro Gly Met Gly Asn Arg Gly Gly Phe Arg Gly Gly Phe Gly Ser Gly
                 20                  25                  30

Ile Arg Gly Arg Gly Arg Gly Arg Gly Arg Gly Arg Gly Arg Gly Arg
             35                  40                  45

Gly Ala Arg Gly Gly Lys Ala Glu Asp Lys Glu Trp Met Pro Val Thr
         50                  55                  60

Lys Leu Gly Arg Leu Val Lys Asp Met Lys Ile Lys Ser Leu Glu Glu
 65                  70                  75                  80

Ile Tyr Leu Phe Ser Leu Pro Ile Lys Glu Ser Glu Ile Ile Asp Phe
                 85                  90                  95

Phe Leu Gly Ala Ser Leu Lys Asp Glu Val Leu Lys Ile Met Pro Val
                100                 105                 110

Gln Lys Gln Thr Arg Ala Gly Gln Arg Thr Arg Phe Lys Ala Phe Val
            115                 120                 125

Ala Ile Gly Asp Tyr Asn Gly His Val Gly Leu Gly Val Lys Cys Ser
        130                 135                 140

Lys Glu Val Ala Thr Ala Ile Arg Gly Ala Ile Ile Leu Ala Lys Leu
145                 150                 155                 160

Ser Ile Val Pro Val Arg Arg Gly Tyr Trp Gly Asn Lys Ile Gly Lys
                165                 170                 175

Pro His Thr Val Pro Cys Lys Val Thr Gly Arg Cys Gly Ser Val Leu
            180                 185                 190

Val Arg Leu Ile Pro Ala Pro Arg Gly Thr Gly Ile Val Ser Ala Pro
        195                 200                 205

Val Pro Lys Lys Leu Leu Met Met Ala Gly Ile Asp Asp Cys Tyr Thr
    210                 215                 220

Ser Ala Arg Gly Cys Thr Ala Thr Leu Gly Asn Phe Ala Lys Ala Thr
```

```
                225                 230                 235                 240

Phe Asp Ala Ile Ser Lys Thr Tyr Ser Tyr Leu Thr Pro Asp Leu Trp
                        245                 250                 255

Lys Glu Thr Val Phe Thr Lys Ser Pro Tyr Gln Glu Phe Thr Asp His
                    260                 265                 270

Leu Val Lys Thr His Thr Arg Val Ser Val Gln Arg Thr Gln Ala Pro
                275                 280                 285

Ala Val Ala Thr Thr
            290

<210> SEQ ID NO 20
<211> LENGTH: 962
<212> TYPE: DNA
<213> ORGANISM: Homo sapiens

<400> SEQUENCE: 20 cttctttttcc gacaaaacac caaatggcgg atgacgccgg tgcagcgggg gggcccgggg       60
gccctggtgg ccctgggatg gggaaccgcg gtggcttccg cggagttttc ggcagtggca      120
tccggggccg gggtcgcggc cgtggacggg gccggggccg aggccgcgga gctcgcggag      180
gcaaggccga ggataaggag tggatgcccg tcaccaagtt gggccgcttg gtcaaggaca      240
tgaagatcaa gtccctggag gagatctatc tcttctccct gcctattaag aatcagaga       300 tcattgattt cttcctgggg gcctctctca aggatgaggt tttgaagatt atgccagtgc      360
agaagcagac ccgtgccggc cagcgcacca ggttcaaggc atttgttgct atcggggact      420
acaatggcca cgtcggtctg ggtgttaagt gctccaagga ggtggccacc gccatccgtg      480 ggccatcat cctggccaag ctctccatcg tccccgtgcg cagaggctac tgggggaaca      540
agatcggcaa gccccacact gtcccttgca aggtgacagg ccgctgcggc tctgtgctgg      600
tacgcctcat ccctgcaccc aggggcactg gcatcgtctc cgcacctgtg cctaagaagc      660
tgctcatgat ggctggtatc gatgactgct acacctcagc ccggggctgc actgccaccc      720
tgggcaactt cgccaaggcc acctttgatg ccatttctaa gacctacagc tacctgaccc      780
ccgacctctg gaaggagact gtattcacca gtctccccta tcaggagttc actgaccacc      840
tcgtcaagac ccacaccaga gtctccgtgc agcggactca ggctccagct gtggctacaa      900
catagggttt ttatacaaga aaataaagt gaattaagcg tgaaaaaaaa aaaaaaaaa      960 aa                                                                      962

<210> SEQ ID NO 21
<211> LENGTH: 414
<212> TYPE: PRT
<213> ORGANISM: Homo sapiens

<400> SEQUENCE: 21

Met Ser Glu Tyr Ile Arg Val Thr Glu Asp Glu Asn Asp Glu Pro Ile
1               5                   10                  15

Glu Ile Pro Ser Glu Asp Asp Gly Thr Val Leu Leu Ser Thr Val Thr
                20                  25                  30

Ala Gln Phe Pro Gly Ala Cys Gly Leu Arg Tyr Arg Asn Pro Val Ser
            35                  40                  45

Gln Cys Met Arg Gly Val Arg Leu Val Glu Gly Ile Leu His Ala Pro
        50                  55                  60

Asp Ala Gly Trp Gly Asn Leu Val Tyr Val Val Asn Tyr Pro Lys Asp
65                  70                  75                  80
```

```
Asn Lys Arg Lys Met Asp Glu Thr Asp Ala Ser Ser Ala Val Lys Val
                 85                  90                  95

Lys Arg Ala Val Gln Lys Thr Ser Asp Leu Ile Val Leu Gly Leu Pro
            100                 105                 110

Trp Lys Thr Thr Glu Gln Asp Leu Lys Glu Tyr Phe Ser Thr Phe Gly
        115                 120                 125

Glu Val Leu Met Val Gln Val Lys Lys Asp Leu Lys Thr Gly His Ser
    130                 135                 140

Lys Gly Phe Gly Phe Val Arg Phe Thr Glu Tyr Glu Thr Gln Val Lys
145                 150                 155                 160

Val Met Ser Gln Arg His Met Ile Asp Gly Arg Trp Cys Asp Cys Lys
                165                 170                 175

Leu Pro Asn Ser Lys Gln Ser Gln Asp Glu Pro Leu Arg Ser Arg Lys
            180                 185                 190

Val Phe Val Gly Arg Cys Thr Glu Asp Met Thr Glu Asp Glu Leu Arg
        195                 200                 205

Glu Phe Phe Ser Gln Tyr Gly Asp Val Met Asp Val Phe Ile Pro Lys
    210                 215                 220

Pro Phe Arg Ala Phe Ala Phe Val Thr Phe Ala Asp Asp Gln Ile Ala
225                 230                 235                 240

Gln Ser Leu Cys Gly Glu Asp Leu Ile Ile Lys Gly Ile Ser Val His
                245                 250                 255

Ile Ser Asn Ala Glu Pro Lys His Asn Ser Asn Arg Gln Leu Glu Arg
            260                 265                 270

Ser Gly Arg Phe Gly Gly Asn Pro Gly Gly Phe Gly Asn Gln Gly Gly
        275                 280                 285

Phe Gly Asn Ser Arg Gly Gly Ala Gly Leu Gly Asn Asn Gln Gly
    290                 295                 300

Ser Asn Met Gly Gly Gly Met Asn Phe Gly Ala Phe Ser Ile Asn Pro
305                 310                 315                 320

Ala Met Met Ala Ala Ala Gln Ala Ala Leu Gln Ser Ser Trp Gly Met
                325                 330                 335

Met Gly Met Leu Ala Ser Gln Gln Asn Gln Ser Gly Pro Ser Gly Asn
            340                 345                 350

Asn Gln Asn Gln Gly Asn Met Gln Arg Glu Pro Asn Gln Ala Phe Gly
        355                 360                 365

Ser Gly Asn Asn Ser Tyr Ser Gly Ser Asn Ser Gly Ala Ala Ile Gly
    370                 375                 380

Trp Gly Ser Ala Ser Asn Ala Gly Ser Gly Ser Gly Phe Asn Gly Gly
385                 390                 395                 400

Phe Gly Ser Ser Met Asp Ser Lys Ser Ser Gly Trp Gly Met
                405                 410
```

<210> SEQ ID NO 22
<211> LENGTH: 1251
<212> TYPE: DNA
<213> ORGANISM: Homo sapiens

<400> SEQUENCE: 22

| | | | | |
|---|---|---|---|---|
| atgtctgaat atattcgggt aaccgaagat gagaacgatg agcccattga ataccatcg | | | | 60 |
| gaagacgatg ggacggtgct gctctccacg gttacagccc agtttccagg ggcgtgtggg | | | | 120 |
| cttcgctaca ggaatccagt gtctcagtgt atgagaggtg tccggctggt agaaggaatt | | | | 180 |
| ctgcatgccc cagatgctgg ctggggaaat ctggtgtatg ttgtcaacta tccaaaagat | | | | 240 |

```
aacaaaagaa aaatggatga gacagatgct tcatcagcag tgaaagtgaa aagagcagtc    300
cagaaaacat ccgatttaat agtgttgggt ctcccatgga aaacaaccga acaggacctg    360
aaagagtatt ttagtaccct tggagaagtt cttatggtgc aggtcaagaa agatcttaag    420
actggtcatt caaggggtt tggctttgtt cgttttacgg aatatgaaac acaagtgaaa    480
gtaatgtcac agcgacatat gatagatgga cgatggtgtg actgcaaact tcctaattct    540
aagcaaagcc aagatgagcc tttgagaagc agaaaagtgt tgtggggcg ctgtacagag    600 gacatgactg aggatgagct gcgggagttc ttctctcagt acggggatgt gatggatgtc    660
ttcatcccca agccattcag ggcctttgcc tttgttacat ttgcagatga tcagattgcg    720
cagtctcttt gtggagagga cttgatcatt aaaggaatca gcgttcatat atccaatgcc    780
gaacctaagc acaatagcaa tagacagtta gaaagaagtg gaagatttgg tggtaatcca    840
ggtggctttg gaatcagggg tggatttggt aatagcagag ggggtggagc tggtttggga    900
aacaatcaag gtagtaatat gggtggtggg atgaactttg gtgcgttcag cattaatcca    960
gccatgatgg ctgccgccca ggcagcacta cagagcagtt ggggtatgat gggcatgtta   1020
gccagccagc agaaccagtc aggcccatcg gtaataacc aaaaccaagg caacatgcag   1080
agggagccaa accaggcctt cggttctgga ataactctt atagtggctc taattctggt   1140
gcagcaattg gttggggatc agcatccaat gcagggtcgg gcagtggttt taatggaggc   1200
tttggctcaa gcatggattc taagtcttct ggctggggaa tgaatcacta g            1251
```

<210> SEQ ID NO 23
<211> LENGTH: 577
<212> TYPE: PRT
<213> ORGANISM: Homo sapiens

<400> SEQUENCE: 23

```
Met Asn Lys Leu Tyr Ile Gly Asn Leu Asn Glu Ser Val Thr Pro Ala
1               5                   10                  15

Asp Leu Glu Lys Val Phe Ala Glu His Lys Ile Ser Tyr Ser Gly Gln
            20                  25                  30

Phe Leu Val Lys Ser Gly Tyr Ala Phe Val Asp Cys Pro Asp Glu His
        35                  40                  45

Trp Ala Met Lys Ala Ile Glu Thr Phe Ser Gly Lys Val Glu Leu Gln
    50                  55                  60

Gly Lys Arg Leu Glu Ile Glu His Ser Val Pro Lys Lys Gln Arg Ser
65                  70                  75                  80

Arg Lys Ile Gln Ile Arg Asn Ile Pro Pro Gln Leu Arg Trp Glu Val
                85                  90                  95

Leu Asp Ser Leu Leu Ala Gln Tyr Gly Thr Val Glu Asn Cys Glu Gln
            100                 105                 110

Val Asn Thr Glu Ser Glu Thr Ala Val Val Asn Val Thr Tyr Ser Asn
        115                 120                 125

Arg Glu Gln Thr Arg Gln Ala Ile Met Lys Leu Asn Gly His Gln Leu
    130                 135                 140

Glu Asn His Ala Leu Lys Val Ser Tyr Ile Pro Asp Glu Gln Ile Ala
145                 150                 155                 160

Gln Gly Pro Glu Asn Gly Arg Arg Gly Gly Phe Gly Ser Arg Gly Gln
                165                 170                 175

Pro Arg Gln Gly Ser Pro Val Ala Ala Gly Ala Pro Ala Lys Gln Gln
            180                 185                 190

Gln Val Asp Ile Pro Leu Arg Leu Leu Val Pro Thr Gln Tyr Val Gly
```

```
            195                 200                 205
Ala Ile Ile Gly Lys Glu Gly Ala Thr Ile Arg Asn Ile Thr Lys Gln
    210                 215                 220

Thr Gln Ser Lys Ile Asp Val His Arg Lys Glu Asn Ala Gly Ala Ala
225                 230                 235                 240

Glu Lys Ala Ile Ser Val His Ser Thr Pro Glu Gly Cys Ser Ser Ala
                245                 250                 255

Cys Lys Met Ile Leu Glu Ile Met His Lys Glu Ala Lys Asp Thr Lys
            260                 265                 270

Thr Ala Asp Glu Val Pro Leu Lys Ile Leu Ala His Asn Asn Phe Val
275                 280                 285

Gly Arg Leu Ile Gly Lys Glu Gly Arg Asn Leu Lys Lys Val Glu Gln
    290                 295                 300

Asp Thr Glu Thr Lys Ile Thr Ile Ser Ser Leu Gln Asp Leu Thr Leu
305                 310                 315                 320

Tyr Asn Pro Glu Arg Thr Ile Thr Val Lys Gly Ala Ile Glu Asn Cys
                325                 330                 335

Cys Arg Ala Glu Gln Glu Ile Met Lys Lys Val Arg Glu Ala Tyr Glu
            340                 345                 350

Asn Asp Val Ala Ala Met Ser Leu Gln Ser His Leu Ile Pro Gly Leu
        355                 360                 365

Asn Leu Ala Ala Val Gly Leu Phe Pro Ala Ser Ser Ala Val Pro
370                 375                 380

Pro Pro Pro Ser Ser Val Thr Gly Ala Ala Pro Tyr Ser Ser Phe Met
385                 390                 395                 400

Gln Ala Pro Glu Gln Glu Met Val Gln Val Phe Ile Pro Ala Gln Ala
                405                 410                 415

Val Gly Ala Ile Ile Gly Lys Lys Gly Gln His Ile Lys Gln Leu Ser
            420                 425                 430

Arg Phe Ala Ser Ala Ser Ile Lys Ile Ala Pro Pro Glu Thr Pro Asp
        435                 440                 445

Ser Lys Val Arg Met Val Ile Ile Thr Gly Pro Pro Glu Ala Gln Phe
    450                 455                 460

Lys Ala Gln Gly Arg Ile Tyr Gly Lys Leu Lys Glu Glu Asn Phe Phe
465                 470                 475                 480

Gly Pro Lys Glu Glu Val Lys Leu Glu Thr His Ile Arg Val Pro Ala
                485                 490                 495

Ser Ala Ala Gly Arg Val Ile Gly Lys Gly Gly Lys Thr Val Asn Glu
            500                 505                 510

Leu Gln Asn Leu Thr Ala Ala Glu Val Val Val Pro Arg Asp Gln Thr
        515                 520                 525

Pro Asp Glu Asn Asp Gln Val Ile Val Lys Ile Ile Gly His Phe Tyr
    530                 535                 540

Ala Ser Gln Met Ala Gln Arg Lys Ile Arg Asp Ile Leu Ala Gln Val
545                 550                 555                 560

Lys Gln Gln His Gln Lys Gly Gln Ser Asn Gln Ala Gln Ala Arg Arg
                565                 570                 575

Lys

<210> SEQ ID NO 24
<211> LENGTH: 2381
<212> TYPE: DNA
<213> ORGANISM: Homo sapiens
```

```
<400> SEQUENCE: 24
agaaacgtga cacaccagcc ctctcggagg ggtttcggac cgaagggaag aagctgcgcc      60
gtgtcgtccg tctccctgcg cgccgcgggc acttctcctg ggctctcccc gaactctccc     120
gcgacctctg cgcgccctca ggccgccttc cccgccctgg gctcgggaca acttctgggg     180
tggggtgcaa agaaagtttg cggctcctgc cgccggcctc tccgcctctt ggcctaggag     240
gctcgccgcc cgcgcccgct cgttcggcct tgcccgggac cgcgtcctgc ccgagaccg     300
ccaccatgaa caagctttac atcggcaacc tcaacgagag cgtgaccccc gcggacttgg     360
agaaagtgtt tgcggagcac aagatctcct acagcggcca gttcttggtc aaatccggct     420
acgccttcgt ggactgcccg gacgagcact gggcgatgaa ggccatcgaa actttctccg     480
ggaaagtaga attacaagga aaacgcttag agattgaaca ttcggtgccc aaaaaacaaa     540
ggagccggaa aattcaaatc cgaaatattc caccccagct ccgatgggaa gtactggaca     600
gcctgctggc tcagtatggt acagtagaga actgtgagca agtgaacacc gagagtgaga     660
cggcagtggt gaatgtcacc tattccaacc gggagcagac caggcaagcc atcatgaagc     720
tgaatggcca ccagttggag aaccatgccc tgaaggtctc ctacatcccc gatgagcaga     780
tagcacaggg acctgagaat gggcgccgag ggggcttggg ctctcggggt cagccccgcc     840
agggctcacc tgtggcagcg ggggcccag ccaagcagca gcaagtggac atccccttc      900
ggctcctggt gccacccag tatgtgggtg ccattattgg caaggagggg gccaccatcc     960
gcaacatcac aaaacagacc cagtccaaga tagacgtgca taggaaggag aacgcaggtg    1020
cagctgaaaa agccatcagt gtgcactcca ccccctgaggg ctgctcctcc gcttgtaaga    1080
tgatcttgga gattatgcat aaagaggcta aggacaccaa aacggctgac gaggttcccc    1140
tgaagaccct ggcccataat aactttgtag ggcgtctcat tggcaaggaa ggacggaacc    1200
tgaagaaggt agagcaagat accgagacaa aaatcaccat ctcctcgttg caagaccta    1260
cccttttacaa ccctgagagg accatcactg tgaaggggc catcgagaat tgttgcaggg    1320
ccgagcagga aataatgaag aaagttcggg aggcctatga aatgatgtg ctgccatga     1380
gcctgcagtc tcacctgacc cctggcctga acctggctgc tgtaggtctt ttcccagctt    1440
catccagcgc agtcccgccg cctcccagca gcgttactgg ggctgctccc tatagctcct    1500
ttatgcaggc tcccgagcag gagatggtgc aggtgtttat ccccgcccag gcagtgggcg    1560
ccatcatcgg caagaagggg cagcacatca acagctctc ccggtttgcc agcgcctcca    1620
tcaagattgc accacccgaa acacctgact ccaaagttcg tatggttatc atcactggac    1680
cgccagaggc ccaattcaag gctcagggaa gaatctatgg caaactcaag gaggagaact    1740
tctttggtcc caaggaggaa gtgaagctgg agacccacat acgtgtgcca gcatcagcag    1800
ctggccgggt cattggcaaa ggtggaaaaa cggtgaacga gttgcagaat ttgacggcag    1860
ctgaggtggt agtaccaaga gaccagaccc tgatgagaa cgaccaggtc atcgtgaaaa    1920
tcatcggaca tttctatgcc agtcagatgg ctcaacggaa gatccgagac atcctggccc    1980
aggttaagca gcagcatcag aagggacaga gtaaccaggc ccaggcacga aggaagtgac    2040
cagcccctcc ctgtcccttc gagtccagga caacaacggg cagaaatcga gagtgtgctc    2100
tccccggcag gcctgagaat gagtgggaat ccgggacacc tgggccgggc tgtagatcag    2160
gtttgcccac ttgattgaga aagatgttcc agtgaggaac cctgatctct cagcccccaa    2220
acacctaccc aattggccca acactgtctg cccctcgggg tgtcagaaat tctagcgcaa    2280
ggcactttta aacgtggatt gtttaaagaa gctctccagg ccccaccaag agggtggatc    2340
```

-continued

```
acacctcagt gggaagaaaa ataaaatttc cttcaggttt t                           2381
```

<210> SEQ ID NO 25
<211> LENGTH: 6
<212> TYPE: DNA
<213> ORGANISM: Drosophila melanogaster

<400> SEQUENCE: 25

```
vbyrvs                                                                  6
```

<210> SEQ ID NO 26
<211> LENGTH: 10
<212> TYPE: DNA
<213> ORGANISM: Drosophila melanogaster
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (6)..(7)
<223> OTHER INFORMATION: n is a, c, g, or t

<400> SEQUENCE: 26

```
wwnnhnndww                                                             10
```

<210> SEQ ID NO 27
<211> LENGTH: 10
<212> TYPE: DNA
<213> ORGANISM: Drosophila melanogaster
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 27

```
wwnhnhdnwd                                                             10
```

<210> SEQ ID NO 28
<211> LENGTH: 10
<212> TYPE: DNA
<213> ORGANISM: Drosophila melanogaster

<400> SEQUENCE: 28

```
tabrhatryd                                                             10
```

<210> SEQ ID NO 29
<211> LENGTH: 10
<212> TYPE: DNA
<213> ORGANISM: Drosophila melanogaster
<220> FEATURE:
<221> NAME/KEY: misc_feature
<222> LOCATION: (1)..(1)
<223> OTHER INFORMATION: n is a, c, g, or t

<400> SEQUENCE: 29

```
nayrtatgbv                                                             10
```

<210> SEQ ID NO 30

```
<211> LENGTH: 10
<212> TYPE: DNA
<213> ORGANISM: Drosophila melanogaster
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t

<400> SEQUENCE: 30 nnwhhrnnhw                                                              10

<210> SEQ ID NO 31
<211> LENGTH: 10
<212> TYPE: DNA
<213> ORGANISM: Drosophila melanogaster
<220> FEATURE:
<221> NAME/KEY: misc_feature
<222> LOCATION: (5)..(5)
<223> OTHER INFORMATION: n is a, c, g, or t

<400> SEQUENCE: 31 bdsyndvrgb                                                              10

<210> SEQ ID NO 32
<211> LENGTH: 8
<212> TYPE: DNA
<213> ORGANISM: Drosophila melanogaster

<400> SEQUENCE: 32 tgtrtgta                                                                 8

<210> SEQ ID NO 33
<211> LENGTH: 8
<212> TYPE: DNA
<213> ORGANISM: Drosophila melanogaster
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 33 gcngcngc                                                                 8

<210> SEQ ID NO 34
<211> LENGTH: 8
<212> TYPE: DNA
<213> ORGANISM: Drosophila melanogaster

<400> SEQUENCE: 34 tttdtttt                                                                 8

<210> SEQ ID NO 35
<211> LENGTH: 10
<212> TYPE: DNA
<213> ORGANISM: Drosophila melanogaster

<400> SEQUENCE: 35 tdtdtdtdtd                                                              10
```

```
<210> SEQ ID NO 36
<211> LENGTH: 10
<212> TYPE: DNA
<213> ORGANISM: Drosophila melanogaster
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t

<400> SEQUENCE: 36 ryrvasmnrn                                                            10

<210> SEQ ID NO 37
<211> LENGTH: 10
<212> TYPE: DNA
<213> ORGANISM: Drosophila melanogaster

<400> SEQUENCE: 37 rmaamvmaaa                                                            10

<210> SEQ ID NO 38
<211> LENGTH: 14
<212> TYPE: PRT
<213> ORGANISM: Homo sapiens

<400> SEQUENCE: 38

Leu Arg Thr Lys Ile Glu Ser Gly Glu Gly Thr Ile Pro Val
1               5                   10

<210> SEQ ID NO 39
<211> LENGTH: 14
<212> TYPE: PRT
<213> ORGANISM: Rattus norvegicus

<400> SEQUENCE: 39

Leu Arg Thr Lys Ile Glu Ser Gly Glu Gly Thr Ile Pro Val
1               5                   10

<210> SEQ ID NO 40
<211> LENGTH: 14
<212> TYPE: PRT
<213> ORGANISM: Mus musculus

<400> SEQUENCE: 40

Leu Arg Thr Lys Ile Glu Ser Gly Glu Gly Thr Ile Pro Val
1               5                   10

<210> SEQ ID NO 41
<211> LENGTH: 14
<212> TYPE: PRT
<213> ORGANISM: Gallus gallus

<400> SEQUENCE: 41

Leu Arg Thr Lys Ile Glu Ser Gly Glu Gly Thr Ile Pro Val
1               5                   10

<210> SEQ ID NO 42
<211> LENGTH: 14
<212> TYPE: PRT
<213> ORGANISM: Drosophila melanogaster

<400> SEQUENCE: 42
```

```
Leu Arg Thr Lys Ile Glu Ser Gly Glu Gly Thr Ile Pro Val
1               5                   10
```

<210> SEQ ID NO 43
<211> LENGTH: 14
<212> TYPE: PRT
<213> ORGANISM: Takifugu rubripes

<400> SEQUENCE: 43

```
Leu Arg Thr Lys Ile Glu Ser Gly Glu Gly Thr Ile Pro Val
1               5                   10
```

<210> SEQ ID NO 44
<211> LENGTH: 14
<212> TYPE: PRT
<213> ORGANISM: Danio rerio

<400> SEQUENCE: 44

```
Leu Arg Thr Lys Ile Glu Ser Gly Glu Gly Thr Ile Pro Val
1               5                   10
```

<210> SEQ ID NO 45
<211> LENGTH: 14
<212> TYPE: PRT
<213> ORGANISM: Doryteuthis opalescens

<400> SEQUENCE: 45

```
Leu Arg Thr Lys Ile Glu Ser Gly Glu Gly Thr Ile Pro Val
1               5                   10
```

<210> SEQ ID NO 46
<211> LENGTH: 14
<212> TYPE: PRT
<213> ORGANISM: Homo sapiens

<400> SEQUENCE: 46

```
Leu Arg Thr Lys Ile Glu Ser Gly Glu Gly Thr Val Pro Val
1               5                   10
```

<210> SEQ ID NO 47
<211> LENGTH: 14
<212> TYPE: PRT
<213> ORGANISM: Homo sapiens

<400> SEQUENCE: 47

```
Leu Arg Thr Lys Val Glu Asn Gly Glu Gly Thr Ile Pro Val
1               5                   10
```

<210> SEQ ID NO 48
<211> LENGTH: 20
<212> TYPE: PRT
<213> ORGANISM: Homo sapiens

<400> SEQUENCE: 48

```
Pro Asn Phe Ser Val Asn Trp Thr Val Gly Asp Ser Ala Ile Glu Val
1               5                   10                  15

Ile Asn Ala Thr
            20
```

<210> SEQ ID NO 49
<211> LENGTH: 20
<212> TYPE: PRT
<213> ORGANISM: Rattus norvegicus

<400> SEQUENCE: 49

```
Pro Asn Phe Ser Val Asn Trp Thr Val Gly Asp Thr Ala Ile Glu Val
1               5                   10                  15

Ile Asn Ala Thr
            20

<210> SEQ ID NO 50
<211> LENGTH: 20
<212> TYPE: PRT
<213> ORGANISM: Mus musculus

<400> SEQUENCE: 50

Pro Asn Phe Ser Val Asn Trp Thr Val Gly Asp Ala Thr Ile Glu Val
1               5                   10                  15

Ile Asn Ala Thr
            20

<210> SEQ ID NO 51
<211> LENGTH: 20
<212> TYPE: PRT
<213> ORGANISM: Gallus gallus

<400> SEQUENCE: 51

Pro Asn Phe Ser Val Asn Trp Thr Val Gly Asp Thr Gly Leu Glu Val
1               5                   10                  15

Ile Asn Ala Thr
            20

<210> SEQ ID NO 52
<211> LENGTH: 20
<212> TYPE: PRT
<213> ORGANISM: Drosophila melanogaster

<400> SEQUENCE: 52

Pro Asn Phe Gly Ile Asn Trp Thr Ile Gly Asp Thr Glu Leu Glu Val
1               5                   10                  15

Val Asn Ser Leu
            20

<210> SEQ ID NO 53
<211> LENGTH: 21
<212> TYPE: PRT
<213> ORGANISM: Takifugu rubripes

<400> SEQUENCE: 53

Pro Asn Phe Arg Val Asn Trp Thr Val Gly Asp Asn Gln Gly Leu Lys
1               5                   10                  15

Val Ile Asn Ala Thr
            20

<210> SEQ ID NO 54
<211> LENGTH: 20
<212> TYPE: PRT
<213> ORGANISM: Danio rerio

<400> SEQUENCE: 54

Pro Asn Phe Ser Val Asn Trp Thr Val Gly Asp Gln Gly Leu Glu Ile
1               5                   10                  15

Ile Asn Ala Thr
            20

<210> SEQ ID NO 55
```

```
<211> LENGTH: 20
<212> TYPE: PRT
<213> ORGANISM: Doryteuthis opalescens

<400> SEQUENCE: 55

Pro Asn Phe Gly Ile Asn Trp Arg Arg Asn Asp Asp Ser Phe Glu Val
1               5                   10                  15

Ile Asn Ala Met
            20

<210> SEQ ID NO 56
<211> LENGTH: 20
<212> TYPE: PRT
<213> ORGANISM: Homo sapiens

<400> SEQUENCE: 56

Pro Pro Phe Ser Met Asn Trp Val Val Gly Ser Ala Asp Leu Glu Ile
1               5                   10                  15

Ile Asn Ala Thr
            20

<210> SEQ ID NO 57
<211> LENGTH: 21
<212> TYPE: PRT
<213> ORGANISM: Homo sapiens

<400> SEQUENCE: 57

Lys Glu Thr Ser Val Asn Trp Cys Leu Ala Asp Gly Tyr Asp Leu Glu
1               5                   10                  15

Ile Leu Asp Gly Thr
            20
```

COMPOSITIONS AND METHODS FOR IDENTIFYING RNA BINDING POLYPEPTIDE TARGETS

CROSS-REFERENCE TO RELATED APPLICATION

This Application is a Continuation of U.S. application Ser. No. 16/317,749 filed Jan. 14, 2019, which is a U.S. national phase application under 35 U.S.C. § 371 of PCT International Application Serial No. PCT/US2016/054525, filed Sep. 29, 2016, which claims the benefit of U.S. Provisional Application No. 62/364,170, filed Jul. 19, 2016, all of which are incorporated herein by reference.

STATEMENT OF RIGHTS TO INVENTIONS MADE UNDER FEDERALLY SPONSORED RESEARCH

This invention was made with government support under Grant No. ROI DA-037721 awarded by the National Institutes of Health. The government has certain rights in the invention.

SEQUENCE LISTING

The instant application contains a Sequence Listing which has been submitted electronically in ASCII format in U.S. application Ser. No. 16/317,749 and is hereby incorporated by reference in its entirety. Said ASCII copy, created on May 23, 2022 is named "BDV0001US2C_ST25" and is 101,220 bytes in size.

BACKGROUND OF THE INVENTION

Post-transcriptional regulation of gene expression is mediated by a host of proteins that bind to pre-mRNA and mRNA. Their activity is important for the correct splicing, localization, and translation of cellular components, and their dysregulation is implicated in numerous human diseases. A complete functional understanding of any RNA-binding polypeptide (RBP) requires the identification of its RNA targets. However, identifying biologically relevant RBP targets is challenging. Although there are very good approaches to define in vitro targets, in vivo target identification is a more complicated exercise. There is growing appreciation that even seemingly homogenous tissues are composed of different cell types that can exhibit striking differences in gene expression, proteome, and phenotypic output. Cell types can be broken down even further into subpopulations, and single-cell transcriptional studies have revealed substantial gene expression differences, even between individual cells of the same apparent type. Therefore, because the targets of many RBPs are also likely to be different between tissue and cell types, it is crucial to identify cell-specific targets.

Traditional methods of RBP target identification, typically immunoprecipitation of RBP-bound target RNAs, are generally performed on mixed tissues and, as such, are plagued by issues such as post-lysis in vitro association of RBPs with spurious targets. Furthermore, results can change dramatically with seemingly subtle differences in experimental conditions. The long list of candidate targets for FMRP (an RBP associated with Fragile X syndrome) with little overlap between labs is a testament to this fact. Similarly, multiple studies performed on the ALS-associated RBP TDP-43 have also yielded strikingly non-overlapping sets of targets.

More sophisticated methods include the current gold standard for the identification of RNA-binding polypeptide (RBP) targets in vivo, CLIP (crosslinking and immunoprecipitation) and variants thereof. These methods are based on immunoprecipitation and involve creating covalent interactions between the RBP and its targets within cells and tissues, digesting unprotected RNA, and sequencing the remaining "bound" RNA. Despite its myriad advantages, CLIP has several disadvantages. Prominent among them is the requirement for a high-affinity, specific antibody and the inefficiency of crosslinking (generally 1%-5%). CLIP therefore requires rather large amounts of material (currently millions of cells) and, as such, is best suited to the examination of targets in whole tissue rather than in specific cells.

It should be possible to identify cell-specific RBP targets using CLIP (using an epitope-tagged RBP expressed in a cell-specific manner), but this is still technically challenging. Crosslinking is compromised by limited UV penetration in some tissues and, more importantly, by the low amounts of material in restricted cell populations. Although CLIP was first described in 2005 no such cell-specific experiments have yet been published. Accordingly, improved methods for identifying RBP targets are required.

SUMMARY OF THE INVENTION

As described below, the present invention features fusion polypeptides comprising an RNA binding polypeptide operationally linked to an RNA modifying enzyme (e.g., adenosine deaminase, cytidine deaminase), and methods of use therefore.

In one aspect the invention provides a fusion polypeptide containing an RNA binding polypeptide, or fragment thereof, fused to an RNA editing enzyme or fragment thereof. In one embodiment, the RNA editing enzyme is adenosine deaminase or cytidine deaminase. In another embodiment, the RNA binding polypeptide is selected from the group consisting of Zipcode binding polypeptide 1 (ZBP1), Fus, Tdp43, EIF4EBP1, and HuR. In another embodiment, the RNA editing enzyme is the catalytic domain of adenosine deaminase or cytidine deaminase. In another embodiment, the fusion polypeptide further contains a sequence tag for purification or a detectable moiety.

In another aspect, the invention provides an expression vector containing a nucleic acid sequence encoding the polypeptide of any previous claim. In one embodiment the vector further contains a promoter operably linked to the nucleic acid sequence. In another embodiment, the promoter is positioned for expression in a cell. In another embodiment, the promoter is an insect or mammalian promoter.

In another aspect, the invention provides a host cell containing the expression vector of any previous claim. In one embodiment, the cell is a eukaryotic cell. In another embodiment, the cell is selected from the group consisting of a bacterial cell, a mammalian cell, and an insect cell.

In another aspect, the invention provides a mammalian host cell containing the fusion polypeptide of any previous claim. In one embodiment, the cell is a mammalian cell derived from a human or animal subject. In another embodiment, the cell is a neoplastic cell. In another embodiment, the cell is selected from the group consisting of adipocytes, bone marrow derived cells, epidermal cells, endothelial cells, fibroblasts, hematopoietic cells, hepatocytes, myocytes, neurons, pancreatic cells, and their progenitor cells or stem cells.

In another aspect, the invention provides a method for producing a fusion polypeptide of any previous claim, the method involving providing a cell transformed with the expression vector of any previous claim positioned for expression in the cell; and culturing the cell under conditions for expressing the fusion polypeptide.

In another aspect, the invention provides a viral vector containing a polynucleotide encoding a fusion polypeptide of any previous claim.

In another aspect, the invention provides an adeno-associated viral (AAV) vector containing a fusion polypeptide of any previous claim, where the polypeptide is operably linked to a promoter positioned for expression in a mammalian cell.

In another aspect, the invention provides a method for identifying an RNA binding polypeptide target, the method involving contacting a transcriptome of a cell with a fusion polypeptide containing an RNA binding polypeptide or fragment thereof to the catalytic domain of an RNA-editing enzyme; and detecting novel RNA editing events in said transcriptome. In one embodiment, the RNA-editing enzyme is an adenosine deaminase or cytidine deaminase. In another embodiment, the RNA binding polypeptide is selected from the group consisting of Zipcode binding polypeptide 1 (ZBP1), Fus, Tdp43, EIF4EBP1, and HuR. In another embodiment, the RNA editing enzyme is the catalytic domain of adenosine deaminase or cytidine deaminase. In another embodiment, the detecting is by sequencing RNA In another embodiment, the fusion polypeptide is expressed in a cell in vitro or in vivo.

Compositions and articles defined by the invention were isolated or otherwise manufactured. Other features and advantages of the invention will be apparent from the detailed description, and from the claims.

Definitions

Unless defined otherwise, all technical and scientific terms used herein have the meaning commonly understood by a person of ordinary skill in the art lo which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991) As used herein, the following terms have the meanings ascribed to them below, unless specified otherwise.

By "RNA binding polypeptide-RNA editing enzyme fusion polypeptide" is meant a fusion polypeptide comprising a protein domain derived from an RNA binding polypeptide and a protein domain having polynucleic acid deaminase activity. In one embodiment, the protein domain having polynucleic acid deaminase activity is a catalytic domain of adenosine deaminase or cytidine deaminase.

By "RNA binding protein" or "RNA binding polypeptide" is meant a polypeptide or fragment thereof capable of sequence specific binding to RNA.

By "DNA binding protein" or "DNA binding polypeptide" is meant a polypeptide or fragment thereof capable of sequence specific binding to DNA By "RNA editing enzyme" is meant a polypeptide or fragment thereof having deaminase activity. In one embodiment, the RNA modifying enzyme makes discrete irreversible changes to nucleotides present in an RNA molecule. The deaminase can be an adenosine deaminase, and/or cytidine deaminase. In one embodiment, the RNA modifying enzyme is the catalytic domain of the *Drosophila* homolog of Adenosine Deaminases Acting on RNA (ADAR). In another embodiment, the deaminase is a mammalian deaminase described by Bass et al., PNAS Vol. 109, number 48, E3295-E3304, which is incorporated herein by reference in its entirety. In particular embodiments, an RNA modifying enzyme is human ADAR1, 2, 3, or 4. The sequences of exemplary ADARs are provided below:

```
Drosophila melanogaster = "adenosine deaminase acting on RNA, isoform P"
/protein id = "NP_001284792.1"

/db_xref = "GI:665389189"

/db xref = "FLYBASE:FBpp0308383"

/db xref = "FLYBASE:FBgn0026086"

/db_xref = "GeneID:31130"
                                                                SEQ ID NO: 1
="MNGYNRKLPQKRGYEMPKYSDPKKKMCKERIPQPKNTVAMLNEL

RHGLIYKLESQTGPVHAPLFTISVEVDGQKYLGQGRSKKVARIEAAATALRSFIQFKD

GAVLSPLKPAGNLDFTSDEHLENDVSKSAITVDGQKKVPDKGPVMLLYELFNDVNFEC

INIDGAQNNCRFKMTVTINEKKFDGTGPSKKTAKNAAAKAALASLCNISYSPMVVPQK

NVPLPIDDKSSSMELPQIHADTIGRLVLEKFMEVIKGQEAYSRRKVLAGIVMTENMNF

CEAKVISVSTGTKCVSGEHMSVNGAVLNDSHAEIVSRRCLLKYLYAQLDLQCNQGIVV

ORIGIN
                                                                SEQ ID NO: 2
    1 tattgtgata actgctcaca tcgctagatt ccgagcaaca aaaaagcgac gaagggtcat 61 tgttattttt tctaatgcaa tgtaatgcag caaatgtgca gatttgaaca agtgtaacgc 121 gatttatgtt taatccgcat cgaggaacca aatcgaagta aacgcgcggc cagagaaaag 181 agcagcaccg caccgaagat aaaacaaaca agcattgatt tgtttgtccg gccatgtcag
```

-continued

```
 241 tgtgtgtgtc acaagggctt gcaagtgtgt gcgtgtgtcc gtgcgtgtac gtgggtgctt 301 ttttttttct cccgagtgcc gccaagtgaa atatgcaatt gcacgccact gcagttgcag 361 ccacacaaat cctatcctaa tcgacgaaac agcgaagcga ggaggctaga atcggctgcc 421 caacgaagag agcagaaccg ttaacaaatg acactctgcc gatacagcga agtaaaaatc 481 aataattaga gcaaaaagcc ggtgagtgca ccatccgata tcaacatgaa tggctataac 541 cgaaaattgc cacaaaaacg tggctatgag atgccaaaat actctgatcc aaaaaagaaa 601 atgtgcaagg agcgcattcc ccagccgaag aacacggtgg ccatgctgaa tgagctaaga 661 catggactga tttacaaatt ggagtcacag actggtccgg tacacgcacc tctattcacg 721 atatccgtgg aggtcgatgg acagaaatac ttgggccagg gccgtagtaa aaaagttgca 781 cgcatcgaag cagcagcaac tgcactgcgc agctttatac agtttaagga tggagcagtt 841 ctgtcgcctc tgaagccggc gggcaacttg gactttacca gcgatgaaca tcttgaaaat 901 gatgtcagca aaagtgctat tactgttgac ggtcagaaga aggttccaga taagggtcct 961 gtcatgctcc tctacgaatt atttaatgac gttaatttcg aatgcattaa tattgacggc 1021 gcccagaaca attgtcgctt caaaatgacc gtcacaatca acgaaaagaa gttcgatgga 1081 acaggtcctt ccaaaaagac ggcgaaaaat gcggcagcta aggcggcact tgcttcgtta 1141 tgcaatattt cctacagtcc aatggtggtg ccacagaaga acgtacccct gccaatcgac 1201 gacaagtcgt catcgatgga gttgcctcag atacacgcgg atacgattgg tcggttggtc 1261 ttagaaaagt tcatggaagt aatcaagggc caggaggctt actcgcgtcg aaaggtatta 1321 gcgggcattg taatgactga aacatgaatt ttttgtgaag ccaaagttat ttcagtttcg 1381 acgggcacca gtgtgtcag cggtgagcat atgagtgtga acggagctgt cctaaatgat 1441 tcccatgctg aaatagtctc caggcgttgt cttctcaaat atttatatgc acagctggac 1501 cttcagtgca atcagggtat agttgtttga tgtatatgct aagttcagtt tacgtatact 1561 aataatacca tagaacttaa atctaagagt aatgcataat ctagttgtta aatgttgata 1621 tcgaaaatgt acgctttacc agcaagaatt gcctacatag aagctaaagt tccgatttgt 1681 gctcattaac cgtatacgag cacaaacttt tatttttttct ttcttttaca cattataaac 1741 aagcacttta agctaactta tgttttcccc gtctgatcgt tttagaaggt gtttatacaa 1801 aattaaattt taagggcaaa ccatcttaaa aataaacaat ttgtaaacat t
```

ADAR1 AA Sequence
NCBI Reference Sequence: XP_016855526.1

SEQ ID NO: 3

```
  1 maeikekicd ylfnvsdssa lnlakniglt kardinavli dmerqgdvyr qgttppiwhl 61 tdkkrermqi krntnsvpet apaaipetkr naefltcnip tsnasnnmvt tekvengqep 121 viklenrqea rpeparlkpp vhyngpskag yvdfengqwa tddipddlns iraapgefra 181 imempsfysh glprcspykk ltecqlknpi sglleyaqfa sqtcefnmie qsgpphepf 241 kfqvvingre fppaeagskk vakqdaamka mtilleeaka kdsgkseess hystekesek 301 taesqtptps atsffsgksp vttllecmhk lgnscefrll skegpahepk fqycvavgaq 361 tfpsvsapsk kvakqmaaee amkalhgeat nsmasdnqpe gmisesldnl esmmpnkvrk 421 igelvrylnt npvgglleya rshgfaaefk lvdqsgpphe pkfvyqakvg grwfpavcah 481 skkqgkqeaa daalrvlige nekaermgft elpltgstfh dqiamlshrc fntltnsfqp 541 sllgrkilaa iimkkdsedm gvvslgtgn rcvkgdslsl kgetvndcha eiisrrgfir 601 flyselmkyn sqtakdsife pakggeklqi kktvsfhlyi stapcgdgal fdkscsdram 661 estesrhypv fenpkqgklr tkvengegti pvessdivpt wdgirlgerl rtmscsdkil
```

```
721 rwnvlglqga llthflqpiy lksvtlgylf sqghltraic crvtrdgsaf edglrhpfiv 781 nhpkvgrvsi ydskrqsgkt ketsvnwcla dgydleildg trgtvdgprn elsrvskkni 841 fllfkklcsf ryrrdllrls ygeakkaard yetaknyfkk glkdmgygnw iskpqeeknf 901 ylcpv /gene = "ADARB1"

/gene_synonym = "ADAR2; DRABA2; DRADA2; RED1"

/coded_by = "NM_001160230.1::436 . . . 2460"

/note = "isoform 7 is encoded by transcript variant 7"

db_xref = "GeneID:104"

/db_xref = "HGNC::HGNC:226"

/db_xref = "MIM:601218"

ORIGIN
                                                                SEQ ID NO: 4
  1 mdiedeenms ssstdvkenr nldnvspkdg stpgpgegsq lsnggggpg rkrpleegsn 61 ghskyrlkkr rktpgpvlpk nalmqlneik pglqytllsq tgpvhaplfv msvevngqvf 121 egsgptkkka klhaaekalr sfvqfpnase ahlamgrtls vntdftsdqa dfpdtlfngf 181 etpdkaeppf yvgsngddsf sssgdlslsa spvpaslaqp plpvlppfpp psgknpvmil 241 nelrpglkyd flsesgesha ksfvmsvvvd gqffegsgrn kklakaraaq salaaifnlh 301 ldqtpsrqpi pseglqlhlp qvladavsrl vlgkfgdltd nfsspharrk vlagvvmttg 361 tdvkdakvis vstgtkcing eymsdrglal ndchaeiisr rsllrflytq lelylnnkdd 421 qkrsifqkse rggfrlkenv qfhlyistsp cgdarifsph epileepadr hpnrkargql 481 rtkiesgegt ipvrsnasiq twdgvlqger lltmscsdki arwnvvgiqg sllsifvepi 541 yfssiilgsl yhgdhlsram yqrisniedl pplytlnkpl lsgisnaear qpgkapnfsv 601 nwtvgdsaie vinattgkde lgrasrlckh alycrwmrvh gkvpshllrs kitkpnvyhe 661 sklaakeyqa akvh
```

In particular embodiments, the human ADAR comprises a mutation. Exemplary mutations include those provided below in Table 1.

TABLE 1

ADAR MUTATIONS AND AMINO ACID SUBSTITUTIONS

| Residue | Amino acid substitution* | Editing† UAG | Editing† GAC |
|---|---|---|---|
| 488 | Q (25), N (3) | ++++ | +++ |
|  | E (2), A (1), S (1), M (1), R (1) | ++++ | − |
|  | F (1), L (3), W (1) | − | − |
| 490 | T (28), C (8), S (8) | ++++ | − |
|  | A (3) | ++ | − |
|  | F (1), Y (1) | + | − |
|  | R (2), K (1), P (3), E (2) | − | − |
| 493 | T (4), S (13), A (4) | ++++ | + |
|  | V (1), R (1), D (1), P (1), G (1) | ++++ | − |
| 597 | K (19), R (13) | ++++ | + |
|  | N (3), A (1), E (1), H (3), G (1), Y (1) | ++++ | − |
|  | F (2) | − | − |
| 613 | K (6), R (7) | ++++ | + |
|  | N (1), A (1), E (1) | ++++ | − |

*WT residues are in bold. The number beside each amino acid substitution indicates number of clones isolated In one embodiment, the RNA editing enzyme comprises E488Q, a V493A, and/or T490A. In one embodiment, the RNA editing enzyme comprises E488Q and a V493A; E488Q and T490A; or E488Q, V493A, and T490A.

By "RNA editing enzyme polynucleotide" is meant a polynucleotide sequence encoding an RNA modifying enzyme.

By "eIF4EBP1 polypeptide" is meant a protein having at least about 85% amino acid identity to the sequence provided at NCBI Reference sequence NP_004086.1, or a fragment thereof and having polynucleotide binding activity. Eukaryotic translation initiation factor 4E-binding polypeptide or "eIF4EBP1" is a protein that can directly interact with eukaryotic translation initiation factor 4E (eIF4E), which is a limiting component of the multisubunit complex that recruits 40S ribosomal subunits to the 5' end of mRNAs. Interaction of this protein with eIF4E inhibits complex assembly and represses translation. The eIF4EBP1 protein is phosphorylated in response to various signals including UV irradiation and insulin signaling, resulting in its dissociation from eIF4E and activation of cap-dependent mRNA translation. An exemplary eIF4EBP1 amino acid sequence is provided below:

Eukaryotic Translation Initiation Factor 4E-Binding Polypeptide 1 (ETF4EBP1) [*HOMO SAPIENS*]

```
                                                          SEQ ID NO: 5
  1  msggsscsqt psraipatrr vvlgdgvqlp pgdysttpgg tlfsttpggt riiydrkflm 61  ecrnspvtkt pprdlptipg vtspssdepp measqshlrn spedkragge esqfemdi
```

By "eIF4EBP1 polynucleotide" is meant a nucleic acid molecule encoding an eIF4EBP1 (e.g., Eukaryotic translation initiation factor 4E-binding polypeptide 1). An exemplary eIF4EBP1 S polynucleotide sequence is provided at NCBI Reference Sequence: NM_004095.3, and reproduced herein below.

```
                                                          SEQ ID NO: 6
  1 ggggcgaggc ggagcgaggc tggaggcgcg ggagggcagc gagaggttcg cgggtgcagc 61 gcacaggaga ccatgtccgg gggcagcagc tgcagccaga ccccaagccg ggccatcccc 121 gccactcgcc gggtggtgct cggcgacggc gtgcagctcc cgcccgggga ctacagcacg 181 accccggcg gcacgctctt cagcaccacc ccgggaggta ccaggatcat ctatgaccgg 241 aaattcctga tggagtgtcg gaactcacct gtgaccaaaa cacccccaag ggatctgccc 301 accattccgg gggtcaccag cccttccagt gatgagcccc ccatggaagc cagccagagc 361 cacctgcgca atagcccaga agataagcgg gcgggcggtg aagagtcaca gtttgagatg 421 gacatttaaa gcaccagcca tcgtgtggag cactaccaag gggcccctca gggccttcct 481 gggaggagtc ccaccagcca ggccttatga aagtgatcat actgggcagg cgttggcgtg 541 gggtcggaca ccccagccct ttctccctca ctcagggcac ctgccccctc ctcttcgtga 601 acaccagcag atacctcctt gtgcctccac tgatgcagga gctgccaccc caaggggagt 661 gaccctgcc agcacaccct gcagccaagg gccaggaagt ggacaagaac gaacccttcc 721 ttccgaatga tcagcagttc cagcccctcg ctgctggggg cgcaaccacc ccttccttag 781 gttgatgtgc ttgggaaagc tccctccccc tccttcccca agagaggaaa taaaagccac 841 cttcgcccta gggccaagaa aaaaaaaaaa aaaaaaa
```

By "FMRP polypeptide" is meant a protein having at least about 85% amino acid identity to the sequence provided at NCBI Reference sequence Q06787.1, or a fragment thereof and having polynucleotide binding activity. As used herein, dFMR1, the *Drosophila* ortholog of FMRP (fragile X mental retardation protein) was fused to the ADARcd to create a TRIBEfusion polypeptide. FMRP and dFMR1 are thought to have roles in mRNA localization and translational regulation in neurons. An exemplary FMRP amino acid sequence is provided below:

Fragile X Mental Retardation Protein 1 (FMRP1) [*Homo sapiens*]

```
                                                                SEQ ID NO: 7
  1 meelvvevrg sngafykafv kdvhedsitv afennwqpdr qipfhdvrfp ppvgynkdin 61 esdevevysr anekepccww lakvrmikge fyvieyaacd atyneivtie rlrsvnpnkp 121 atkdtfhkik idvpedlrqm cakeaahkdf kkavgafsvt ydpenyqlvi lsinevtskr 181 ahmlidmhfr slrtklslim rneeaskqle ssrqlasrfh eqfivredlm glaigthgan 241 iqqarkvpgv taidldedtc tfhiygedqd avkkarsfle faedviqvpr nlvgkvigkn 301 gkliqeivdk sgvvrvriea eneknvpqee eimppnslps nnsrvgpnap eekkhldike 361 nsthfsqpns tkvqrvlvas svvagesqkp elkawqgmvp fvfvgtkdsi anatvlldyh 421 lnylkevdql rlerlqideq lrqigassrp ppnrtdkeks yvtddgqgmg rgsrpyrnrg 481 hgrrgpgyts gtnseasnas etesdhrdel sdwslaptee eresflrrgd grrrggggrg 541 qggrgrgggf kgnddhsrtd nrprnpreak grttdgslqi rvdcnnersv htktlqntss 601 egsrlrtgkd rnqkkekpds vdgqqplvng vp
```

By "FMRP polynucleotide" is meant a nucleic acid molecule encoding FMRP (e.g., fragile X mental retardation protein). An exemplary FRMP polynucleotide sequence is provided at NCBI Reference Sequence: AB209188.1, and reproduced herein below:

SEQ ID NO: 8

```
   1 actttgaagt ggtcatcaaa gagatcagtt agaagaactg atctgcagtg tgtgacagac
  61 caggaaagtg atatccagag gattgccacc atgaagttgt cattttagt ggagaggaag
 121 caggagacca gaaagtgacc aaggatctgt ccatttagtt ccaggagata tgactgccag
 181 agtggtatcc ttagtgggct gaatgttcag tggtcttact ttagtgacca agcaacaaga
 241 cagtagggca tggtcagtaa ctttcagtca attttgctt actaggataa agcaaaaata
 301 agcttataca tttttagata cattttttgt aacttgctga gtacccaagg aaagtgtgct
 361 tgtatttatg ggcgtctatt ttcagagcac taattattgc tgaattagaa cagaaatata
 421 ggaaaactga tttttacaag gagcttcaaa gcaatctcag gtagtttctg attatgtatc
 481 tctgcctacc tcggggtaca tagacagggt tacaatttgg ttgaggatat atgacatgtg
 541 gtttttaaag acacctaggg gcatttttaag aaaatttcct cgatatctga aaatctgtag
 601 atttcaaaat tatgttaatc atgaaatatt ctgtgttgta attttttgtgt aggtgtattc
 661 cagagcaaat gaaaaagagc cttgctgttg gtggttagct aaagtgagga tgataaaggg
 721 tgaggtagga aaatgcctat ttaaatttt ttcttatatt gtttcctttt tttaaaccca
 781 ggttgtacat tcccgtgtgg atttctattt tgaagtaata tctaattttg agtaatttaa
 841 ttaaaatgtt ttcactatgt gttcagtatg tttctgttgg tcataaattt tttcacatag
 901 attatttatt ttaaaataac tgaataggga gaacttctta ttcttacttt aaaaattgtg
 961 attagaagtg acttttattt atttctcagt tttatgtgat agaatatgca gcatgtgatg
1021 caacttacaa tgaaattgtc acaattgaac gtctaagatc tgttaatccc aacaaacctg
1081 ccacaaaaga tactttccat aagatcaagc tggatgtgcc agaagactta cggcaaatgt
1141 gtgccaaaga ggcggcacat aaggatttta aaaaggcagt tggtgccttt tctgtaactt
1201 atgatccaga aaattatcag cttgtcattt tgtccatcaa tgaagtcacc tcaaagcgag
1261 cacatatgct gattgacatg cactttcgga gtctgcgcac taagttgtct ctgataatga
1321 gaaatgaaga agctagtaag cagctggaga gttcaaggca gcttgcctcg agatttcatg
1381 aacagtttat cgtaagagaa gatctgatgg gtctagctat tggtactcat ggtgctaata
1441 ttcagcaagc tagaaaagta cctggggtca ctgctattga tctagatgaa gatacctgca
1501 catttcatat ttatggagag gatcaggatg cagtgaaaaa agctagaagc tttctcgaat
1561 ttgctgaaga tgtaatacaa gttccaagga acttagtagg caaagtaata ggaaaaaatg
1621 gaaagctgat tcaggagatt gtggacaagt caggagttgt gagggtgagg attgaggctg
1681 aaaatgagaa aaatgttcca caagaagagg aaattatgcc accaaattcc cttccttcca
1741 ataattcaag ggttggacct aatgccccag aagaaaaaaa catttagat ataaaggaaa
1801 acagcaccca ttttttctcaa cctaacagta caaaagtcca gagggtatg gtaccatttg
1861 ttttttgtggg aacaaaggac agcatcgcta atgccactgt tcttttggat tatcacctga
1921 actatttaaa ggaagtagac cagttgcgtt tggagagatt acaaattgat gagcagttgc
1981 gacagattgg agctagttct agaccaccac caaatcgtac agataaggaa aaaagctatg
2041 tgactgatga tggtcaagga atgggtcgag gtagtagacc ttacagaaat aggggggcacg
2101 gcagacgcgg tcctggatat acttcaggaa ctaattctga agcatcaaat gcttctgaaa
2161 cagaatctga ccacagagac gaactcagtg attggtcatt agctccaaca gaggaagaga
```

-continued

```
2221 gggagagctt cctgcgcaga ggagacggac ggcggcgtgg aggggagga agaggacaag
2281 gaggaagagg acgtggagga ggcttcaaag gaaacgacga tcactcccga acagataatc
2341 gtccacgtaa tccaagagag gctaaaggaa gaacaacaga tggatccctt cagatcagag
2401 ttgactgcaa taatgaaagg agtgtccaca ctaaaacatt acagaatacc tccagtgaag
2461 gtagtcggct gcgcacgggt aaagatcgta accagaagaa agagaagcca gacagcgtgg
2521 atggtcagca accactcgtg aatggagtac cctaaactgc ataattctga agttatattt
2581 cctataccat ttccgtaatt cttattccat attagaaaac tttgttaggc caaagacaaa
2641 tagtaggcaa gatggcacag gcatgaaat gaacacaaat tatgctaaga atttttatt
2701 ttttggtatt ggccataagc aacaattttc agatttgcac aaaaagatac cttaaaattt
2761 gaaacattgc ttttaaaact acttagcact tcagggcaga ttttagtttt attttctaaa
2821 gtactgagca gtgatattct ttgttaattt ggaccatttt cctgcattgg gtgatcattc
2881 accagtacat tctcagtttt tcttaatata tagcatttat ggtaatcata ttagacttct
2941 gttttcaatc tcgtatagaa gtcttcatga aatgctatgt catttcatgt cctgtgtcag
3001 tttatgtttt ggtccacttt tccagtattt tagtggaccc tgaaatgtgt gtgatgtgac
3061 atttgtcatt ttcattagca aaaaaagttg tatgatctgt gccttttta tatcttggca
3121 ggtaggaata ttatatttgg atgcagagtt cagggaagat aagttggaaa cactaaatgt
3181 taaagatgta gcaaaccctg tcaaacatta gtactttata aagaatgca tgctttccat
3241 attttttcc ttacataaac atcaggttag gcagtataaa gaataggact tgttttgtt
3301 tttgttttgt tgcactgaag tttgataaat agtgttattg agagagatgt gtaattttc
3361 tgtatagaca gggagaagaa gaactatctt catctgagag aggctaaaat gttttcagct
3421 aggaacaaat cttcctggtc gaaagttagt aggatatgcc tgctctttgg cctgatgacc
3481 aattttaact tagagctttt tttttttaat tttgtctgcc ccaagttttg tgaaatttt
3541 catatttaa tttcaagctt attttggaga gataggaagg tcatttccat gtatgcataa
3601 taatcctgca aagtacaggt actttgtcta agaaacattg gaagcaggtt aaatgttttg
3661 taaactttga aatatatggt ctaatgttta agcagaattg gaaagacta agatcggtta
3721 acaaataaca acttttttt cttttttct tttgttttt gaagtgttgg ggtttggttt
3781 tgttttttga gtcttttttt ttaagtgaaa tttattgagg aaaaatatgt gaaggacctt
3841 cactctaaga tgttatattt ttcttaaaaa gtaactccta gtaggggtac cactgaatct
3901 gtacagagcc gtaaaaactg aagttctgcc tctgatgtat tttgtgagtt tgtttctttg
3961 aattttcatt ttacagttac ttttccttgc atacaaacaa gcatataaaa tggcaacaaa
4021 ctgcacatga tttcacaaat attaaaaagt cttttaaaaa gtattgccaa acattaatgt
4081 tgatttctag ttatttattc tgggaatgta tagtattgaa aacagaaatt ggtaccttgc
4141 acacatcatc tgtaagctgt ttggttttaa aatactgtag ataattaacc aaggtagaat
4201 gaccttgtaa tgtaactgct cttgggcaat attctctgta catattagcg acaacagatt
4261 ggatttatg ttgacatttg tttggttata gtgcaatata ttttgtatgc aagcagtttc
4321 aataaagttt gatcttcctc tgctaaattg atgttgatgc aatccttaca aatgattgct
4381 tttaaaattt taagctagga aaagaaatct atagaaagtg ttctgttaca aaatgtaact
4441 gttaccattg gaaatttcac gtcataggaa gttagccttt atctaccaac tttcaagaac
4501 ttgtttaata aagcgaaaaa ctcaaccaaa tggtacaaaa ccacagtgta ccattaaaat
4561 atgcactaag tctctttttt acaaaggctg tattcagcaa ggcgctaact tgcttaaatg
```

-continued
```
4621 tgaattacta acttctaaaa ctgtactttg attcacatgt tttcaaatgg agttggagtt 4681 cattcatatt acaatatttg tgtgctaaac gtgtatgttt ttcagttcaa agtcatgatg 4741 tttttaaaat cttattaaag tttcaaaaat ctgaagattg tttatctaga tgtaaatttt 4801 tattaaaaag ttgcacttat gaaaaagc
```

By "FUS polypeptide" is meant a protein having at least about 85% amino acid identity to the sequence provided at NCBI Reference sequence P35637.1, or a fragment thereof and having polynucleotide binding activity. FUS RNA binding polypeptide or "Fus" is a protein that can bind RNA, single-stranded DNA, and with lower affinity, double-stranded DNA. FUS gene been implicated in the pathogenesis of diseases, for example, myxoid liposarcoma, low grade fibromyxoid sarcoma, frontotemporal lobar dementias (FTLDs), amyotrophic lateral sclerosis (ALS) and frontotemporal dementia (FTD). An exemplary FUS amino acid sequence is provided below:

RNA-Binding Polypeptide Fus [*Homo sapiens*]

```
                                                                SEQ ID NO: 9
  1 masndytqqa tqsygayptq pqqgysqqss qpygqqsysg ysqstdtsgy gqssyssygq 61 sqntgygtqs tpqgygstgg ygssqssqss ygqqssypgy gqqpapssts gsygsssqss 121 sygqpqsgsy sqqpsyggqq qsygqqqsyn ppqgygqqnq ynsssggggg ggggnygqd 181 qssmssgggs gggygnqdqs ggggsggygq qdrggrgrgg sggggggggg gynrssggye 241 prgrgggrgg rggmggsdrg gfnkfggprd qgsrhdseqd nsdnntifvq glgenvties 301 vadyfkqigi iktnkktgqp minlytdret gklkgeatvs fddppsakaa idwfdgkefs 361 gnpikvsfat rradfnrggg ngrggrgrgg pmgrggyggg gsggggrggf psgggggggq 421 qragdwkcpn ptcenmnfsw rnecnqckap kpdgpggpg gshmggnygd drrggrggyd 481 rggyrgrggd rggfrggrgg gdrggfgpgk mdsrgehrqd rrerpy
```

By "FUS polynucleotide" is meant a nucleic acid molecule encoding a FUS or RNA-binding polypeptide FUS polypeptide. An exemplary FUS polynucleotide sequence is provided at NCBI Reference Sequence: NM_004960.3, and reproduced herein below.

```
                                                                SEQ ID NO: 10
  1 acttaagctt cgacgcagga ggcggggctg ctcagtcctc caggcgtcgg tactcagcgg 61 tgttggaact tcgttgcttg cttgcctgtg cgcgcgtgcg cggacatggc ctcaaacgat 121 tatacccaac aagcaaccca aagctatggg gcctacccca cccagcccgg gcagggctat 181 tcccagcaga gcagtcagcc ctacggacag cagagttaca gtggttatag ccagtccacg 241 gacacttcag gctatggcca gagcagctat tcttcttatg ccagagcca gaacacaggc 301 tatggaactc agtcaactcc cagggatat ggctcgactg gcggctatgg cagtagccag 361 agctcccaat cgtcttacgg gcagcagtcc tcctaccctg gctatggcca gcagccagct 421 cccagcagca cctcgggaag ttacggtagc agttctcaga gcagcagcta tgggcagccc 481 cagagtggga gctacagcca gcagcctagc tatggtggac agcagcaaag ctatggacag 541 cagcaaagct ataatccccc tcagggctat ggacagcaga accagtacaa cagcagcagt 601 ggtggtggag gtggaggtgg aggtggaggt aactatggcc aagatcaatc ctccatgagt 661 agtggtggtg gcagtggtgg cggttatggc aatcaagacc agagtggtgg aggtggcagc 721 ggtggctatg gacagcagga ccgtggaggc cgcggcaggg gtggcagtgg tggcggcggc 781 ggcggcggcg gtggtggtta caaccgcagc agtggtggct atgaacccag aggtcgtgga 841 ggtggccgtg gaggcagagg tggcatgggc ggaagtgacc gtggtggctt caataaattt 901 ggtggccctc gggaccaagg atcacgtcat gactccgaac aggataattc agacaacaac
```

-continued

```
 961 accatctttg tgcaaggcct gggtgagaat gttacaattg agtctgtggc tgattacttc 1021 aagcagattg gtattattaa gacaaacaag aaaacgggac agcccatgat taatttgtac 1081 acagacaggg aaactggcaa gctgaaggga gaggcaacgg tctcttttga tgacccacct 1141 tcagctaaag cagctattga ctggtttgat ggtaaagaat tctccggaaa tcctatcaag 1201 gtctcatttg ctactcgccg ggcagacttt aatcggggtg gtggcaatgg tcgtggaggc 1261 cgagggcgag gaggacccat gggccgtgga ggctatggag gtggtggcag tggtggtggt 1321 ggccgaggag gatttcccag tggaggtggt ggcggtggag gacagcagcg agctggtgac 1381 tggaagtgtc ctaatcccac ctgtgagaat atgaacttct cttggaggaa tgaatgcaac 1441 cagtgtaagg cccctaaacc agatggccca ggaggggac caggtggctc tcacatgggg 1501 ggtaactacg gggatgatcg tcgtggtggc agaggaggct atgatcgagg cggctaccgg 1561 ggccgcggcg gggaccgtgg aggcttccga ggggccggg gtggtgggga cagaggtggc 1621 tttggccctg gcaagatgga ttccaggggt gagcacagac aggatcgcag ggagaggccg 1681 tattaattag cctggctccc caggttctgg aacagctttt tgtcctgtac ccagtgttac 1741 cctcgttatt ttgtaacctt ccaattcctg atcacccaag ggttttttg tgtcggacta 1801 tgtaattgta actatacctc tggttcccat taaaagtgac catttagtt aaattttgtt 1861 cctcttcccc cttttcactt tcctggaaga tcgatgtccc gatcaggaag gtagagagtt 1921 ttcctgttca gattaccctg cccagcagga actggaatac agtgttcggg gagaaggcca 1981 aatgatatcc ttgagagcag agattaaact tttctgtcat ggggaaagtt ggtgtataaa 2041 tgagaaatga agaacatggg atgtcatgag tgttggccta aatttgccca gctatgggga 2101 attttttcctt taccacatt atttgcatac tggtcttagt ttatttgcag cagtttatcc 2161 cttttttaaga actctttgat cttttggccc ttttaatggt gaggctcaaa caaactacat 2221 ttaaatgggg cagtattcag atttgaccat ggtggagagc gcttagccac tctgggtctt 2281 tcacaggaag gagagtaact gagtgctgca ggagtttgtg gagtggagtc aggatctagg 2341 aggtgagtga ctcccttcct agctgccctg gtgaacagcg cttgggtaga tacctgctat 2401 aaggagactg tctggctgg gttactttca catcctgcct gtactcagag ggcttgaggt 2461 cattgacatt atgagatttt aggcttgatc ccttttgat tggagggtgg aaggccctcc 2521 taagggaatg ataagtgata agaggggaa ggggttgcag ccaatgagtt aaaaccttag 2581 agcagtgctc ctcagcctct taccatgtgg ttgtaaactt gcacgtacct gccaaccagt 2641 tatttagcat gcttttatt ttagttacac agagcgtaac attaacccaa gagcagaaag 2701 gttttattta cagggttttc gaacttggtt tgtaagacag ctgccatcac aagcatagct 2761 tacaaatgtg ctggggaccc ctaattggga agtgctttcc tctcaaattt ttatttttta 2821 ttttttagaga cagagtcttg ctctgtcatc caggctggag tgcagtggcg tgatctcggc 2881 tcactgtagc ctctgcctcc tgagtttaag cgattctcct gcctcaggag aatcccagct 2941 tctgagtagc tgagactaca ggcgtgggcc accatgccca cctagttttt gcattttag 3001 tggaggtgtg gtttcactgt gttggccagg ctggtctctt aactcctgac ctcaggtgat 3061 ccacctgcct tggcctccca aagtgctgga attacaggca tgagccgctg catctggcca 3121 tcctctcaaa ttttcaagtg ttccacaagt atgttctcta ctgaagagtt gctgcatcct 3181 tgaatcttgg gtgatttgag gcacagaaac tatgactta ttttttgaga tggagttttg 3241 ctcttgttgc ccaggctgga gtgcaatggc acgttttcg gcttaccgca actgccgcct 3301 cctgggttca agcgatagct gggattacag gcatgcgcca ccatgcccag ctaatttatt 3361 tgtattttta gtagagacgg ggtttctcca tgttggtcag gctggtctcg aactcccgac
```

-continued

```
3421 ctcaggtgat gtgcacacct cagcctccca ataaaccatg acttttaaga ggaatagcag 3481 gtttacttcc cctgccagca ttggggtgct ctctaagcaa cagtaggcgg agagtggtct 3541 ggcgtattaa aaacaaagga tcgtcaagtg ggccttccca ggcattgctt tgacttagta 3601 catgtagagg atgtggcagt tctctccgtc cctgccactg ctggtttctt tgttaaatgt 3661 ttagttgaaa tggcctgata cgatatttga gtagttcact gttggtgctt tgcctagcag 3721 gattctaatc ttgctttggt tgtggtcccc tgatgccctc ctgttaggag tggaggaggt 3781 cgaagctcct tgtaagatat gattactggg accattagtg tcaagttcct gtgtccttca 3841 aatggcatat gtgattggcc ttgaccttaa aaggaaatag ggtcccaggt gactgtttag 3901 tgggtaggtc cagtttgggg ggatcttcca ggagaatgga tagagacacc tagcagcaga 3961 gagaacattg gtgcctctca agccaacctc ccacctcagc ctcccaagta gctgggacta 4021 caggtgcttc ctcgctacca cacctgggta attttttttt taattactt ttttttttta 4081 agaaacaggg tttcactggg ttgcccaggc tggtcttgaa ctggcctcaa gtgacctgcc 4141 tgcctcagcc tcccaaagtg ctgggatcac aggtgtgacc cactgcgttt ggccagaata 4201 ctctattctt actgaatgat tgaaatctgt cttgaagcat taggtgtccc attttttgtga 4261 gttggaattg ggacaggcta agtaggaagt gaggagggtg gggagagctg tgctgtaggt 4321 ctgtttgtcc cttccttgat gtagccttca gttagcccttt tcagcttttt tccccatctt 4381 gtgccgggcc ttcctggggtt tcagtacttg gatgtagggc tgcagttatg tcagtggtgg 4441 gtagattgac caggaattaa ggtctagggt ccagcccatg tgagacttga ctcactgatc 4501 tacctttagg catgtcttcc ttccagtctc atccttttta aattttttt ttttttttga 4561 gacggtctca ctctcaccca ggctggattg cagtggtgtg atctcgacca actgcaacct 4621 ctgcctccca cccgcaagct atctgcccac ctcagcctct ggagtagctg ggacgggact 4681 acaggcacct gccaccatga ctggctaatt tttttttgta tttttttgtgg agatggggtc 4741 ttgccatgtt gctcaggctg gtctggtctc aaaactgctc tgggctcaag tgattgtccc 4801 actttggcct cccagagtgc tgggattaag gtgtgagata ctgtgtccgg ctatgaaaat 4861 tttatttta attaacttgt atatatttat ggggtacaat gtcctatttc tgtacatgta 4921 cacattgtgg aatcaaatca ggctaatata tccatcactt catatcatta gcatgaatga 4981 gaacatacaa agccactctt agaaaatttt gaaatttatg ttatttcagc ccttttatgc 5041 tggaggttgc aaatgttttg tgaataatca gaccaaaaat aaaaacaaaa aatgattgac 5101 ttcagtcatt cagtaagaa
```

By "Heterogeneous nuclear ribonucleoprotein A/B (hnRNP A/B) polypeptide" is meant a protein having at least about 85% amino acid identity to the sequence provided at NCBI Reference sequence NP_112556.2, or a fragment thereof and having biological polynucleotide binding activity. As used herein, Hrp48 (also called Hrb27C) is a homolog of the mammalian hnRNP A/B family and implicated in splicing regulation, mRNA localization, and translation. An exemplary hnRNP A/B amino acid sequence is provided below:

Heterogeneous Nuclear Ribonucleoprotein A/B (HNRNP A/B) Isoform A [Homo sapiens]

SEQ ID NO: 11

```
  1 mseageeqpm ettgatengh eavpegespa gagtgaaaga ggataappsg nqngaegdqi 61 naskneedag kmfvgglswd tskkdlkdyf tkfgevvdct ikmdpntgrs rgfgfilfkd 121 aasvekvldq kehrldgrvi dpkkamamkk dpvkkifvgg lnpeateeki reyfgefgei
```

-continued

```
181 eaielpmdpk lnkrrgfvfi tfkeeepvkk vlekkfhtvs gskceikvaq pkevyqqqqy 241 gsggrgnrnr gnrgsggggg gggqsqswnq gygnywnqgy gyqqgygpgy ggydyspygy 301 ygygpgydys qgstnygksq rrgghqnnyk py
```

By "hnRNP A/B polynucleotide" is meant a nucleic acid molecule encoding hnRNP A/B (e.g., heterogeneous nuclear ribonucleoprotein A/B isoform a) An exemplary hnRNP A/B polynucleotide sequence is provided at NCBI Reference Sequence: NM_031266.2, and reproduced herein below.

```
                                                                SEQ ID NO: 12
   1 aaagggcgcc acgagtcggc attgtcaggc ggcggcaccg cgcgggacgg agcttggctg 61 ttggtcggtg ggttcccgtg cggcggcggc caaggaggag gagacacagt tggagcagct 121 ccgtgggctg actggggcga ggcctcagca gcgcgagctt gagtgcggcc gagcctgcgg 181 cgccttcccc tgcgggtggg gacgagcggg ccccgcggcg tcatcggcgg cgaggagccg 241 ccgcgcctcg gcctagcatg tcggaagcgg gcgaggagca gcccatggag acgacgggcg 301 ccaccgagaa cggacatgag gccgtccccg aaggcgagtc gccggccggg gctggcacgg 361 gcgccgcggc gggggctgga ggcgcgaccg cggcgccccc gagcgggaat cagaacggcg 421 ccgagggcga ccagatcaac gccagcaaga acgaggagga cgcgggaaaa atgttcgttg 481 gtggcctgag ctgggatact agcaaaaaag atttaaaaga ctattttact aaatttggag 541 aggtcgttga ctgtacaata aaaatggatc ccaacactgg acggtcaaga gggtttgggt 601 ttatcctgtt caaagatgca gccagtgtgg agaaggtcct agaccagaag gagcacaggc 661 tggatggccg tgtcattgac cctaaaaagg ccatggctat gaagaaggac ccggtgaaga 721 aaatcttcgt tggggggtctg aatcctgaag ccactgagga aaagatcagg gagtactttg 781 gcgagtttgg ggagattgag gccattgaat tgccaatgga tccaaagttg aacaaaagac 841 gaggttttgt gtttatcacc tttaaagaag aagaacccgt gaagaaggtt ctggagaaaa 901 agttccatac tgtcagtgga agcaagtgtg agatcaaggt ggcccagccc aaagaagtct 961 atcagcagca gcagtatggc tctgggggcc gtggaaaccg caaccgaggg aaccgaggca 1021 gcggaggtgg tggtggaggt ggaggtcaga gtcagagttg gaatcagggc tacggcaact 1081 actggaacca gggctacggc taccagcagg gctacgggcc tggctatggc ggctacgact 1141 actcgcccta tggctattac ggctacggcc ccggctacga ctacagtcag ggtagtacaa 1201 actacggcaa gagccagcga cgtggtggcc atcagaataa ctacaagcca tactgaggcg 1261 gcagcaggag cgaccaactg atcgcacaca tgctttgttt ggatatggag tgaacacaat 1321 tatgtaccaa atttaacttg gcaaactttc tattgcctgt cccatgtgca tcttatttaa 1381 aatttccccc atggaaatca ctctcctgtt gactatttcc agagctctag gtgtttaggc 1441 agcgtgtggt gtctgagagg ccatagcgcc atcatgggct gattttttatt accaggtccc 1501 ccagaagcag gtgggaggct ctgcttcctg ctgccgctct gcagcctgga cctgtggacc 1561 ctggttgtaa agagtaaatt gtatcttagg aaaccagtgt caccttttttt tcaccttta 1621 attttatatt atttgcgtca tacatttcct gtaacggaag tgttaatttt actgtacttt 1681 ttggtacctt ttgggaatct aatgtattgt aaggtatttt acacgtgtcc tgattttgcc 1741 acaacctgga tattgaagct atccaagctt ttgaaataaa atttaaaaac ccccaagcct 1801 gggtgagtgt gggataaaaa aaaaaaaaaa aaaaaa
```

By "HuR polypeptide" is meant a protein having at least about 85% amino acid identity to the sequence provided at NCBI Reference sequence NP_001410.2, or a fragment thereof and having polynucleotide binding activity. HuR or "ELAV-like protein 1" is a protein that can contain 3 RNA-binding domains and binds cis-acting AU-rich elements. One of HuR's functions is to stabilize mRNAs in order to regulate gene expression. An exemplary HuR amino acid sequence is provided below:

Elav-Like Protein 1 (Hur) [*Homo sapiens*]

SEQ ID NO: 13

```
  1 msngyedhma edcrgdigrt nlivnylpqn mtqdelrslf ssigevesak lirdkvaghs
 61 lgygfvnyvt akdaeraint lnglrlqskt ikvsyarpss evikdanlyi sglprtmtqk
121 dvedmfsrfg riinsrvlvd qttglsrgva firfdkrsea eeaitsfngh kppgssepit
181 vkfaanpnqn knvallsqly hsparrfggp vhhqaqrfrf spmgvdhmsg lsgvnvpgna
241 ssgwcifiyn lgqdadegil wqmfgpfgav tnvkvirdfn tnkckgfgfv tmtnyeeaam
301 aiaslngyrl gdkilqvsfk tnkshk
```

By "HuR polynucleotide" is meant a nucleic acid molecule encoding a HuR (e.g., ELAV like RNA binding polypeptide 1 (ELAVL1)). An exemplary HuR polynucleotide sequence is provided at NCBI Reference Sequence: NM_001419.2, and reproduced herein below.

SEQ ID NO: 14

```
   1 ggtcgtgcgc gctgaggagg agccgctgcc gccgtcgccg tcgccgccac cgccgccacc
  61 gctaccgagg ccgagcggag ccgttagcgc cgcgccgccg ccgcctcccg cccgcccgg
 121 agcagccccg ggcccgcccg cccgcatcca gatttttgaa aaatacaatg tctaatggtt
 181 atgaagacca catggccgaa gactgcaggg gtgacatcgg agaacgaat ttgatcgtca
 241 actacctccc tcagaacatg acccaggatg agttacgaag cctgttcagc agcattggtg
 301 aagttgaatc tgcaaaactt attcgggata agtagcagg acacagcttg ggctatggct
 361 ttgtgaacta cgtgaccgcg aaggatgcag agagagcgat caacacgctg aacggcttga
 421 ggctccagtc aaaaaccatt aaggtgtcgt atgctcgccc gagctcagag gtgatcaaag
 481 acgccaactt gtacatcagc gggctcccgc ggaccatgac ccagaaggac gtagaagaca
 541 tgttctctcg gtttgggcgg atcatcaact cgcgggtcct cgtggatcag actacaggtt
 601 tgtccagagg ggttgcgttt atccggtttg acaaacggtc ggaggcagaa gaggcaatta
 661 ccagtttcaa tggtcataaa cccccaggtt cctctgagcc catcacagtg aagtttgcag
 721 ccaaccccaa ccagaacaaa aacgtggcac tcctctcgca gctgtaccac tcgccagcgc
 781 gacggttcgg aggccccgtt caccaccagg cgcagagatt caggttctcc cccatgggcg
 841 tcgatcacat gagcgggctc tctggcgtca acgtgccagg aaacgcctcc tccggctggt
 901 gcatttcat ctacaacctg gggcaggatg ccgacgaggg gatcctctgg cagatgtttg
 961 ggccgtttgg tgccgtcacc aatgtgaaag tgatccgcga cttcaacacc aacaagtgca
1021 aagggtttgg ctttgtgacc atgacaaact atgaagaagc cgcgatggcc atagccagcc
1081 tgaacggcta ccgcctgggg gacaaaatct tacaggtttc cttcaaaacc aacaagtccc
1141 acaaataact cgctcatgct ttttttgta cggaatagat aattaagagt gaaggagttg
1201 aaactttct tgttagtgta caactcattt tgcgccaatt ttcacaagtg tttgtctttg
1261 tctgaatgag aagtgagaag gtttttatac tctgggatgc aaccgacatg ttcaaatgtt
1321 tgaaatccca caatgttaga ccaatcttaa gtttcgtaag ttatttcctt taagatatat
1381 attaaacaga aatctaagta gaactgcatt gactaaccag tccctctgga tggtggtgaa
1441 cctgaagcat gctttaacct ctaagactgt ctaacacgcg tttcattcaa tgtctccaca
1501 gactgggtag caaaaaaatc acctttagt tttagttttt aatctaaaga tgttagacag
```

-continued

```
1561  atgctgagtg tgcgttttct caaccgcttc aacattgtaa gcgatgtatg ctttggttga
1621  caggaagttc cttttccagg caggtcccgt tgccacctcc tgctcactca gtcccgggct
1681  ctgccgagtg gtcctgggaa tggcggcggg cccgtccagc gtgggccacc actggggccg
1741  ggggccacgg gctgcatgct gggcgggccc tccagagaag gacacaaacg tgtttcgtaa
1801  gcccaggcac caatgggaat ggaccaaaga gtttcaggga actccagta tattccagag
1861  tcagatctaa gctccaggca cgcctgaaga tgtgttgcta ctctgacatc ccgagtttct
1921  gtccacacat tgcatgcaca gcgccccaca cattggatac tgttgttcac gataatttct
1981  cccgttttcc agagcattta acatagcttg gaggcgtaaa atggctctgt attttaataa
2041  cacagaaaca tttgagcatt gtatttctcg catcccttct cgtgagcgct tagacctttt
2101  tctattttag tcggattttg ttttggaatt ttgcttttgt atgaacactc agcagaaaag
2161  tacttacttc ttgccagtta tctattaacc aaaacctttg atttgtagtt ttaaagatta
2221  accctcaaag ttctcttcat aactgccttg acattttggg ttgttctgtt ctgttaattt
2281  tcttttgctt ttttgtgttt tttgtttgtt tttacttttg catttaagac cattaaattt
2341  gattttgttt tgctcgaatt ttgttttgtt ttttatttta ccttttcttt cttttttggct
2401  agggaaggtg caggtggccc agcattcagg gaggagtcgt aagatcttaa gaaaccaatc
2461  cttgcctcaa gcaaaagcat ttctgaatct gtgacgcaag aatgtgcagt tacaggctgg
2521  tggcttttaa accaggagcc cggaggaagg gtgaaagaga aagcctgtga ataggcagg
2581  gccagatcac ccaaaactcc tcaggactgg gatctggcgt ttataaataa ctagtttaca
2641  gagagaatca caaacaggat aacttagtac cagcagtttt taaccttgac gtgagactaa
2701  aacgtgaccg taggctgttt tttagttatt gctctcatga gatgatggct gtatttatct
2761  gtttatttat acctatttat gtatttattt attgaagtgt gaaattgagc aataggcagg
2821  caccaccgtc cccagagcag gtcagcgtct cgagaggccc ctggacaatt gaggatgccc
2881  atcccctccc ctttccctga tcttttactg aggggctgtg tgcgcgatcc ttgcaaattg
2941  atgatgttgc catccgtacc caggctgtgt ctcataaaag tcggcctggt gccagagagg
3001  acctcctttc tcccacagaa tcccagatcc tcaggaaaag ccaaaaccga ggcccattgc
3061  ccggattcga cacaaaagag ggtccctgct ctgttgcccg agagcagtct gcatcctggg
3121  accagaatgc tttcctggaa aagaagcct ttcaggtttc ctgggccag catcttctga
3181  tggaaggtgg gagccaacac ccttctgatg gaaggtggga gccaacaccc ttctgatgga
3241  aggtgggagc caacacccctt ctgatggaag gtgggagcca acaccttct gatggaaggt
3301  gggagccaac accttctga tggaaggcgg gattcccgct tctgaaactc cccctggagt
3361  ctcactccca cacatgccca tagctagcat tcaacagaga actctgtctt aagcttcaac
3421  tgtgaaaatg atgacgggct tgtagcacct cagcttcttt cctcgccccc ttttatctga
3481  atcctatcaa ttattctgat gctgggacag gtgagaagaa actgtgaagt atatgagcct
3541  ttgaaagttc cctgaagttt ctcagttcag gaacattctc attgtatgtg gtctccgctg
3601  tttgaacagc cttctagcta aaaaattcca aagcctttat ttgggagtct tagcttgcaa
3661  gcttgtggaa ggatttagct taacaactgt cactcctgaa aagcaatctc tgttccatca
3721  aggttctagt tgctggccct gtgtcctcaa agttcattac atcttatcaa ggcctgtttg
3781  caaaggggag atcccttttc ttaaaaaagg ctcaacccaa agaaaccat ttcttaaaaa
3841  atttacata gatcagttgt atttctattt agcaaaaatg agtgctctgc ttttatttgg
3901  gaatttcgat gaaaaagcgt tcagagtaga taatgttcat ttatcaaaaa tctggtttgg
```

-continued

```
3961 gaaataccaa agaggctttg attgaattcc cttttgaccc gtgtgtaact tcctctggta 4021 gttagacccc aggcagctcc gaatttgtga acctgcttcc tgatgaattc tcccttgttc 4081 ccccttggct ctgccattat ttcgttttca gtgtaatttg ccaagccgca gttttctgtg 4141 ctggctgtgc ctctagtcgc agctctgtga ctgattccct cccgggtgct gagtcccctc 4201 cccggccacc atcctgcgtg aatatcctga aattcatggg cttcctcggg ggcccgcccg 4261 caggtggtgc tgggtgggtt ccgccacctt ctcctggaag gtgagccttt tcctggccaa 4321 gggcagctgc cttaacctct gagagtctgc gcttggcctt agtcctggag acccagcctc 4381 cagggactga accgtgctgc tgttgggagc caagaccggc cctttggagc cggcagccca 4441 ggggtccctg ctggatcaga gaaatagaag cacccgaaga cggttagtgg caattccttg 4501 acccggtttg cttccaaatg aaggccattt gtccaccagg cattgaaaag acatgactta 4561 cccagtccgg catcggactt gaaaaatcga aattgacatc actcagctgt tacatttcac 4621 atccgattca gccccttttt atttccatgt gcttttcgca gccttcctgt gttggatgaa 4681 agagaataag aattcagctg acaggaggcc tctatcctgt ccctccaccc caccctccac 4741 ctcaatcccc tcccatcttc cccagaccta cctcacctac taggacctga ggcagctcct 4801 tagcagagac ccctgggggtt tagctgactc tgggggtcag gggttcctgt ccccaaactt 4861 cgcaagacag ccctgaagtc acaagtgctt tcttttaagt ggcattggca attggcgtgt 4921 aatgatggca gtagaatctg aatctcggat cccaggcagg gttcacattt ccaaacccttt 4981 ttgatttccc ctgacctcta atggctggat cctattttc tacaacctt cagtgacatc 5041 gttcaggttt cttcttggc catttaaaaa aacaaatttt ttttttctca cttgtaagtc 5101 accgccagta cctaagttag gctaacggag actttgacag gactggattt ttcttccacc 5161 agaagagaag ccttttccgt tggtttgggg ccacctcttt gaccatgacc atgtgatgtt 5221 ccgtttacag tgacttgctt tgggggaggg gaggctctct taaccgattc ccatgttgta 5281 cagtagatgg ttagaccttt tgtatattag tgtgttttaa gttattgatt tgttttatat 5341 aaaataattt attttttcagg tgccatttt cattttaact ttgttttac atgggtttgt 5401 tttcaataaa gtctgacact ggtgtccaaa agtcaacaat aaaatgaatc ccattgtgtt 5461 cttttgaaga tgcctatgta acttttaagc ttttaaatt attttcagaa aaaaaaaaag 5521 aaaagccctt atcagttttc catcagccca ttgccttttt atttttttt tttaatcctt 5581 gtgaataaat gttctttagt gttttaggag gaaaaagcaa acctagattt tgataaccca 5641 gaagacttca gattaataaa gaagctttga agaagacca ttttcaaaa ttttagtgaa 5701 gtgtgaatat ttttttgtcaa tggctttctc aaagagaatg aaacttttgc accattttca 5761 gagtttttat agagatgcca aattgatata tttacatgta atggaaacat gaaaaagttt 5821 tattaaacaa ttgttcatag ctgtgtagac attttaattc agtttccaaa gctctcaaaa 5881 aatcgtattt ttgaagtacg gagtgatgcg gtttggggcg tggcttacag ttccaacgac 5941 tcaattgtcc cgatactcag ttctttctac aggtatcagg ttcgtgttaa acgctgtatg 6001 ttaactatga ctggaattct gtgatatttt ggtaataaat gaagtgggat cattgcgaaa 6061 aaaaaaaaaa aaaaa
```

By "NonO polypeptide" is meant a protein having at least about 85% amino acid identity to the sequence provided at NCBI Reference sequence CAG33042.1, or a fragment thereof and having polynucleotide binding activity. As used herein, NonA, the *Drosophila* ortholog of mammalian NonO is used to generate a TRIBE fusion polypeptide NonO and NonA are multifunctional proteins involved in the function of nuclear para-speckles as well as other nuclear events like splicing, mRNA export and the regulation of transcription. An exemplary NonO amino acid sequence is provided below:

Nono [*Homo sapiens*]

SEQ ID NO: 15

```
  1 mqsnktfnle kqnhtprkhh qhhhqqqhhq qqqqqppppp ipangqqass qnegltidlk
 61 nfrkpgektf tqrsrlfvgn lppditeeem rklfekygka gevfihkdkg fgfirletrt
121 laeiakveld nmplrgkqlr vrfachsasl tvrnlpqyvs nelleeafsv fgqveravvi
181 vddrgrpsgk givefsgkpa arkaldrcse gsfllttfpr pvtvepmdql ddeeglpekl
241 viknqqfhke reqpprfaqp gsfeyeyamr wkaliemekq qqdqvdrnik eareklemem
301 eaarhehqvm lmrqdlmrrq eelrrmeelh nqevqkrkql elrqeeerrr reeemrrqqe
361 emmrrqqegf kgtfpdareq eirmgqmamg gamginnrga mppapvpagt pappgpatmm
421 pdgtlgltpp tterfgqaat megigaiggt ppafnraapg aefapnkrrr y
```

By "NonO polynucleotide" is meant a nucleic acid molecule encoding a NonO polypeptide. An exemplary NonO polynucleotide sequence is provided at NCBI Reference Sequence: KU178235.1, and reproduced herein below.

SEQ ID NO: 16

```
   1 atgcagagta ataaaacttt taacttggag aagcaaaacc atactccaag aaagcatcat
  61 caacatcacc accagcagca gcaccaccag cagcaacagc agcagccgcc accaccgcca
 121 atacctgcaa atgggcaaca ggccagcagc caaaatgaag gcttgactat tgacctgaag
 181 aattttagaa aaccaggaga aagaccttc acccaacgaa gccgtctttt tgtgggaaat
 241 cttcctcccg acatcactga ggaagaaatg aggaaactat ttgagaaata tggaaaggca
 301 ggcgaagtct tcattcataa ggataaagga tttggcttta tccgcttgga aacccgaacc
 361 ctagcggaga ttgccaaagt ggagctggac aatatgccac tccgtggaaa ccagctgctc
 421 ggaaagctct ggacagatgc agtgaaggct ccttcctgct aaccacattt cctcgtcctg
 481 tgactgtgga gcccatggac cagttagatg atgaagaggg acttccagag aagctggtta
 541 taaaaaacca gcaatttcac aaggaacgag agcagccacc cagatttgca cagcctggct
 601 cctttgagta tgaatatgcc atgcgctgga aggcactcat tgagatggag aagcagcagc
 661 aggaccaagt ggaccgcaac atcaaggagg ctcgtgagaa gctggagatg gagatggaag
 721 ctgcacgcca tgagcaccag gtcatgctaa tgagacagga tttgatgagg cgccaagaag
 781 aacttcggag gatggaagag ctgcacaacc aagaggtgca aaaacgaaag caactggagc
 841 tcaggcagga ggaagagcgc aggcgccgtg aagaagagat gcggcggcag caagaagaaa
 901 tgatgcgcgc acagcaggaa ggattcaagg gaaccttccc tgatgcgaga gagcaggaga
 961 ttcggatggg tcagatggct atgggaggtg ctatgggcat aaacaacaga ggtgccatgc
1021 cccctgctcc tgtgccagct ggtaccccag ctcctccagg acctgccact atgatgccgg
1081 atggaacttt gggattgacc ccaccaacaa ctgaacgctt tggtcaggct gctacaatgg
1141 aaggaattgg ggcaattggt ggaactcctc ctgcattcaa ccgtgcagct cctggagctg
1201 aatttgcccc aaacaaacgt cgccgatac
```

By "Poly(A) binding protein (PABP)" is meant a protein having at least about 85% amino acid identity to the sequence provided at NCBI Reference sequence NP_002559.2, or a fragment thereof and having polynucleotide binding activity. An exemplary PABP amino acid sequence is provided below:

PABP [*Homo sapiens*]

```
                                                       SEQ ID NO: 17
  1 mnpsapsypm aslyvgdlhp dvteamlyek fspagpilsi rvcrdmitrr slgyayvnfq 61 qpadaerald tmnfdvikgk pvrimwsqrd pslrksgvgn ifiknldksi dnkalydtfs 121 afgnilsckv vcdengskgy gfvhfetqea aeraiekmng mllndrkvfv grfksrkere 181 aelgarakef tnvyiknfge dmdderlkdl fgkfgpalsv kvmtdesgks kgfgfvsfer 241 hedaqkavde mngkelngkq iyvgraqkkv erqtelkrkf eqmkqdritr yqgvnlyvkn 301 lddgidderl rkefspfgti tsakvmmegg rskgfgfvcf sspeeatkav temngrivat 361 kplyvalaqr keerqahltn qymqrmasvr avpnpvinpy qpappsgyfm aaipqtqnra 421 ayyppsqiaq lrpsprwtaq garphpfqnm pgairpaapr ppfstmrpas sqvprvmstq 481 rvantstqtm gprpaaaaaa atpavrtvpq ykyaagvrnp qqhlnaqpqv tmqqpavhvq 541 gqepltasml asappqeqkq mlgerlfpli qamhptlagk itgmlleidn sellhmlesp 601 eslrskvdea vavlqahqak eaaqkavnsa tgvptv
```

By "PABP polynucleotide" is meant a nucleic acid molecule encoding a PABP polypeptide. An exemplary PABP polynucleotide sequence is provided at NCBI Reference Sequence: NM_002568.3, and reproduced herein below.

PABP [*Homo sapiens*]

```
                                                       SEQ ID NO: 18
   1 ccctctccc cggcggttag tgctgagagt gcggagtgtg tgctccgggc tcggaacaca 61 catttattat taaaaaatcc aaaaaaaatc taaaaaaatc ttttaaaaaa ccccaaaaaa 121 atttacaaaa aatccgcgtc tccccgccg gagactttta ttttttttct tcctcttttta 181 taaaataacc cggtgaagca gccgagaccg acccgcccgc ccgcggcccc gcagcagctc 241 caagaaggaa ccaagagacc gaggccttcc cgctgcccgg acccgacacc gccaccctcg 301 ctccccgccg gcagccggca gccagcggca gtggatcgac cccgttctgc ggccgttgag 361 tagttttcaa ttccggttga tttttgtccc tctgcgcttg ctccccgctc ccctcccccc 421 ggctccggcc cccagccccg gcactcgctc tcctcctctc acggaaaggt cgcggcctgt 481 ggccctgcgg gcagccgtgc cgagatgaac cccagtgccc ccagctaccc catggcctcg 541 ctctacgtgg gggacctcca ccccgacgtg accgaggcga tgctctacga gaagttcagc 601 ccggccgggc ccatcctctc catccgggtc tgcagggaca tgatcacccg ccgctccttg 661 ggctacgcgt atgtgaactt ccagcagccg gcggacgcgg agcgtgcttt ggacaccatg 721 aattttgatg ttataaaggg caagccagta cgcatcatgt ggtctcagcg tgatccatca 781 cttcgcaaaa gtggagtagg caacatattc attaaaaatc tggacaaatc cattgataat 841 aaagcactgt atgatacatt ttctgctttt ggtaacatcc tttcatgtaa ggtggtttgt 901 gatgaaaatg gttccaaggg ctatggattt gtacactttg agacgcagga agcagctgaa 961 agagctattg aaaaaatgaa tggaatgctc ctaaatgatc gcaaagtatt tgttggacga 1021 tttaagtctc gtaaagaacg agaagctgaa cttggagcta ggcaaaaga attcaccaat 1081 gtttacatca agaattttgg agaagacatg gatgatgagc gccttaagga tctctttggc 1141 aagtttgggc ctgccttaag tgtgaaagta atgactgatg aaagtggaaa atccaaagga
```

-continued

```
1201 tttggatttg taagctttga aaggcatgaa gatgcacaga aagctgtgga tgagatgaac 1261 ggaaaggagc tcaatggaaa acaaatttat gttggtcgag ctcagaaaaa ggtggaacgg 1321 cagacggaac ttaagcgcaa atttgaacag atgaaacaag ataggatcac cagataccag 1381 ggtgttaatc tttatgtgaa aaatcttgat gatggtattg atgatgaacg tctccggaaa 1441 gagttttctc catttggtac aatcactagt gcaaaggtta tgatggaggg tggtcgcagc 1501 aaagggtttg gttttgtatg tttctcctcc ccagaagaag ccactaaagc agttacagaa 1561 atgaacggta gaattgtggc cacaaagcca ttgtatgtag ctttagctca gcgcaaagaa 1621 gagcgccagg ctcacctcac taaccagtat atgcagagaa tggcaagtgt acgagctgtt 1681 cccaaccctg taatcaaccc ctaccagcca gcacctcctt caggttactt catggcagct 1741 atcccacaga ctcagaaccg tgctgcatac tatcctccta gccaaattgc tcaactaaga 1801 ccaagtcctc gctggactgc tcagggtgcc agacctcatc cattccaaaa tatgcccggt 1861 gctatccgcc cagctgctcc tagaccacca tttagtacta tgagaccagc ttcttcacag 1921 gttccacgag tcatgtcaac acagcgtgtt gctaacacat caacacagac aatgggtcca 1981 cgtcctgcag ctgcagccgc tgcagctact cctgctgtcc gcaccgttcc acagtataaa 2041 tatgctgcag gagttcgcaa tcctcagcaa catcttaatg cacagccaca agttacaatg 2101 caacagcctg ctgttcatgt acaaggtcag gaacctttga ctgcttccat gttggcatct 2161 gcccctcctc aagagcaaaa gcaaatgttg ggtgaacggc tgtttcctct tattcaagcc 2221 atgcacccta ctcttgctgg taaaatcact ggcatgttgt tggagattga taattcagaa 2281 cttcttcata tgctcgagtc tccagagtca ctccgttcta aggttgatga agctgtagct 2341 gtactacaag cccaccaagc taaagaggct gcccagaaag cagttaacag tgccaccggt 2401 gttccaactg tttaaaattg atcagggacc atgaaaagaa acttgtgctt caccgaagaa 2461 aaatatctaa acatcgaaaa acttaaatat tatggaaaaa aaacattgca aaatataaaa 2521 taaataaaaa aaggaaagga aactttgaac cttatgtacc gagcaaatgc caggtctagc 2581 aaacataatg ctagtcctag attacttatt gatttaaaaa caaaaaaaca caaaaaaata 2641 gtaaaatata aaaacaaatt aatgttttat agaccctggg aaaaagaatt ttcagcaaag 2701 tacaaaaatt taaagcattc cttcttaa tttgtaatt ctttactgtg aatagctca 2761 gaatgtcagt tctgttttaa gtaacagaat tgataactga gcaaggaaac gtaatttgga 2821 ttataaaatt cttgctttaa taaaaattcc ttaaacagtg aaaaaaaaa
```

By "40S ribosomal protein S2 (Rps2 polypeptide)" is meant a protein having at least about 85% amino acid identity to the sequence provided at NCBI Reference sequence NP_002943.2, or a fragment thereof and having polynucleotide binding activity. An exemplary Rps2 amino acid sequence is provided below:
RPS2 [*Homo sapiens*]

SEQ ID NO: 19
```
  1 maddagaagg pggpggpgmg nrggfrggfg sgirgrgrgr grgrgrgrga rggkaedkew 61 mpvtklgrlv kdmkikslee iylfslpike seiidfflga slkdevlkim pvqkqtragq 121 rtrfkafvai gdynghvglg vkcskevata irgaiilakl sivpvrrgyw gnkigkphtv 181 pckvtgrcgs vlvrlipapr gtgivsapvp kkllmmagid dcytsargct atlgnfakat 241 fdaisktysy ltpdlwketv ftkspyqeft dhlvkthtrv svqrtqapav att
```

By "Rps2 polynucleotide (e.g., 40S ribosomal protein S2)" is meant a nucleic acid molecule encoding a PABP polypeptide. An exemplary Rps2 polynucleotide sequence is provided at NCBI Reference Sequence: NM_002952.3, and reproduced herein below.

RPS2 [*Homo sapiens*]

```
                                                          SEQ ID NO: 20
   1 cttcttttcc gacaaaacac caaatggcgg atgacgccgg tgcagcgggg gggcccgggg 61 gccctggtgg ccctgggatg gggaaccgcg gtggcttccg cggaggtttc ggcagtggca 121 tccggggccg gggtcgcggc cgtggacggg gccggggccg aggccgcgga gctcgcggag 181 gcaaggccga ggataaggag tggatgcccg tcaccaagtt gggccgcttg gtcaaggaca 241 tgaagatcaa gtccctggag gagatctatc tcttctccct gcctattaag gaatcagaga 301 tcattgattt cttcctgggg gcctctctca aggatgaggt tttgaagatt atgccagtgc 361 agaagcagac ccgtgccggc cagcgcacca ggttcaaggc atttgttgct atcgggact 421 acaatggcca cgtcggtctg ggtgttaagt gctccaagga ggtggccacc gccatccgtg 481 gggccatcat cctggccaag ctctccatcg tccccgtgcg cagaggctac tgggggaaca 541 agatcggcaa gccccacact gtcccttgca aggtgacagg ccgctgcggc tctgtgctgg 601 tacgcctcat ccctgcaccc aggggcactg gcatcgtctc cgcacctgtg cctaagaagc 661 tgctcatgat ggctggtatc gatgactgct acacctcagc ccggggctgc actgccaccc 721 tgggcaactt cgccaaggcc acctttgatg ccatttctaa gacctacagc tacctgaccc 781 ccgacctctg gaaggagact gtattcacca agtctcccta tcaggagttc actgaccacc 841 tcgtcaagac ccacaccaga gtctccgtgc agcggactca ggctccagct gtggctacaa 901 cataggggttt ttatacaaga aaaataaagt gaattaagcg tgaaaaaaaa aaaaaaaaa 961 aa
```

By "TAR-DNA binding protein 43 kDa (Tdp43) polypeptide" is meant a protein having at least about 85% amino acid identity to the sequence provided at NCBI Reference Q13148.1, or a fragment thereof and having polynucleotide binding activity. Tdp43 or 'TAR DNA-binding polypeptide 43" is a protein that can act as a transcriptional repressor that binds to chromosomally integrated TAR DNA and represses HIV-1 transcription. TDP-43 has been shown to bind both DNA and RNA and have multiple functions in transcriptional repression, pre-mRNA splicing and translational regulation. An exemplary Tdp43 amino acid sequence is provided below:

TAR DNA-Binding Polypeptide 43 (TDP-43) [*Homo sapiens*]

```
                                                          SEQ ID NO: 21
   1 mseyirvted endepieips eddgtvllst vtaqfpgacg lryrnpvsqc mrgvrlvegi 61 lhapdagwgn lvyvvnypkd nkrkmdetda ssavkvkrav qktsdlivlg lpwktteqdl 121 keyfstfgev lmvqvkkdlk tghskgfgfv rfteyetqvk vmsqrhmidg rwcdcklpns 181 kqsqdeplrs rkvfvgrcte dmtedelref fsqygdvmdv fipkpfrafa fvtfaddqia 241 qslcgedlii kgisvhisna epkhnsnrql ersgrfggnp ggfgnqggfg nsrgggaglg 301 nnqgsnmggg mnfgafsinp ammaaaqaal qsswgmmgml asqqnqsgps gnnqnqgnmq 361 repnqafgsg nnsysgsnsg aaigwgsasn agsgsgfngg fgssmdskss gwgm
```

By "TDP-43 polynucleotide" is meant a nucleic acid molecule encoding a TDP-43 (e.g., TAR DNA-binding polypeptide 43). An exemplary TDP-43 polynucleotide sequence is provided at NCBT Reference Sequence: EF434181.1, and reproduced herein below.

```
                                                           SEQ ID NO: 22
   1 atgtctgaat atattcgggt aaccgaagat gagaacgatg agcccattga ataccatcg 61 gaagacgatg ggacggtgct gctctccacg gttacagccc agtttccagg ggcgtgtggg 121 cttcgctaca ggaatccagt gtctcagtgt atgagaggtg tccggctggt agaaggaatt 181 ctgcatgccc agatgctgg ctggggaaat ctggtgtatg ttgtcaacta tccaaaagat 241 aacaaaagaa aaatggatga cacagatgct tcatcagcag tgaaagtgaa aagagcagtc 301 cagaaaacat ccgatttaat agtgttgggt ctcccatgga aaacaaccga caggacctg 361 aaagagtatt ttagtacctt tggagaagtt cttatggtgc aggtcaagaa agatcttaag 421 actggtcatt caaaggggtt tggctttgtt cgttttacgg aatatgaaac acaagtgaaa 481 gtaatgtcac agcgacatat gatagatgga cgatggtgtg actgcaaact tcctaattct 541 aagcaaagcc aagatgagcc tttgagaagc agaaaagtgt ttgtggggcg ctgtacagag 601 gacatgactg aggatgagct gcgggagttc ttctctcagt acggggatgt gatggatgtc 661 ttcatcccca agccattcag ggcctttgcc tttgttacat ttgcagatga tcagattgcg 721 cagtctcttt gtggagagga cttgatcatt aaaggaatca gcgttcatat atccaatgcc 781 gaacctaagc acaatagcaa tagacagtta gaaagaagtg aagatttgg tggtaatcca 841 ggtggctttg ggaatcaggg tggatttggt aatagcagag ggggtggagc tggtttggga 901 aacaatcaag gtagtaatat gggtggtggg atgaactttg gtgcgttcag cattaatcca 961 gccatgatgg ctgccgccca ggcagcacta cagagcagtt ggggtatgat gggcatgtta 1021 gccagccagc agaaccagtc aggcccatcg ggtaataacc aaaaccaagg caacatgcag 1081 agggagccaa accaggcctt cggttctgga ataactctt atagtggctc taattctggt 1141 gcagcaattg gttggggatc agcatccaat gcagggtcgg gcagtggttt taatggaggc 1201 tttggctcaa gcatggattc taagtcttct ggctggggaa tgaatcacta g
```

By "Zipcode-binding polypeptide 1 (ZBP1) polypeptide" is meant a protein having at least about 85% amino acid identity to the sequence provided at NCBI Reference sequence Q9NZI8.2, or a fragment thereof and having polynucleotide binding activity. ZBP1 is a homolog of the human insulin-like growth factor 2 mRNA-binding polypeptide 1 (IMP-1) and murine CRD-BP, the proteins involved in mRNA transport (RNA-binding proteins, RBPs). An exemplary ZBP1 (IMP-1) amino acid sequence is provided below:

Zipcode-Binding Polypeptide L (ZBP1) Polypeptide Binding Polypeptide (ZBP1) [*Homo sapiens*]

```
                                                           SEQ ID NO: 23
   1 mnklyignln esvtpadlek vfaehkisys gqflvksgya fvdcpdehwa mkaietfsgk 61 velqgkrlei ehsvpkkqrs rkiqirnipp qlrwevldsl laqygtvenc eqvnteseta 121 vvnvtysnre qtrqaimkln ghqlenhalk vsyipdeqia qgpengrrgg fgsrgqprqg 181 spvaagapak qqqvdiplrl lvptqyvgai ikkegatirn itkqtqskid vhrkenagaa 241 ekasivhstp egcssackmi leimhkeakd tktadevplk ilahnnfvgr ligkegrnik 301 kveqdtetki tisslqdltl ynpertitvk gaienccrae qeimkkvrea yendvaamsl 361 qshlipglnl aavglfpass savppppssv tgaapyssfm qapeqemvqv fipaqavgai 421 igkkgqhikq lsrfasasik iappetpdsk vrmviitgpp eaqfkaqgri ygklkeenff 481 gpkeevklet hirvpasaag rvigkggktv nelqnltaae vvvprdqtpd endqivikii 541 ghfyasqmaq rkirdilaqv kqqhqkgqsn qaqarrk
```

By "ZBP1 polynucleotide" is meant a nucleic acid molecule encoding a ZBP1 or insulin-like growth factor 2 mRNA-binding polypeptide 1 polypeptide. An exemplary ZBP1 polynucleotide sequence is provided at NCBI Reference Sequence: AF198254.1, and reproduced herein below.

```
                                                              SEQ ID NO: 24
   1 agaaacgtga cacaccagcc ctctcggagg ggtttcggac cgaagggaag aagctgcgcc 61 gtgtcgtccg tctccctgcg cgccgcgggc acttctcctg ggctctcccc gaactctccc 121 gcgacctctg cgcgccctca ggccgccttc cccgccctgg gctcgggaca acttctgggg 181 tggggtgcaa agaaagtttg cggctcctgc cgccggcctc tccgcctctt ggcctaggag 241 gctcgccgcc cgcgcccgct cgttcggcct tgcccgggac cgcgtcctgc cccgagaccg 301 ccaccatgaa caagctttac atcggcaacc tcaacgagag cgtgacccccc gcggacttgg 361 agaaagtgtt tgcggagcac aagatctcct acagcggcca gttcttggtc aaatccggct 421 acgccttcgt ggactgcccg gacgagcact gggcgatgaa ggccatcgaa actttctccg 481 ggaaagtaga attacaagga aaacgcttag agattgaaca ttcggtgccc aaaaaacaaa 541 ggagccggaa aattcaaatc cgaaatattc caccccagct ccgatgggaa gtactggaca 601 gcctgctggc tcagtatggt acagtagaga actgtgagca agtgaacacc gagagtgaga 661 cggcagtggt gaatgtcacc tattccaacc gggagcagac caggcaagcc atcatgaagc 721 tgaatggcca ccagttggag aaccatgccc tgaaggtctc ctacatcccc gatgagcaga 781 tagcacaggg acctgagaat gggcgccgag ggggctttgg ctctcggggt cagccccgcc 841 agggctcacc tgtggcagcg ggggccccag ccaagcagca gcaagtggac atccccttc 901 ggctcctggt gcccacccag tatgtgggtg ccattattgg caaggagggg gccaccatcc 961 gcaacatcac aaaacagacc cagtccaaga tagacgtgca taggaaggag aacgcaggtg 1021 cagctgaaaa agccatcagt gtgcactcca cccctgaggg ctgctcctcc gcttgtaaga 1081 tgatcttgga gattatgcat aaagaggcta aggacaccaa aacggctgac gaggttcccc 1141 tgaagaccct ggcccataat aactttgtag ggcgtctcat tggcaaggaa ggacggaacc 1201 tgaagaaggt agagcaagat accgagacaa aaatcaccat ctcctcgttg caagaccttta 1261 ccctttacaa ccctgagagg accatcactg tgaaggggc catcgagaat tgttgcaggg 1321 ccgagcagga aataatgaag aaagttcggg aggcctatga gaatgatgtg gctgccatga 1381 gcctgcagtc tcacctgacc cctggcctga acctggctgc tgtaggtctt ttcccagctt 1441 catccagcgc agtcccgccg cctcccagca gcgttactgg ggctgctccc tatagctcct 1501 ttatgcaggc tcccgagcag gagatggtgc aggtgtttat ccccgcccag gcagtgggcg 1561 ccatcatcgg caagaagggg cagcacatca acagctctc ccggtttgcc agcgcctcca 1621 tcaagattgc caccccgaa acacctgact ccaaagttcg tatggttatc atcactggac 1681 cgccagaggc ccaattcaag gctcagggaa gaatctatgg caaactcaag gaggagaact 1741 tctttggtcc caaggaggaa gtgaagctgg agacccacat acgtgtgcca gcatcagcag 1801 ctggccgggt cattggcaaa ggtggaaaaa cggtgaacga gttgcagaat ttgacggcag 1861 ctgaggtggt agtaccaaga gaccagaccc ctgatgagaa cgaccaggtc atcgtgaaaa 1921 tcatcggaca tttctatgcc agtcagatgg ctcaacgaaa gatccgagac atcctggccc 1981 aggttaagca gcagcatcag aagggacaga gtaaccaggc ccaggcacga aggaagtgac 2041 cagcccctcc ctgtcccttc gagtccagga caacaacggg cagaaatcga gagtgtgctc 2101 tccccggcag gcctgagaat gagtgggaat ccgggacacc tgggccggc tgtagatcag 2161 gtttgcccac ttgattgaga aagatgttcc agtgaggaac cctgatctct cagccccaa
```

```
2221  acacctaccc  aattggccca  acactgtctg  cccctcgggg  tgtcagaaat  tctagcgcaa 2281  ggcactttta  aacgtggatt  gtttaaagaa  gctctccagg  ccccaccaag  agggtggatc 2341  acacctcagt  gggaagaaaa  ataaaatttc  cttcaggttt  t
```

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "expression vector" or "recombinant expression vector" is meant a genetically-modified oligonucleotide or polynucleotide construct that permits the expression of an mRNA, protein, polypeptide, or peptide by a host cell, when the construct comprises a nucleotide sequence encoding mRNA, protein, polypeptide, or peptide, and the vector is contacted with the cell under conditions sufficient to have the mRNA, protein, polypeptide, or peptide expressed within the cell. Exemplary expression vectors and methods of construction are described in U.S. Pat. Nos. 8,993,531, 6,136,599, 6,020,164, 5,962,226, 5,858,675, U.S. Patent Application No. 20070066521 and International Application Nos. WO 2012033382, WO 2010075303, which are incorporated herein by reference in their entirety.

The expression vectors of the present invention are not naturally-occurring as a whole. However, parts of the vectors can be naturally-occurring. The expression vectors can comprise any type of polynucleotides, including, but not limited to DNA and RNA, which can be single-stranded or double-stranded, synthesized or obtained in part from natural sources, and which can contain natural, non-natural or altered nucleotides. The expression vectors can comprise naturally-occurring, non-naturally-occurring internucleotide linkages, or both types of linkages. Preferably, the non-naturally occurring or altered nucleotides or internucleotide linkages does not hinder the transcription or replication of the vector.

Recombinant expression vectors of the invention can be any suitable expression vectors, and can be used to transform or transfect any suitable host. Suitable vectors include those designed for propagation and expansion or for expression or both, such as plasmids and viruses. The vector can be, for example, the pUC series (Fermentas Life Sciences, Glen Burnie, MD), the pBluescript series (Stratagene, LaJolla, CA), the pET series (Novagen, Madison, WI), the pGEX series (Pharmacia Biotech, Uppsala, Sweden), and the pEX series (Clontech, Palo Alto, CA). Bacteriophage vectors, such as λGTIO, λGT1 1, λZapII (Stratagene), λEMBL4, and λNM1 149, also can be used. Examples of animal expression vectors include pEUK-C1, pMAM and pMAMneo (Clontech).

The expression vectors of the invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColE1, 2μ plasmid, λ, SV40, bovine papilloma virus, and the like.

The expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the expression vectors include, for example, neomycin/G418 resistance genes, hygromycin resistance genes, histidinol resistance genes, tetracycline resistance genes, and ampicillin resistance genes.

The expression vector can include regulatory sequences, such as transcription and translation initiation and termination codons, which are specific to the type of host (e.g., bacterium, fungus, plant, or mammalian and non-mammalian animals) into which the vector is to be introduced, as appropriate, and taking into consideration whether the vector is DNA- or RNA-based.

The expression vector can include a native or nonnative promoter operably linked to the nucleotide sequence encoding the fusion polypeptide (including functional portions and functional variants thereof), or to the nucleotide sequence which is complementary to or which hybridizes to the nucleotide sequence encoding the fusion polypeptide. The selection of promoters, e.g., strong, weak, inducible, tissue-specific and developmental-specific, is within the ordinary skill of the artisan. Similarly, the combining of a nucleotide sequence with a promoter is also within the skill of the artisan. Promoters of the present invention can be controlled in a constitutive or regulated manner. Such regulated promoters can be inducible or repressible such that expression of the polynucleotide can be enhanced or repressed. Exemplary embodiments can include a non-viral promoter or a viral promoter, for example, the SV40 early promoter, an RSV promoter, the cytomegalovirus (CMV) promoter, the steroid inducible mouse mammary tumor virus (MMTV) promoter, Moloney murine leukemia virus (MMLV) promoter, a promoter found in the long-terminal repeal of the murine stem cell virus, or other suitable systems known in the art.

The expression vectors can be designed for either transient expression, for stable expression, or for both. Furthermore, the recombinant expression vectors can be made for constitutive expression or for inducible expression. Inducible expression systems can be responsive the administration of agents, for example antibiotics and can include systems such as tetracycline regulated expression systems or any inducible expression system known in the art.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300 nucleotides or amino acids.

By "fusion polypeptide" is meant a polypeptide or protein that combines at least two amino acid sequences that are not naturally contiguous.

By "operatively linked" is meant that the two or more polypeptides are connected in manner such that each polypeptide can serve its intended function. Typically, two or more polypeptides are covalently attached through peptide bonds. The fusion polypeptide is preferably produced by standard recombinant DNA techniques. For example, a DNA molecule encoding the first polypeptide is ligated to another DNA molecule encoding the second polypeptide, and the resultant hybrid DNA molecule is expressed in a host cell to produce the fusion polypeptide. The DNA molecules are ligated to each other in a 5' to 3' orientation such that, after ligation, the translational frame of the encoded polypeptides is not altered (e.g., the DNA molecules are ligated to each other in-frame).

The invention further provides a host cell comprising any of the recombinant expression vectors described herein.

By "host cell" is meant any type of cell that can contain the recombinant expression vectors of the present invention. The host cell can be a eukaryotic cell, (e.g., plant, animal, fungi, or algae), or can be a prokaryotic cell (e.g., bacteria or protozoa). The host cell can be a cultured cell or a primary cell e.g., isolated directly from an organism, e.g., a human. The host cell can be an adherent cell or a suspended cell, i.e., a cell that grows in suspension. Host cells useful according to the methods of this invention are well known in the art. Suitable host cells can include, for example, *Drosophila* Schneider 2 (S2) cells, Chinese Hamster Ovary (CHO) cells; HeLa cells; liver cells; CV-1 cells; P19 cells; NT2/D1 cells; mouse L cells; African Green monkey kidney cells (e.g., COS-7 cells or other COS cells); human embryonic kidney cells (e.g., HEK 293; DG44 cells), ltk-cells, mouse NIH 3T3 cells and yeast cells. The host cells can be transiently transfected or stably transformed cell lines. Additional host cells can be mammalian cells, for example, adipocytes, bone marrow derived cells, epidermal cells, endothelial cells, fibroblasts, hematopoietic cells, hepatocytes, myocytes, neurons, pancreatic cells, and their progenitor cells or stem cells.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "operably linked" is meant that a first polynucleotide is positioned adjacent to a second polynucleotide that directs transcription of the first polynucleotide when appropriate molecules (e.g., transcriptional activator proteins) are bound to the second polynucleotide.

By "plasmid" is meant a plasmid vector, e.g., circular polynucleotide sequences that are capable of autonomous replication within a suitable host cell due to an origin of replication ("ORI"). Furthermore, a plasmid may comprise a selectable marker to indicate the success of the transformation or other procedures meant to introduce foreign DNA into a cell and a multiple cloning site which includes multiple restriction enzyme consensus sites to enable the insertion of an insert. Plasmid vectors can be referred to as cloning or donor vectors are used to ease the cloning and to amplify a sequence of interest. Plasmid vectors called expression or acceptor vectors are specifically for the expression of a gene of interest in a defined target cell. Those plasmid vectors generally show an expression cassette, consisting of a promoter, the transgene and a terminator sequence. Expression plasmids can be shuttle plasmids containing elements that enable the propagation and selection in different host cells.

By "polypeptide" is meant any chain of amino acids, regardless of length or post-translational modification.

By "positioned for expression" is meant that the polynucleotide of the invention (e.g., a DNA molecule) is positioned adjacent to a DNA sequence that directs transcription and translation of the sequence (e.g., facilitates the production of, for example, a recombinant polypeptide of the invention, or an RNA molecule).

By "promoter" is meant a polynucleotide sufficient to direct transcription. As used herein, a promoter refers to a polynucleotide that directs transcription of a segment of a polynucleotide to which it is operatively linked. The promoter can include specific sequences that are sufficient for RNA polymerase recognition, binding and transcription initiation. In addition, the promoter region includes sequences that modulate transcription initiation, such as cis acting elements which may be responsive to trans acting factors. Exemplary promoters include nucleic acid sequences of lengths 100, 250, 300, 400, 500, 750, 900, 1000, 1250, and 1500 nucleotides that are upstream (e.g., immediately upstream) of the translation start site.

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "specifically binds" is meant a protein that recognizes and binds a polynucleotide of interest, but which does not substantially recognize and bind other molecules in a sample, for example, a biological sample.

Nucleic acid molecules useful in the methods of the invention include any nucleic acid molecule that encodes a polypeptide of the invention or a fragment thereof Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule.

By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, AR. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those of ordinary skill in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μ/ml denatured salmon sperm DNA (ssDNA).

In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those of ordinary skill in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those of ordinary skill in the art. Hybridization techniques are well known to those of ordinary skill in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity lo a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1A provides a schematic depicting the TRIBE technique, which identifies the target binding transcripts of specific RNA-binding proteins (RBPs).

FIG. 1B provides a schematic depicting a native *drosophila* ADAR composed of two double-stranded RNA-binding domains (dsRBDs) that mediate its target specificity and a deaminase domain that catalyzes an adenosine-to-inosine conversion.

FIG. 1C provides a schematic depicting the dsRBDs of ADAR were replaced with the RBP of interest. The editing specificity of the fusion polypeptide was determined by the RNA recognition features of the RBP, and the target transcript was permanently marked by a novel editing event.

FIG. 1D provides a schematic depicting the cell-specific expression of the fusion polypeptide, which will allow identification of targets in discrete populations of cells in vivo. Co-expression of a fluorescent protein allows for enrichment of RNA from the cells of interest. Examples of *Drosophila* neuronal subsets examined here were the core circadian pacemaker neurons (pdf (pdf-Gal4) expressing, ~16 cell/brain) and dopaminergic neurons (tyrosine hydroxylase (TH-Gal4), expressing, ~1,000 cells/brain).

FIG. 2A provides a graph indicating an increase in A to G editing events was observed upon induction of the fusion polypeptide in S2 cells. No increase in editing sites was observed when an ADAR catalytic domain alone was expressed or when Hrp48mut-ADARcd (Hrp48 with mutated RNA-binding domains) was expressed.

FIGS. 2B-2D show the same genes and the same sites were reproducibly edited across biological replicates at similar efficiencies (FIG. 2B, inset, and FIG. 2C).

FIG. 2B provides a frequency histogram of the number of edits per target genes, indicating that most genes have only one editing site, but the TRIBE protein has strong specificity for certain sites.

FIG. 2C provides a graph indicating a correlation between the TRIBE protein sites (Hrp48 ADARcd Repeat 1 and Repeat 2) that were edited to a similar degree between biological repeats ($R^2=0.859$).

FIG. 2D provides an editing event map indicating endogenous and fusion polypeptides have similar binding patterns and TRIBE editing reflects the pattern of the CLIP signal. An example gene, Lam, showing mRNA expression and CLIP signal (top three panels) and editing tracks for wild-type cells, stable cells lines (Hrp48-TRIBE), with and without induction of expression of the fusion polypeptide. Editing events are indicated by black bars, and the height of the bar indicates the percentage editing at that site.

FIG. 4A provides a graph indicating both CLIP signal and editing sites were enriched in the 30 UTR. Metagene quantification of the location of either CLIP peaks or TRIBE edits. The background indicates the proportion of the fly transcriptome composed of the indicated regions.

FIG. 4B provides a graph indicating the majority of TRIBE editing sites were near the CLIP peaks. The fraction of editing sites within a certain distance of a CLIP peak was quantified for both endogenous Hrp48 and Hrp48-TRIBE. A distance of 0 bp indicates that the editing site was within the bounds of a CLIP peak.

FIG. 4C provides a Venn diagram indicating TRIBE targets were a subset of CLIP targets. The Venn diagram shows overlap of genes between all expressed genes, all TRIBE target genes, and all genes with at least one statistically significant CLIP peak FIG. 4D provides a graph indicating that TRIBE targets were more CLIP enriched. Frequency distribution of per gene CLIP enrichments of all CLIP target genes and TRIBE genes that have CLIP signal. The overlap between the top 25% ranked CLIP targets and TRIBE targets are inset.

FIGS. 5A-5C provide schematics indicating significant motifs found by MEME analysis. Motifs found by in vitro selection (SELEX; Blanchette et al) or CLIP (endogenous Hrp48 and Hrp48-ADARcd). SEQ ID NOs. 25-30, in order of appearance.

FIG. 5D and FIG. 5E provide schematics indicating motifs found in regions surrounding Hrp-ADARcd TRIBE editing sites. For Hrp48-ADARcd TRIBE editing events in S2 cells, an area ±20 and 100 bp around the edited base was used for analysis (FDR<0.001). SEQ ID NOs. 31-37 in order of appearance.

FIG. 6A provides a graph indicating the predicted double-strandedness around TRIBE editing sites (light gray, circle) or CLIP binding sites that lack TRIBE editing sites (dark gray, square). Single nucleotide resolution for Hrp48 binding location was achieved by performing CIMS analysis (crosslinking induced mutation site) on CLIP data. A flanking region of 250 nt both 50 and 30 of the site (501 nt in total) was folded with UNAFold, base pairing was counted in the predicted minimum free energy (MFE) and suboptimal structures (within DDG=5 Kcal/mol of the MFE), and the profile is averaged per. All sites were then averaged to yield this plot (mean±SEM, n=17 TRIBE editing sites). Data was obtained from Hrp48 TRIBE.

FIG. 6B provides a schematic showing a RNA structure around the sites edited by the catalytic domain of human ADAR2 in yeast that resembles the intermediate complex formed when ADAR2 distorts local dsRNA and the sequences flanking the edited adenosine are optimal for deaminase domain binding.

FIG. 7A provides a graph indicating the dFMR1-TRIBE protein retains deaminase activity, an increase in A to G editing events was observed upon induction of the fusion polypeptide in S2 cells.

FIGS. 7B and 7C show the same genes and the same sites are reproducibly edited across biological replicates at similar efficiencies.

FIG. 7B provides a frequency histogram of the number of edits per target genes indicating that most genes have only one editing site, but the TRIBE protein has strong specificity for certain sites.

FIG. 7C provides a graph indicating the TRIBE sites are edited to a similar degree between biological repeats ($R^2$=0.86).

FIG. 7D provides an editing event map indicating an example gene, poe, showing mRNA expression (top), and editing tracks for stable cells lines (dFMR1-TRIBE), with and without induction of expression of the fusion polypeptide. Editing events are indicated by black bars, and the height of the bar indicates the percentage editing at that site.

FIG. 7E provides a graph of a Metagene quantification of the location of either CLIP peaks or TRIBE edits. The background indicates the proportion of the fly transcriptome composed of the indicated regions. Intronic sites were excluded from the analysis to allow direct comparison to known mouse FMRP CLIP data from Darnell et al. (2011).

FIG. 8A provides a graph indicating mouse homologs of dFMR1-TRIBE targets in S2 cells were enriched for higher CLIP ranking targets of FMRP.

FIG. 8B provides a graph indicating the mouse homologs of neuronal dFMR1 TRIBE targets were enriched for higher CLIP rankings.

FIG. 8C provides a Venn diagram showing approximately 50% of the fly homologs of robust mouse brain FMRP CLIP targets were also TRIBE targets in excitatory fly neurons (Cha). Mouse FMRP CLIP data was obtained from Darnell et al., 2011.

FIG. 9A provides a graph indicating the NonA-TRIBE protein retains deaminase activity. An increase in A to G editing events was observed upon induction of the fusion polypeptide in S2 cells. NonA TRIBE induces very few sites in mRNA, but many sites were present in nascently transcribed RNA.

FIGS. 9B and 9C provide frequency histograms of the number of edits per target genes show that most genes have only one editing site in mRNA (FIG. 9B), but in nascent RNA (FIG. 9C) many genes have many more edits (median=2, 75th percentile=6, maximum=181 edits per gene).

FIG. 9D provides an editing event map for an example gene, Dscam, indicating mRNA (top) and nascent RNA (middle) expression and editing tracks with and without induction of expression of the fusion polypeptide. Editing events are indicated by black bars, and the height of the bar indicates the percentage editing at that site. The full annotation of Dscam is shown above two example splice variants likely expressed in these S2 cells (bottom).

FIG. 9E provides a graph indicating Metagene quantification of the location of TRIBE edits (NonA-TRIBE and Hrp48-TRIBE) in both mRNA and nascent RNA. The total number of editing sites was marked next to the bars. The background indicates the proportion of the fly transcriptome composed of the indicated regions.

FIG. 10A provides a graph indicating the number of editing sites detected in S2 cells expressing Hrp48 TRIBE at different sequencing depths (million mapped reads), employing different coverage thresholds for the identification of an editing sites. The more stringent threshold of 20 reads was used throughout this study.

FIG. 10B provides a graph indicating the number of editing sites detected in S2 cells expressing different RBP TRIBE constructs. The number of sites for a given sequencing depth differs by RBP (data for 20 read threshold editing sites is shown).

FIG. 11A provides a graph indicating a modest increase in A to G editing events was observed in mRNA upon induction of the fusion polypeptide in S2 cells (data also shown, along with nascent RNA in FIG. 13A).

FIG. 11B provides a graph indicating the editing percentage is correlated at given sites between biological repeats ($R^2=0.88$)

FIG. 11C provides a Venn diagram indicating the classification of editing sites based on RefSeq annotation. Most 'intronic' sites are not also annotated as exonic, e.g., most mRNA NonA intronic sites are not a mis-categorization, the sites are actually in introns that are found in the mRNA fraction.

FIG. 11D provides a TRIBE editing map of an example gene, ppn, which has many NonA-TRIBE editing events in an intronic region. The intronic region was clearly expressed in the mRNA, as well as the nascent RNA fraction, and was identified as a binding target in both.

FIG. 12A provides a graph indicating the number of editing sites detected in RNA isolated from specific subsets of neurons expressing the Hrp48-TRIBE protein (the bars labeled TRIBE) were significantly greater than the background number of endogenous editing sites (the bars labeled control). The core circadian pdf neuropeptide-expressing cells (pdf-Gal4), dopaminergic neurons (TH-Gal4) and generic neurons (elav-Gal4) were the cell types examined.

FIG. 12B provides a Venn diagram of the genes that are identified as Hrp48 targets by TRIBE in different cell types.

FIGS. 12C-12E show schematics of example genes from three categories of target genes.

FIG. 12C is a map indicating many commonly expressed genes are identified as targets in each of the three cell types.

FIGS. 12D and 12E show data indicating some genes are identified as targets in only one (or a combination of two) cell types.

FIG. 12D shows data indicating genes that are expressed only in certain cell types are identified as targets and (FIG. 12E) commonly expressed genes may be identified as a target in one cell type and not the others (dashed insets in FIG. 12B). Note that here "expression" was classified as sufficient sequencing depth at the editing site location, and, as such, the number of cell-specifically expressed genes was likely an overestimation.

FIGS. 12C-12E show the tracks include RNA-Seq and Hrp48 CLIP from whole fly heads, RNA-Seq, and Hrp48-TR1BE editing tracks from the indicated isolated neuron subtype, either GFP-expressing control (labeled pdf, TH, and elav) or Hrp48-TRIBE-expressing cells (labeled pdf, TH, and elav-TRIBE). Editing events are indicated by black bars, and the height of the bar indicates the percentage editing at that site. The scale for mRNA-Seq was constant for each gene, resulting in truncation of signal of pdf in pdf cells.

FIG. 13B provides frequency histograms of the number of edits per target genes (Left graph; Cha. Right graph; GAD).

FIG. 13C provides a Venn diagram of the genes identified as dFMR1 targets by TRIBE in different cell types. Target editing sites that have sufficient sequencing depth in both cell types are outlined with a dashed line.

FIGS. 13D-13F show binding maps of example genes.

FIG. 13E shows many commonly expressed genes are identified as targets in each of the both cell types, and some genes as shown in FIGS. 13D and 13F are identified as targets in either one or the other cell type, despite being expressed in both. Tracks are RNA-Seq and dFMR1-ADARcd TRIBE editing tracks from the indicated isolated neuron subtype, either GFP-expressing control or dFMR1-ADARcd-expressing cells. Editing events are indicated by black bars, and the height of the bar indicates the percentage editing at that site.

FIG. 14A provides a graph indicating the nearest neighbor preference for three TRIBE proteins (in S2 cells).

FIG. 14B provides a graph indicating the nearest neighbor preference for editing sites of different editing percentages for Hrp48-ADARcd (in S2 cells). The use of "n" indicates the number of sites used.

FIG. 15H provides graphs indicating the number of edited sites for the PABP-E488Q mutant fusion polypeptide (left panel) and Rps2-E488Q mutant fusion polypeptide (right panel).

FIG. 16 provides a table of the gene ontology (GO) analysis of common targets of 4E-BP of 4E-BP in rapamycin and torin 1 treatment conditions.

DETAILED DESCRIPTION OF THE INVENTION

Figure 1A:
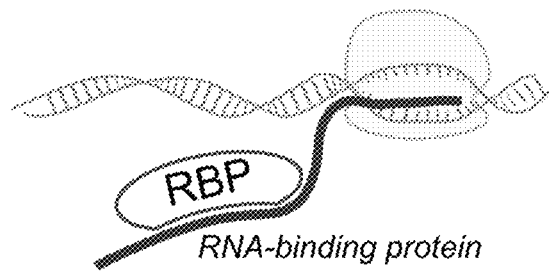
FIGS. 1A-1D show schematic representations of TRIBE, a fusion polypeptide of an RNA-binding polypeptide (RBP) and the catalytic domain of Adenosine Deaminases Acting on RNA (ADAR) that can edit target transcripts of the RNA-Binding Protein.
Figure 1B:
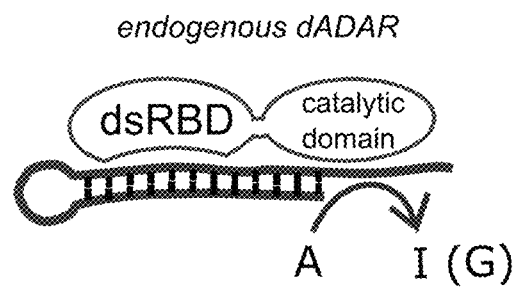
Figure 1C:
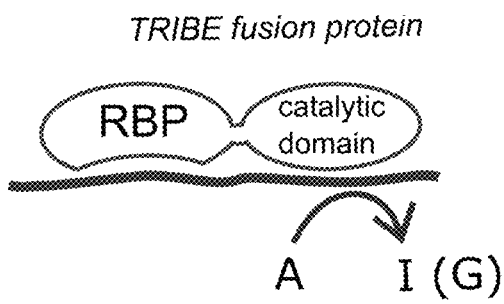
Figure 1D:
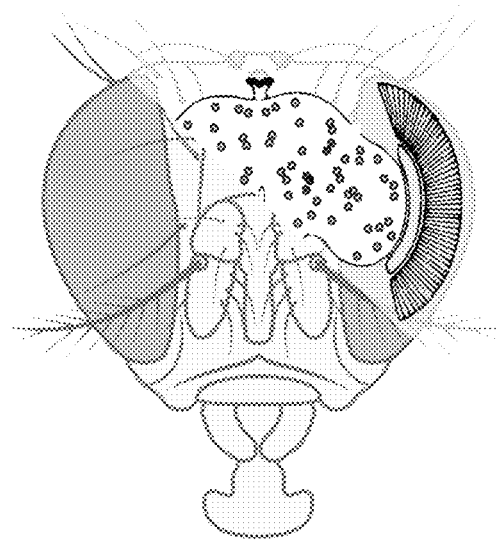

The invention features compositions and methods that are useful for identifying the functional targets of RNA binding proteins (RBPs). RNA transcripts are bound and regulated by RNA-binding proteins (RBPs). Current methods for identifying in vivo targets of an RBP are imperfect and not amenable to examining small numbers of cells.

To address these issues, the present invention uses a TRIBE (targets of RNA-binding proteins identified by editing) system, a method that couples an RBP to the catalytic domain of the Drosophila RNA-editing enzyme Adenosine deaminases acting on RNA (ADAR) and expresses the fusion polypeptide in vivo. RBP targets are marked with novel RNA editing events and identified by sequencing RNA TRIBE has been used to identify the targets of three RBPs (Hrp48, dFMR1, and NonA). TRIBE compares favorably to other methods, including CLIP, and TRIBE has identified RBP targets from as little as 150 specific fly neurons. TRIBE can be performed without an antibody and in small numbers of specific cells.

The invention further provides methods for expressing RNA binding protein-RNA modifying enzyme fusion polypeptides in a cell, tissue, or organ that does not typically express such proteins. If desired, a viral vector (e.g., an adeno-associated viral vector) is used to express a RNA binding protein-RNA modifying enzyme fusion polypeptide. Such viral vectors may, if desired, be administered in combination with fusion polypeptides of the invention. Advantageously, the fusion polypeptides containing a RNA binding protein-RNA modifying enzyme fusion polypeptide are only transiently present in the cell, while the polypeptide or fusion polypeptide expressed in the adeno-associated viral vector are persistently expressed. If desired, the expression of a RNA binding protein-RNA modifying enzyme fusion polypeptide can persist, for constitutive expression.

Recombinant Polypeptide Expression

The invention generally provides an RNA binding polypeptide operably linked to a RNA modifying enzyme, where the RNA binding polypeptide is capable of specifically binding and editing an RBP target. The target is irreversibly marked by this editing. The transcriptome of cells of interest is subsequently sequenced, thereby identifying the RBP target.

As described in more detail below, virtually any RNA binding polypeptide of interest can be fused to a RNA modifying enzyme to form an RNA binding protein-RNA modifying enzyme fusion polypeptide. Advantageously, such fusion polypeptides can be delivered to cells in vitro or in vivo. In one embodiment, a fusion polypeptide of the invention is used to contact a cell in vitro, such that the cell takes up the fusion polypeptide. Alternatively, a fusion polypeptide of the invention is delivered to a cell, tissue, or organ in situ, such that the cell, tissue, or organ takes up the fusion polypeptide.

In embodiments of the present invention various RNA binding proteins of interest can be fused to a RNA modifying enzyme to form an RNA binding protein-RNA modifying enzyme fusion polypeptide. RNA binding proteins can include, for example, Eukaryotic translation initiation factor 4E-binding polypeptide 1 (eIF4EBP1), fragile X mental retardation protein 1 (FMRP1), dFMR1 (Drosophila melanogaster homolog of the fragile X mental retardation protein), RNA-binding polypeptide FUS, ELAV-like protein 1 (HuR), Hrp48 (also called Hrb27C), hnRNP A/B, NonA, NonO, TAR DNA-binding polypeptide 43 (TDP-43) and Zipcode-binding polypeptide 1 (ZBP1)

In embodiments of the present invention various RNA modifying enzymes can be operatively linked to the RNA binding proteins to form an RNA binding protein-RNA modifying enzyme fusion polypeptide. RNA modifying enzymes can include, for example, adenosine deaminase such as Adenosine deaminases that act on RNA (ADARs) and any cytidine deaminase enzyme.

Adenosine deaminases that act on RNA (ADARs) deaminate adenosines in dsRNA to produce inosines ADARs are important in mammals and are particularly important in the nervous system.

Recombinant fusion polypeptides of the invention are produced using virtually any method known to the skilled artisan. Typically, recombinant polypeptides are produced by transformation of a suitable host cell with all or part of a polypeptide-encoding nucleic acid molecule or fragment thereof in a suitable expression vehicle. Those skilled in the field of molecular biology will understand that any of a wide variety of expression systems may be used to provide the recombinant protein. The precise host cell used is not critical to the invention. A polypeptide of the invention may be produced in a prokaryotic host (e.g., E. coli) or in a eukaryotic host (e.g., Saccharomyces cerevisiae, insect cells, e.g., Sf21 cells, or mammalian cells, e.g., NIH 3T3, HeLa, or preferably COS cells). Such cells are available from a wide range of sources (e.g., the American Type Culture Collection, Rockland, Md.; also, see, e.g., Ausubel et al., Current Protocol in Molecular Biology, New York: John Wiley and Sons, 1997). The method of transformation or transfection and the choice of expression vehicle will depend on the host system selected. Transformation and transfection methods are described, e.g., in Ausubel et al. (supra); expression vehicles may be chosen from those provided, e.g., in Cloning Vectors: A Laboratory Manual (P. H. Pouwels et al., 1985, Supp. 1987).

A variety of expression systems exist for the production of the polypeptides of the invention. Expression vectors useful for producing such polypeptides include, without limitation, chromosomal, episomal, and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof.

One particular bacterial expression system for polypeptide production is the E. coli pET expression system (e.g., pET-28) (Novagen, Inc., Madison, Wisc.). According to this expression system, DNA encoding a polypeptide is inserted into a pET vector in an orientation designed to allow expression. Since the gene encoding such a polypeptide is under the control of the T7 regulatory signals, expression of the polypeptide is achieved by inducing the expression of T7 RNA polymerase in the host cell. This is typically achieved using host strains that express T7 RNA polymerase in response to IPTG induction. Once produced, recombinant polypeptide is then isolated according to standard methods known in the art, for example, those described herein.

Another bacterial expression system for polypeptide production is the pGEX expression system (Pharmacia). This system employs a GST gene fusion system that is designed for high-level expression of genes or gene fragments as fusion polypeptides with rapid purification and recovery of functional gene products. The protein of interest is fused to the carboxyl terminus of the glutathione S-transferase protein from Schistosoma japonicum and is readily purified from bacterial lysates by affinity chromatography using Glutathione Sepharose™ 4B. Fusion polypeptides can be recovered under mild conditions by elution with glutathione. Cleavage of the glutathione S-transferase domain from the fusion polypeptide is facilitated by the presence of recognition sites for site-specific proteases upstream of this domain. For example, proteins expressed in pGEX-2T plasmids may be cleaved with thrombin; those expressed in pGEX-3X may be cleaved with factor Xa.

Alternatively, recombinant polypeptides of the invention are expressed in *Pichia pastoris*, a methylotrophic yeast. *Pichia* is capable of metabolizing methanol as the sole carbon source. The first step in the metabolism of methanol is the oxidation of methanol to formaldehyde by the enzyme, alcohol oxidase. Expression of this enzyme, which is coded for by the AOX1 gene is induced by methanol. The AOX1 promoter can be used for inducible polypeptide expression or the GAP promoter for constitutive expression of a gene of interest.

Once the recombinant polypeptide of the invention is expressed, it is isolated, for example, using affinity chromatography. Recombinant polypeptides expressed in the selected host cell can be separated, isolated, and purified using conventional biochemical techniques, for example, treatment with a protein precipitating agent (salting out method), centrifugation, ultrasonic disruption, ultrafiltration, dialysis, molecular sieve chromatography, gel filtration, adsorption chromatography, ion exchange chromatography, affinity chromatography, and the like can be used, such as various types of chromatography, and combinations thereof commonly used to separate the high purity protein.

In one example, an antibody raised against a polypeptide of the invention may be attached to a column and used to isolate the recombinant polypeptide. An antibody can be produced by any antibody production method generally known in the art. For example, an antibody may be produced from a B cell hybridoma cell line produced by a mammalian such as Chinese hamster ovary (CHO) cell line. As one of ordinary skill in the art would understand, the heavy chain C-terminal lysine can be absent from the version produced by CHO cells (Dick Jr. et al., Biotechnol. Bioeng. 2008; 100: 1132-1143). Further exemplary methods of antibody generation are described by U.S. Pat. Nos. 6,794,500, 7,432, 367, U.S. Patent Application No. 20150266975 and International Patent Application Nos. WO 1998023744, WO 2010075303, WO 2015085003, which are incorporated herein by reference in their entirety. Lysis and fractionation of polypeptide-harboring cells prior to affinity chromatography may be performed by standard methods (see, e.g., Ausubel et al., supra). Alternatively, the polypeptide is isolated using a sequence tag, such as a hexahistidine tag, that binds to nickel column.

Once isolated, the recombinant protein can, if desired, be further purified, e.g., by high performance liquid chromatography (see, e.g., Fisher, Laboratory Techniques In Biochemistry and Molecular Biology, eds., Work and Burdon, Elsevier, 1980). Polypeptides of the invention, particularly short peptide fragments, can also be produced by chemical synthesis (e.g., by the methods described in Solid Phase Peptide Synthesis, 2nd ed., 1984 The Pierce Chemical Co., Rockford, Ill.). These general techniques of polypeptide expression and purification can also be used to produce and isolate useful peptide fragments or analogs (described herein).

RNA Binding Protein-RNA Modifying Enzyme Fusion Polypeptide and Analogs

Also included in the invention are RNA binding protein-RNA modifying enzyme fusion polypeptides or fragments thereof that are modified in ways that enhance their ability to identify targets. The invention provides methods for optimizing a RNA binding protein-RNA modifying enzyme fusion polypeptide amino acid sequence or nucleic acid sequence by producing an alteration in the sequence. Such alterations may include certain mutations, deletions, insertions, or post-translational modifications. The invention further includes analogs of any naturally-occurring polypeptide of the invention. Analogs can differ from a naturally-occurring polypeptide of the invention by amino acid sequence differences, by post-translational modifications, or by both. Analogs of the invention will generally exhibit at least 85%, more preferably 90%, and most preferably 95% or even 99% identity with all or part of a naturally-occurring amino, acid sequence of the invention. The length of sequence comparison is at least 5, 10, 15 or 20 amino acid residues, preferably at least 25, 50, or 75 amino acid residues, and more preferably more than 100 amino acid residues. Again, in an exemplary approach to determining the degree of identity, a BLAST program may be used, with a probability score between e-3 and e-100 indicating a closely related sequence.

The nucleic acid and protein sequences of the present invention can further be used as a "query sequence" to perform a search against public databases to, for example, identify related sequences. Such searches can be performed using the NBLAST and XBLAST programs (version 2.0) of Altschul, et al., J. Mol. Biol. 215:403-10 (1990). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., Nucleic Acids Res. 25(17):3389-3402 (1997) When utilizing BLAST and Gapped BLAST programs, the default parameters of the respective programs (e.g., XBLAST and NBLAST) can be used (See www.ncbi.nlm.nih.gov).

Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring polypeptides of the invention by alterations in primary sequence. These include genetic variants, both natural and induced (for example, resulting from random mutagenesis by irradiation or exposure to ethane methylsulfate or by site-specific mutagenesis as described in Sambrook, Fritsch and Maniatis, Molecular Cloning: A Laboratory Manual (2d ed.), CSH Press, 1989, or Ausubel et al., supra). Also included are cyclized peptides, molecules, and analogs which contain residues other than L-amino acids, e.g., D-amino acids or non-naturally occurring or synthetic amino acids, (e.g., beta or gamma amino acids).

In addition to full-length polypeptides, the invention also provides fragments of any one of the polypeptides or peptide domains of the invention. As used herein, the term "a fragment" means at least 5, 10, 13, or 15 amino acids. In other embodiments a fragment is at least 20 contiguous amino acids, at least 30 contiguous amino acids, or at least 50 contiguous amino acids, and in other embodiments at least 60 to 80, 100, 200, 300 or more contiguous amino acids. Fragments of the invention can be generated by methods known to those of ordinary skill in the art or may result from normal protein processing (e.g., removal of amino acids from the nascent polypeptide that are not required for biological activity or removal of amino acids by alternative mRNA splicing or alternative protein processing events).

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

TRIBE involves the fusion of an RBP to the catalytic domain of an RNA-editing enzyme (ADARcd). Because the double-stranded RNA-binding (dsRBD) regions of ADAR are missing from the fusion protein, its editing specificity was determined by the RNA recognition features of the RBP; target transcripts are edited in vivo and then identified by RNA sequencing (FIG. 1). TRIBE is compatible with cell culture but also applicable to the identification of cell-specific RBP targets. For example, purification and sequencing of RNA from specific cells, achieved by co-expression of fluorescent protein and fluorescence-activated cell sorting or manual cell-sorting, allows for the identification of targets in tiny numbers of neurons (see below).

Example 1: The HRP48-Tribe Fusion Polypeptide has Editing Activity and HRP48-Determined Specificity Hrp48 (also called Hrb27C) is a homolog of the mammalian hnRNP A/B family and implicated in splicing regulation, mRNA localization, and translation. Hrp48 was chosen as an initial RBP because it has well-characterized targets, there is an excellent antibody, and preliminary data indicated that it participates in circadian regulation.

Figure 2A:
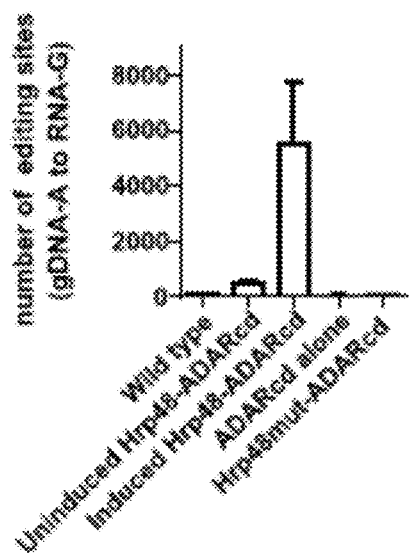
FIGS. 2A-2D show the ability of TRIBE fusion polypeptide to reproducibly edit certain sites.

Initial experiments were performed by creating stable *Drosophila* S2 cell lines that express the Hrp48-ADARcd fusion polypeptide (henceforth referred to as Hrp48-TRIBE) under inducible control. Expression of this protein in S2 cells, which have extremely low levels of endogenous editing, lead to a dramatic increase in the number of detected editing events (approximately 20-fold; FIG. 2A) They are confined to the correct base conversion, A to G, indicating that the fusion polypeptide was catalyzing the appropriate deamination reaction. Induction of the ADAR catalytic domain alone results in no increase in editing sites despite stable protein expression (FIG. 2A). Similarly, Hrp48-TRIBE with mutated Hrp48 RNA-binding domains is stably expressed and also causes no increase in editing sites, indicating a requirement for the RNA-binding ability of Hrp48 (FIG. 2A).

Figure 2B:
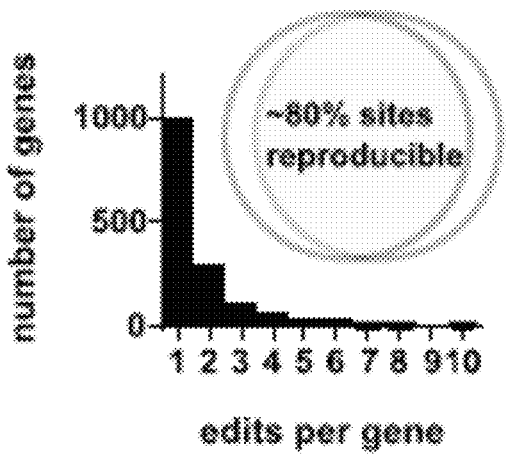
Figure 2C:
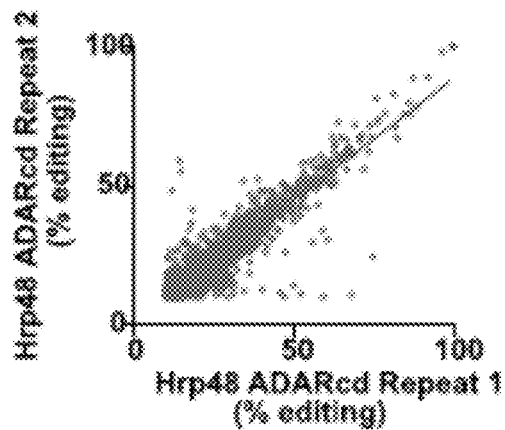
Figure 2D:
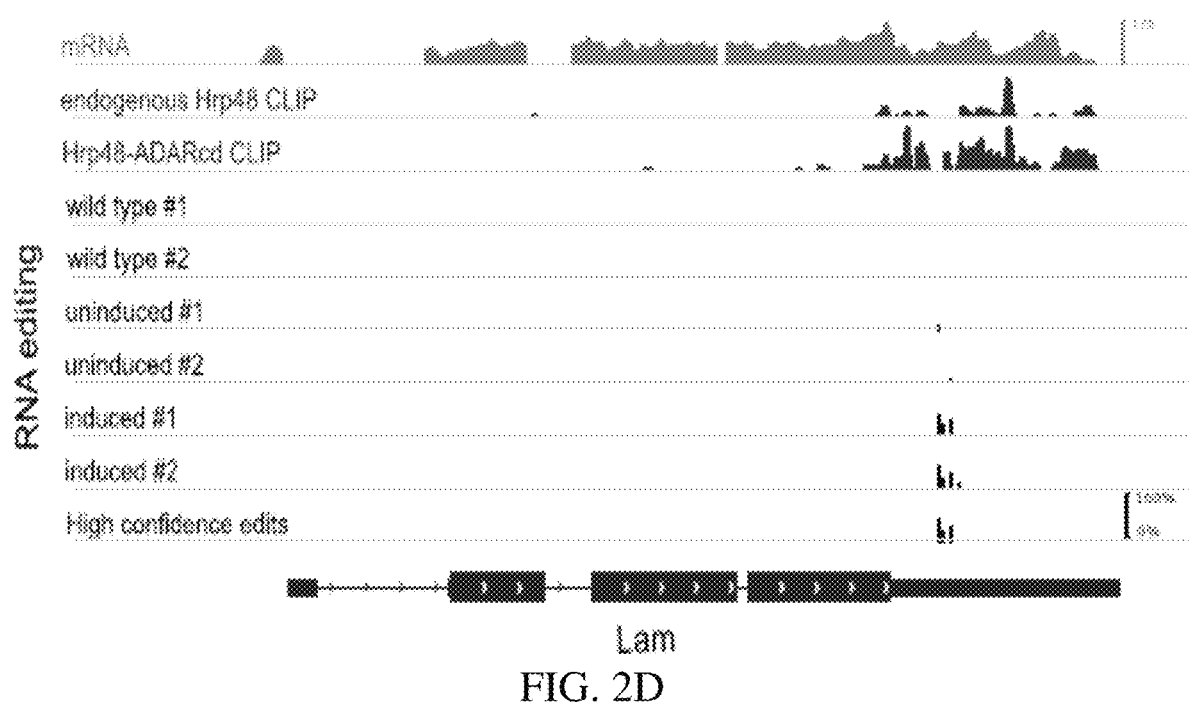

The majority of target genes are marked by a single editing site, and these events are reproducible both in their position and frequency (percent editing), indicating that Hrp48-TRIBE exhibits specificity (FIGS. 2B and 2C). Genes that are marked by editing sites in both biological replicas are defined as high-confidence TRIBE targets (FIGS. 2B and 2D). For Hrp48, these 1,401 targets constitute approximately 20% of all expressed genes (FIG. 2B) and have a wide range of expression levels, indicating that TRIBE was selective.

Figure 3:
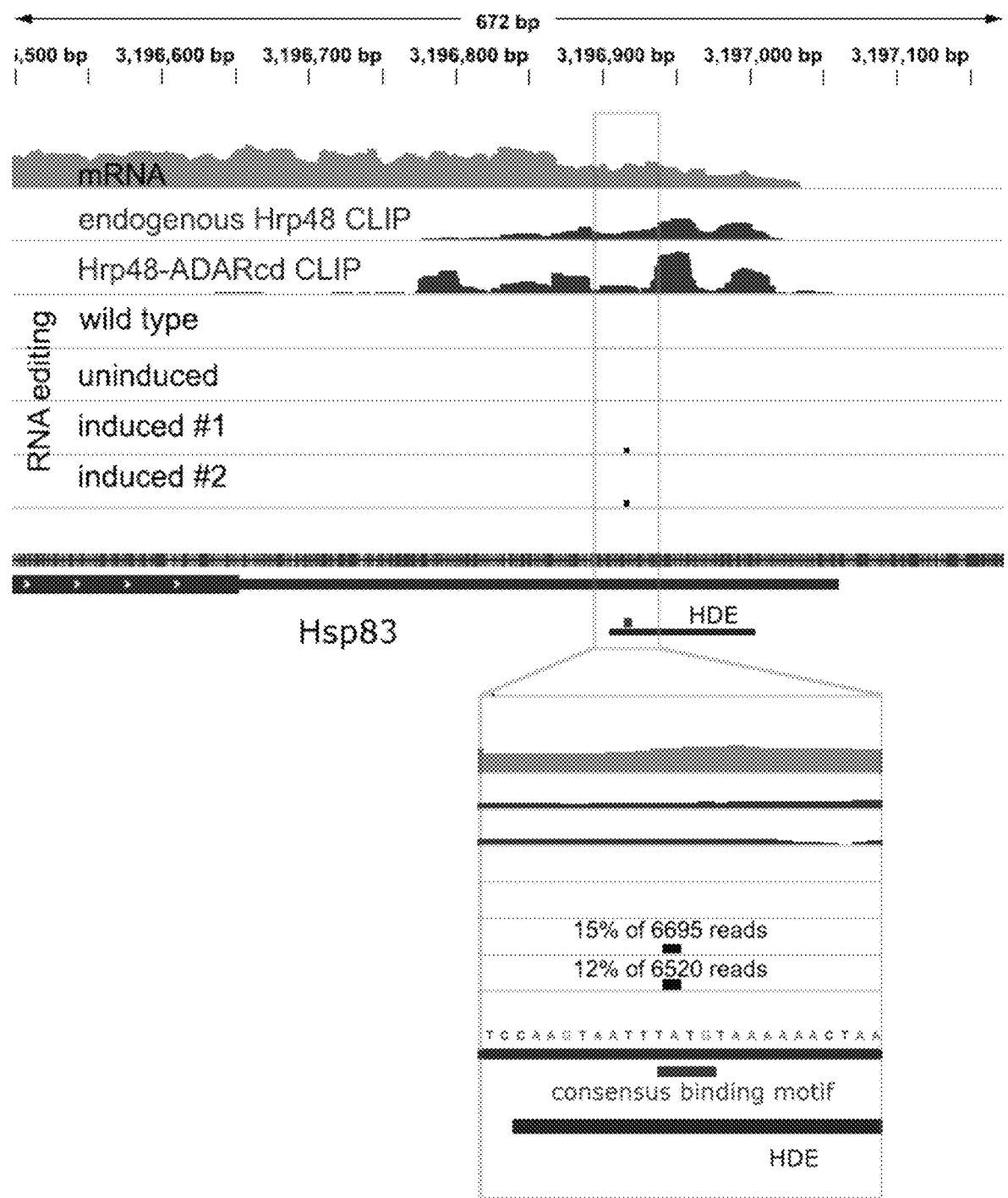
FIG. 3 provides an editing event map indicating a well-defined target of Hrp48, Hsp83, was edited by Hrp48-TRIBE in the correct location. The Hsp83 degradation element (HDE) was known to be bound by Hrp48 (Bashirullah et al.; Nelson et al.), Hrp48-TRIBE causes editing within the consensus Hrp48 binding motif (Blanchette et al; also see FIG. 5) within the HDE. The data was obtained from S2 cells, editing percentage of total number of reads is shown at the edit sites.

Example 2: Clip and Tribe Agree that Hrp48 Preferentially Binds to the 30 UTR of Transcripts To assess if editing sites reflect true Hrp48 target genes, a series of CLIP-Seq experiments were performed to address target preference by this more traditional method. First, CLIP of endogenous Hrp48 shows the same binding pattern as CLIP of the Hrp48-TRIBE fusion polypeptide. Both proteins are strongly enriched in the 30 UTR, as is seen in an example gene Lam (FIG. 2D). In a well-characterized target of Hrp48, both Hrp48 CLIP and Hrp48-ADARcd CLIP show binding throughout the 30 UTR surrounding a specific element previously shown to be bound by Hrp48 (FIG. 3) (Bashirullah et al., EMBO J., 1999 18, 2610-2620; Nelson et al., J. Biol. Chem. 2007, 282, 34031-34038.). This 30 UTR binding pattern holds transcriptome-wide (FIG. 4A) and further indicates that fusion to the ADARcd does not markedly interfere with the ability of the RBP to recognize and bind to its normal targets. Similarly, fusion of the ADARcd to Hrp48 did not alter its largely cytoplasmic localization pattern (as assayed by immunocytochemistry and subcellular fractionation).

Figure 4A:
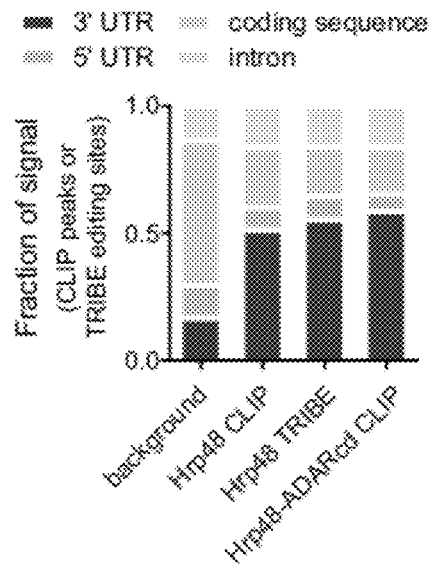
FIGS. 4A-4D show TRIBE data indicating that Hrp48 preferentially binds the 30 UTR of transcripts.

The 30 UTR binding preference of Hrp48 identified by CLIP is closely mirrored by the pattern of Hrp48-TRIBE editing sites. Transcriptome-wide, approximately 50% of Hrp48-TRIBE editing sites and 50% of Hrp48 CLIP peaks are found in the 30 UTR (FIG. 4A). This data indicates that TRIBE editing marks endogenous targets quite close to the region of the RBP binding site.

Figure 4B:
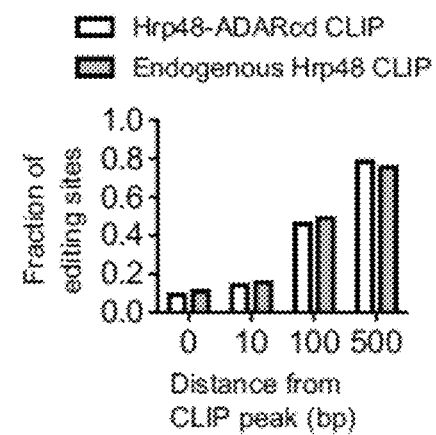

Indeed, Hrp48-TRIBE edits within the previously characterized binding element of Hsp83 (FIG. 3A), showing that TRIBE can mark an RBP binding site. Overall, ~10% of TRIBE editing sites are located within a CLIP peak (as in the Hsp83 example), and ~80% are less than 500 bp from a CLIP peak (FIG. 4B). Motif analysis of the Hrp48 CLIP data identify TA-rich binding motifs similar to that previously published using in vitro selection (Blanchette et al., Molecular cell. 2009, 33:438-449), but TA-rich motifs were not found surrounding editing sites (FIG. 5). The data indicates that TRIBE usually edits near, but not at, the binding site, consistent with fusion of the editing moiety to the C terminus of Hrp48. However, some more distant editing might be due to RNA flexibility and/or the dsRNA preference of the ADARcd (discussed later).

Figure 4C:
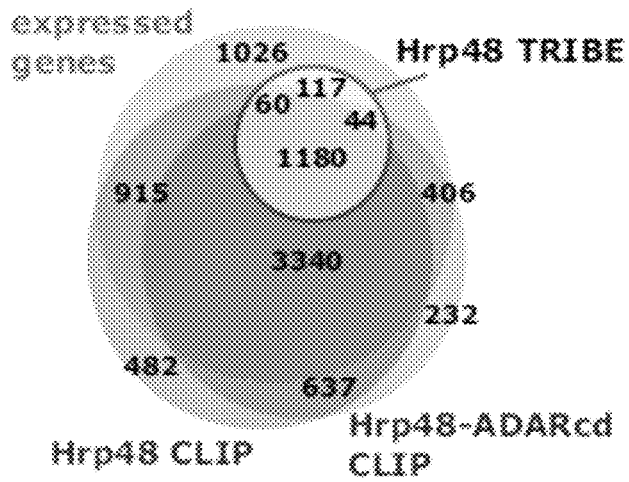
Figure 4D:
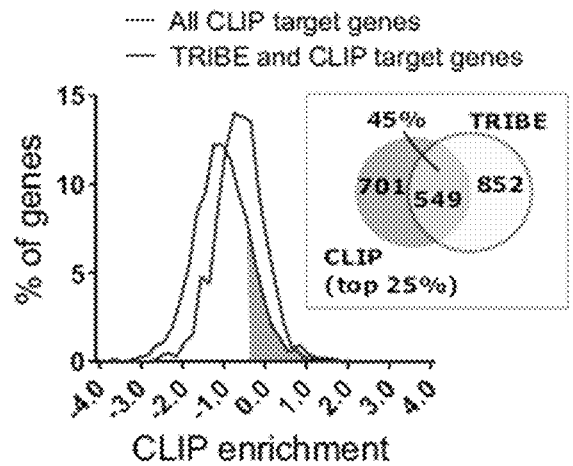
Figure 5A:
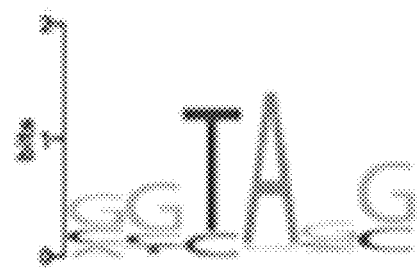
FIG. 5A-5E provide schematics of a motif analysis for Hrp48, Hrp48-ADARcd CLIP, and Hrp48-TRIBE editing events.
Figure 5B:
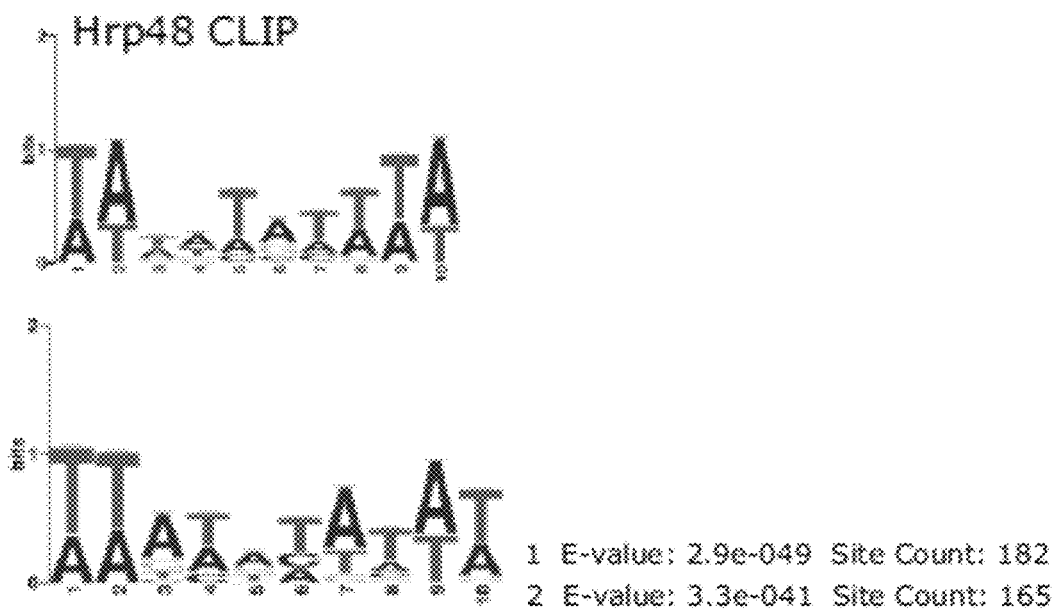
Figure 5C:
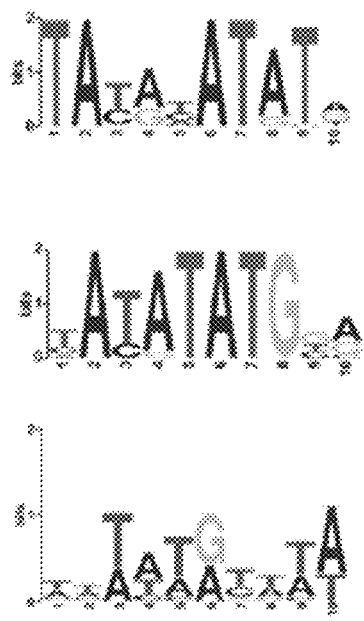
Figure 5D:
Figure 5E:
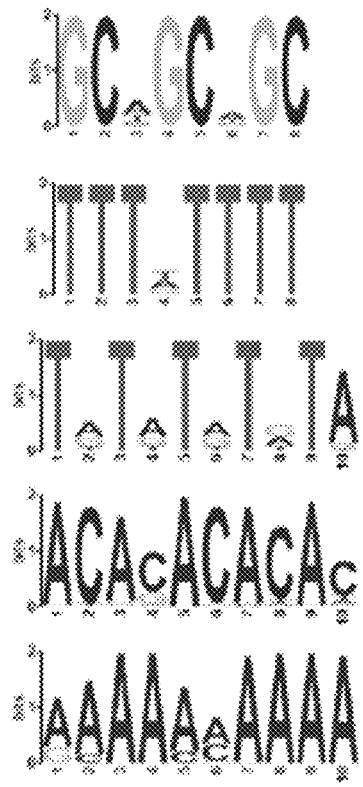
Figure 6A:
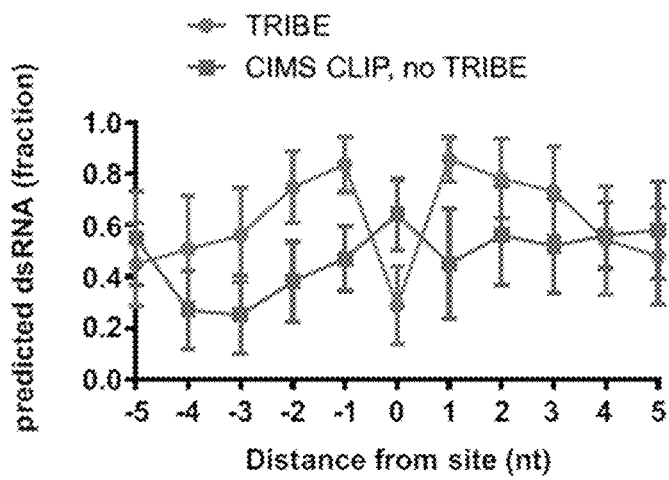
FIGS. 6A-6B show RNA Structure Prediction around TRIBE Editing Sites.
Figure 6B:
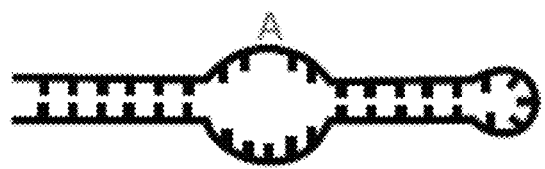

Hrp48-TRIBE defines fewer targets than Hrp48 CLIP. Most expressed genes have at least one statistically significant CLIP peak, with similar results from endogenous Hrp48 and the Hrp48-TRIBE fusion polypeptide (FIG. 4C). This is in contrast to TRIBE targets, which are more restricted and comprise only ~20% of expressed genes (FIG. 4C). These results are from very deep sequencing (~200 M reads), which indicated that the more restricted target set was not merely due to lack of sensitivity. Because a single, statistically significant CLIP peak was not a stringent threshold for defining a target, total CLIP enrichment (relative to expression) was calculated per gene. Compared to the whole population of genes identified by CLIP, Hrp48-TRIBE target genes are biased toward higher CLIP enrichment (right shifted distribution; FIG. 4D); indeed, 45% of the top quarter ranked CLIP targets was also TRIBE targets, which indicated that Hrp48-TRIBE preferentially detects stronger Hrp48 CLIP tar-gets (FIG. 4D, inset). Structure prediction modeling of the regions surrounding TRIBE editing events indicated that editing occurs preferentially at a bulge embedded within dsRNA (FIG. 6A), similar to an RNA structure edited by the human ADAR2cd when expressed in *Saccharomyces cerevisiae* (FIG. 6B) (Yi-Brunozzi et al., J. Biol. Chem. 2001, 276, 37827-378332001; Gupta et al., RNA Biol. 2012, 9, 187-199; Eifler et al., Biochemistry. 2013, 52, 7857-7869). This structure is absent from CLIP binding regions that lack an editing site (FIG. 6A) Taken together, the cell culture data for Hrp48-TRIBE indicate that TRIBE labels many endogenous Hrp48 targets and in the correct metagene location.

Example 3: DFMR1-Tribe Preferentially Edits Coding Sequence, Reflecting Prior Clip Data A second TRIBE protein was created by fusing dFMR1, the *Drosophila* ortholog of FMRP (fragile X mental retardation protein) to the ADARcd. dFMR1 has roles in mRNA localization and translational regulation in neurons.

Figure 7A:
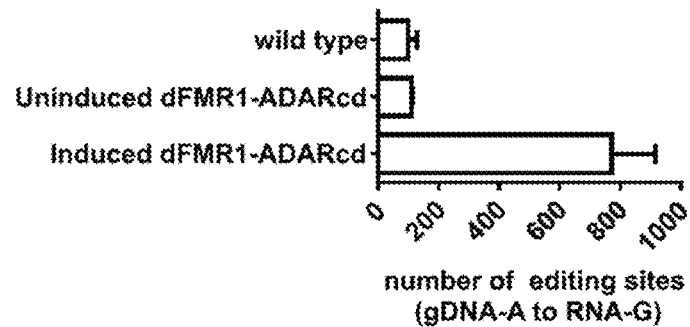
FIGS. 7A-7E show TRIBE data demonstrating that dFMR1 preferentially binds the coding sequence of transcripts.
Figure 7B:
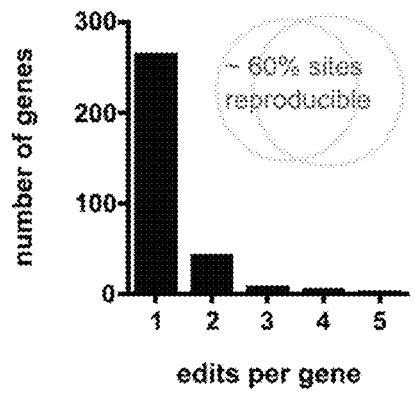
Figure 7C:
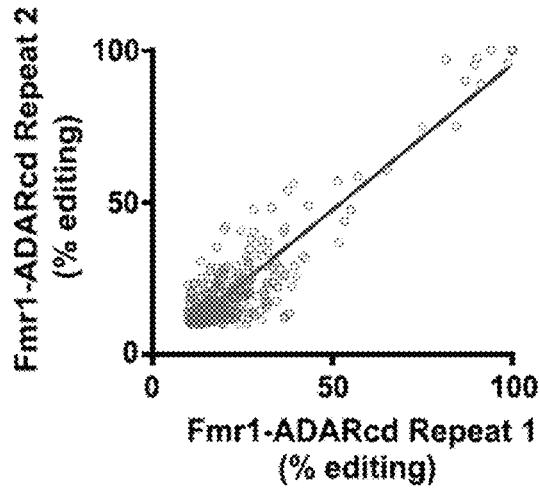

As observed for Hrp48-TRIBE, induction of dFMR1-TRIBE expression in *Drosophila* S2 cells led to a robust increase in editing events (FIG. 7A). The majority of targets were marked by only one editing site, and these individual editing events were reproducible both in their position and frequency (percent editing), indicating that dFMR1-TRIBE manifests specificity (FIGS. 4B and 4C). Genes that were marked by editing sites in two biological repeats were classified as high-confidence TRIBE targets (FIG. 7B). In the case of dFMR1, these 315 targets constitute approximately 5% of all expressed genes.

Figure 7D:
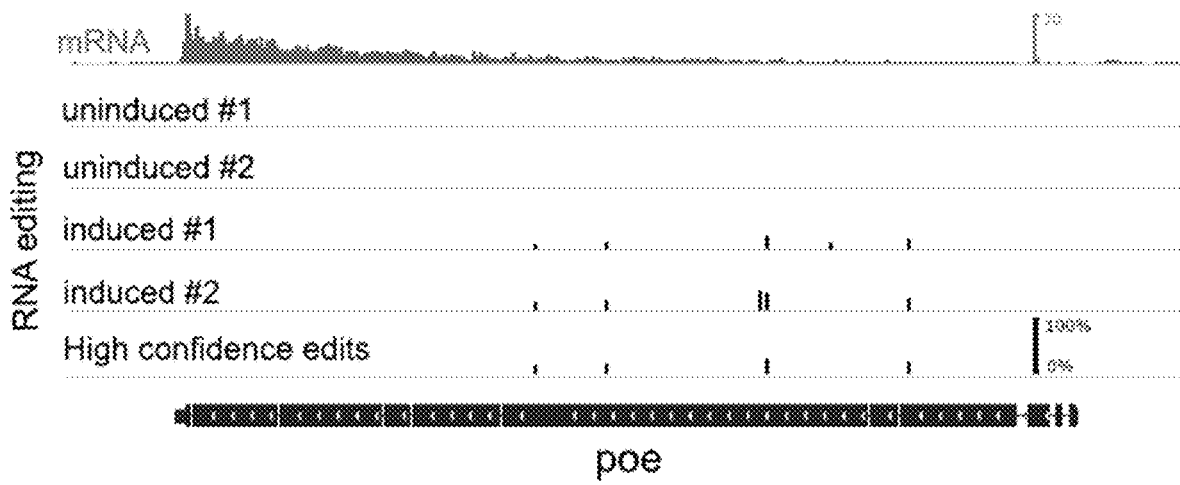
Figure 7E:
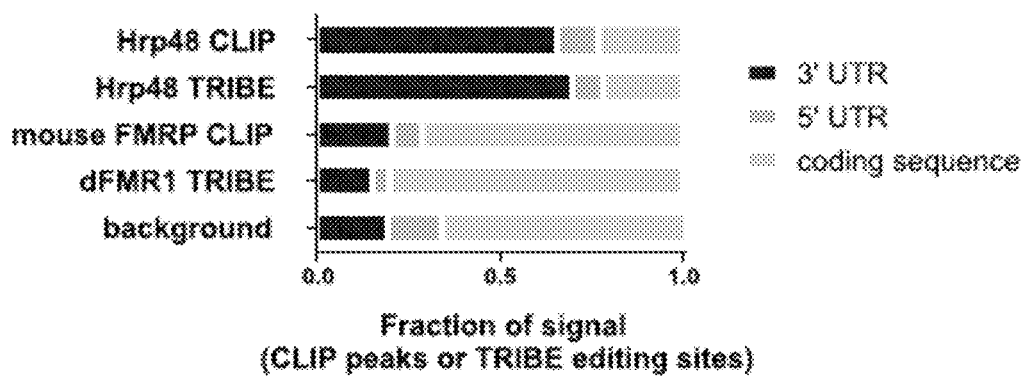
Figure 8A:
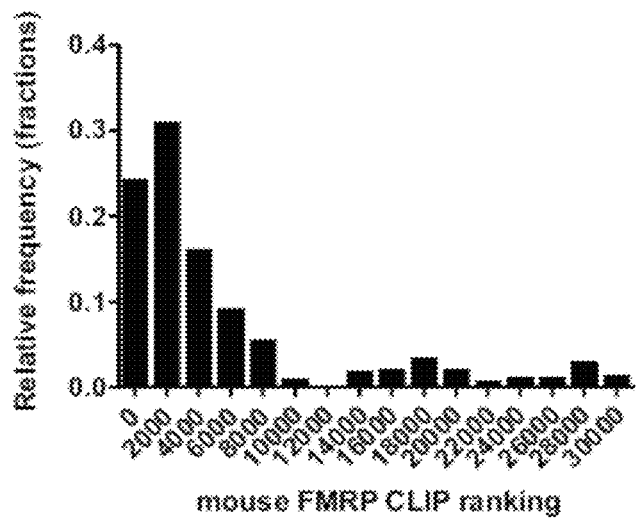
FIGS. 8A-8C shows data indicating mouse homologs of fly dFMR1-TRIBE targets were enriched for higher CLIP rankings.

In stark contrast to the distribution of Hrp48-TRIBE editing events, dFMR1-TRIBE editing events are distributed throughout the coding region of transcripts (FIGS. 7D and 7E). This same pattern has been observed by CLIP of FMRP in mammalian cells (Darnell et al., Cell, 2011 146, 247-261; Ascano et al., Nature. 2012, 492, 382-386) and is consistent with the role of dFMR1 as a translation regulator. Further examination of mouse brain FMRP CLIP targets revealed that the mouse homologs of the dFMR1-TRIBE target genes were biased toward higher CLIP rankings, suggesting that dFMR1-TRIBE identifies conserved targets of FMRP (FIG. 8A) (Darnell et al.).

Example 4: Tribe Shows that Nona Preferentially Binds TNTRONS

A third *Drosophila* RBP, NonA, is the ortholog of the mammalian protein NonO and was assayed in a similar manner as described above. NonO is a multifunctional protein involved in the function of nuclear para-speckles as well as other nuclear events like splicing, mRNA export and the regulation of transcription.

Figure 9A:
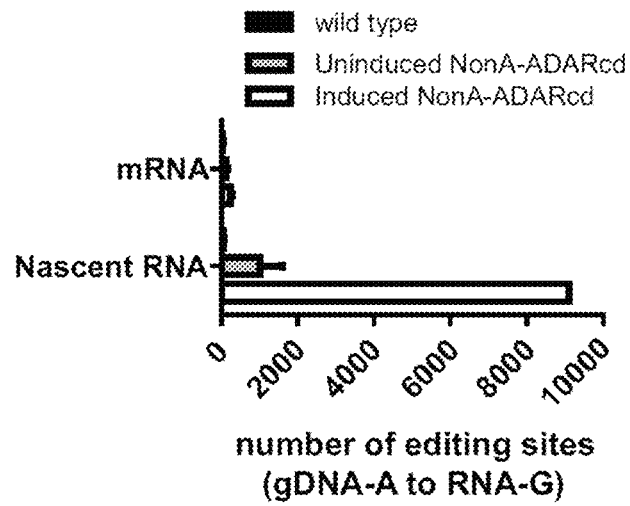
FIGS. 9A-9E shows TRIBE data demonstrating that NonA preferentially binds the introns of transcripts.
Figure 10A:
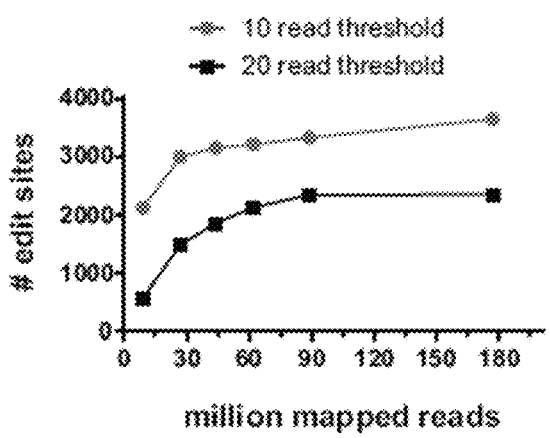
FIGS. 10A-10B provide graphs indicating the sequencing depth and number of TRIBE editing sites detected.
Figure 10B:
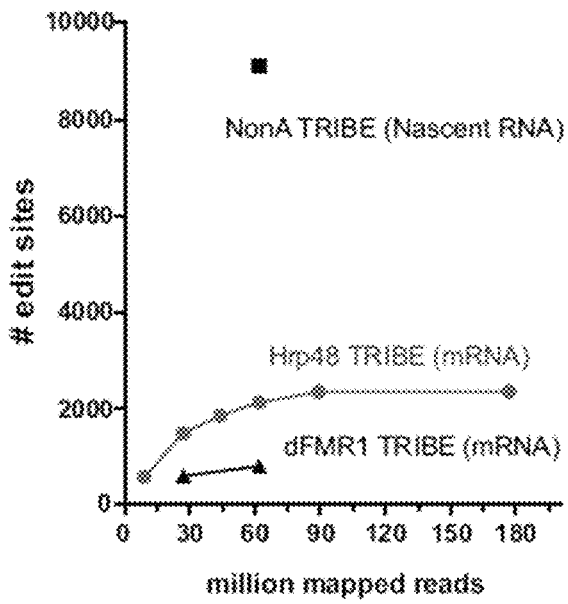
Figure 11A:
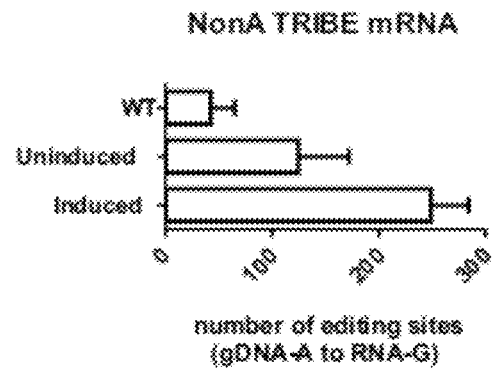
FIGS. 11A-11D show that the ability of NonA TRIBE to identify intronic targets in mRNA.
Figure 11B:
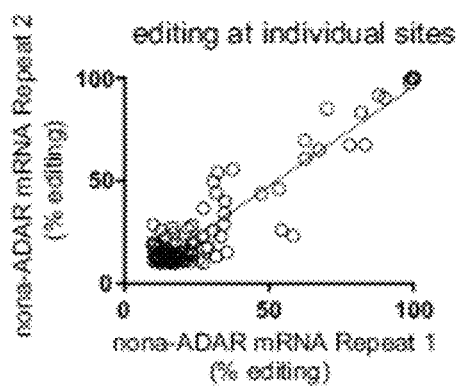
Figure 11C:
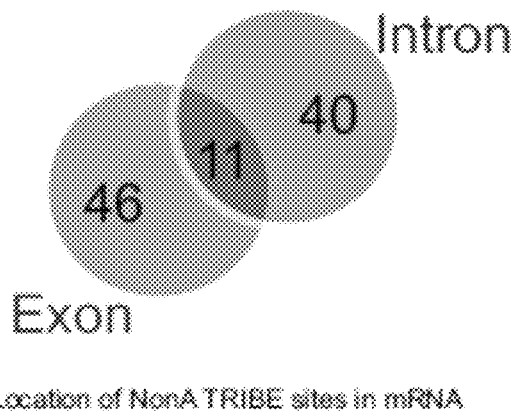
Figure 11D:
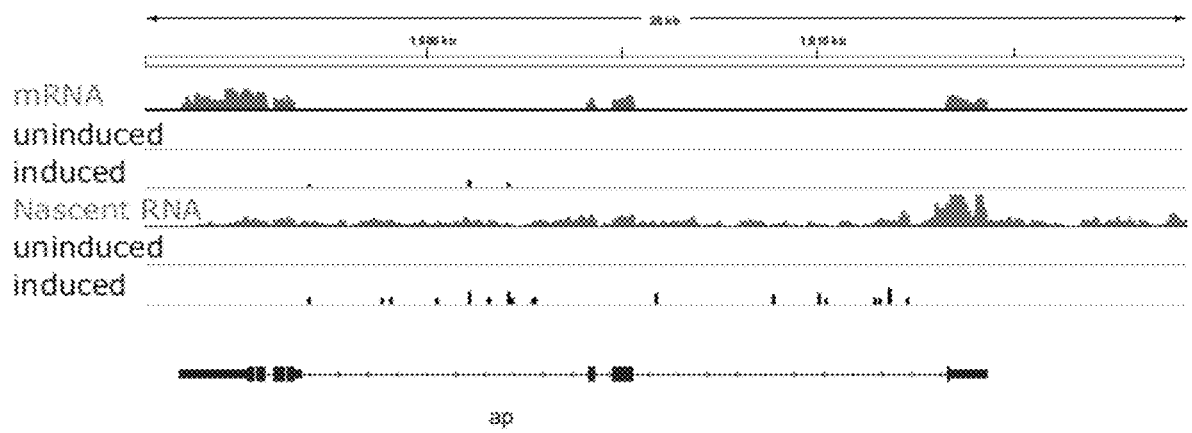

Expression of the NonA-TRIBE fusion polypeptide in S2 cells led to a small increase in mRNA editing (approximately 3-fold; FIG. 9A top), much less than what was observed above with the dFMR1 and Hpr48 fusion polypeptides. Because of the known nuclear functions of NonA, it was considered that NonA might preferentially bind nascently transcribed nuclear RNA To this end, chromatin-associated RNA from S2 cells was isolated and sequenced (Wuarin and Schibler. Mol. Cell. Biol. 1994, 14, 7219-7225; Khodor et al., Genes Dev., 2011, 25, 2502-2512). Indeed, the nascent RNA from cells expressing NonA-TRIBE had 30-fold more editing sites than mRNA, even at a lower sequencing depth (mRNA ~300 sites, ~90 M mapped reads; Nascent RNA, ~9,000 sites, ~60 M mapped reads) (FIGS. 9A and 10B).

Figure 9B:
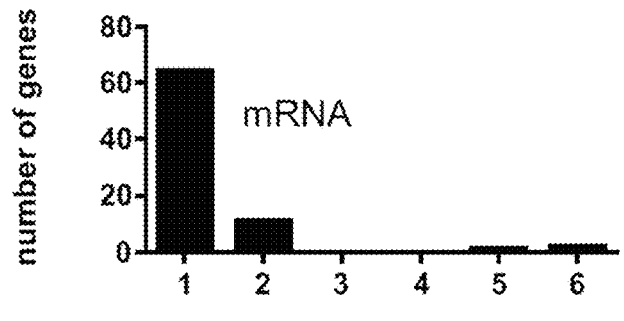
Figure 9C:
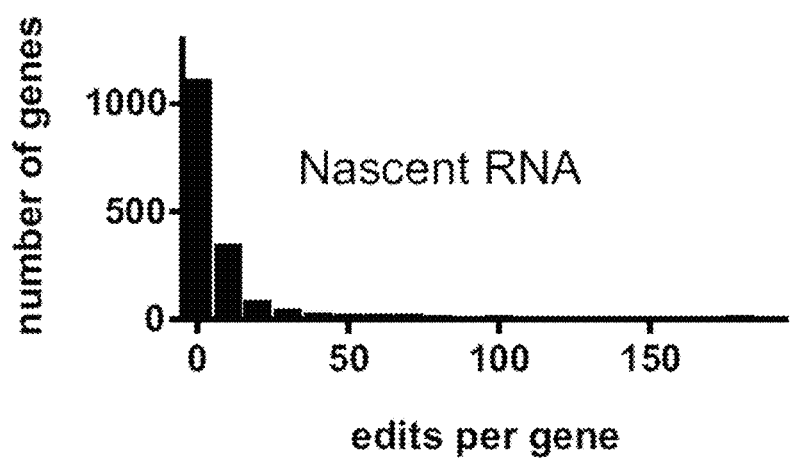

The nascent RNA edited by NonA-TRIBE has many genes with multiple editing sites per gene (FIG. 9C), in contrast to the editing events in mRNA due to Hrp48-TRIBE (FIG. 2B), dFMR1-TRIBE (FIG. 7B), or even NonA-TRIBE (FIG. 9B) The median number of sites per gene in nascent RNA is 2, and 25% of genes have greater than 6 sites per gene. These sites are in 1,561 target genes, approximately 20% of expressed genes. The maximum number is 181 sites (in Shab).

Figure 9D:
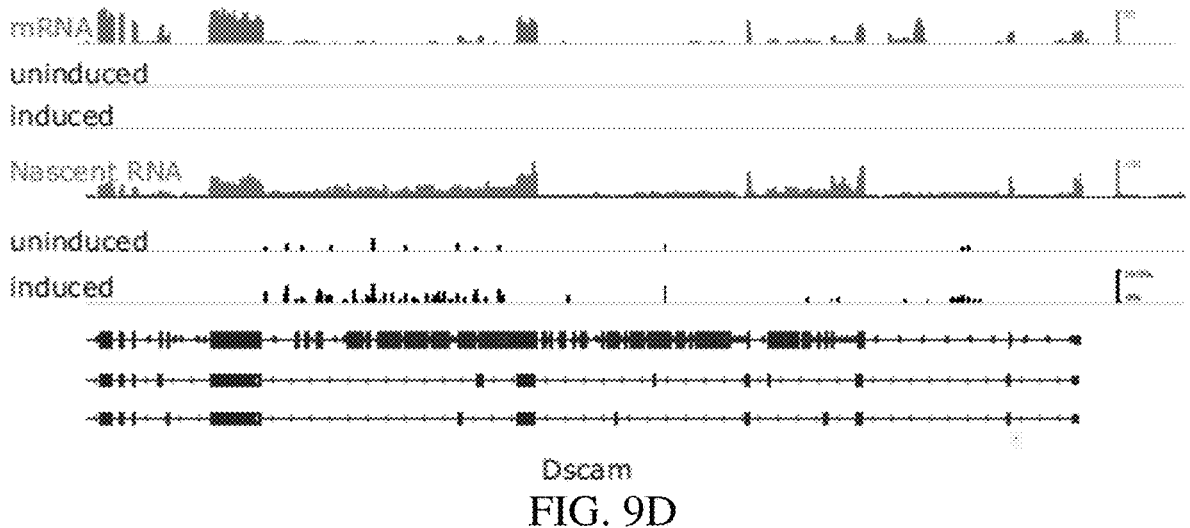
Figure 9E:
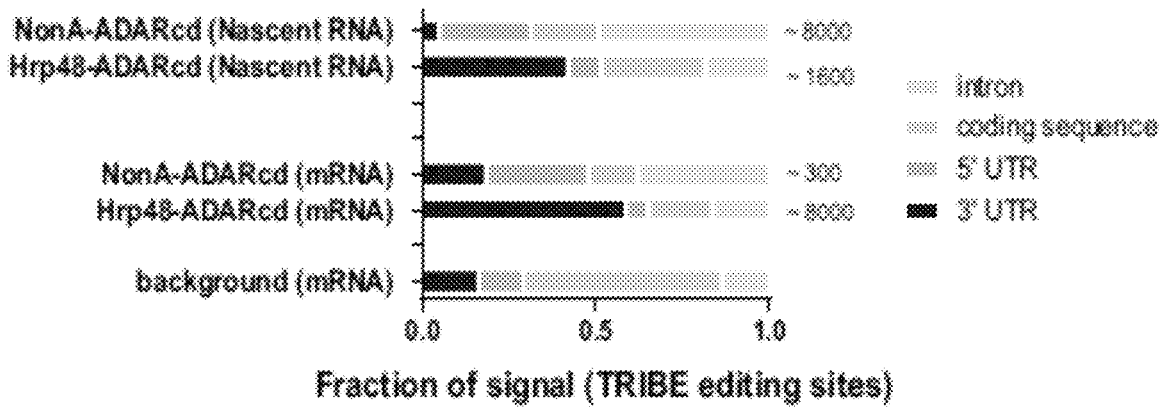

Not surprisingly, NonA-TRIBE editing sites are enriched in intronic regions of the nascent transcripts (FIGS. 9D and 9E). Perhaps owing to retained introns, half of the few (40) NonA-TRIBE editing events in mRNA are also in intronic regions (FIG. 11). Nascent RNA sequenced from cells expressing Hrp48-TRIBE does not show this intronic concentration of editing sites (FIG. 9E). On the contrary, Hrp48-TRIBE maintains its preference for 30 UTRs even in nascent RNA This is despite the fact that nascent transcripts contain fewer 30 UTR reads due to the 50 enrichment of nascent RNA The NonA moiety therefore dictates the preference of NonA-TRIBE for intronic RNA rather than it being a general RBP property.

Gene ontology (GO) analysis reinforces the different roles of the three RBPs as the targets of each RBP have divergent functions. The cell culture experiments taken together indicate that TRIBE can determine the RNA targets of three RBPs, as well as where on a transcript they bind.

Example 5: HRP48-Tribe can Identify RBP Targets in Specific Cells

Because the targets of many RBPs are likely to be different between tissue and cell types, test were conducted to determine whether TRIBE can identify cell-specific RBP targets within the fly brain. To achieve cell-specific expression of the TRIBE proteins, the *Drosophila* UAS/Gal4 system was employed. Transgenic fly lines harboring the Hrp48-TRIBE transgene under the control of the UAS promoter were generated. Cell-specific expression was achieved using a range of Gal4 driver lines, which express the UAS transcriptional activator Gal4 only in specific subsets of neurons. The neuronal groups examined were the core circadian PDF neuropeptide expressing cells (pdf-Gal4, ~16 cells/brain), dopaminergic neurons (Tyrosine hydroxylase, TH-Gal4, ~1,000 cells/brain) and all neurons (pan-neuronal driver, elav-Gal4, ~100,000 cells/brain). A fluorescent protein (UAS-eGFP) was co-expressed to allow manual cell sorting of TRIBE protein-expressing and control neurons from dissociated *Drosophila* brains.

Figure 12A:
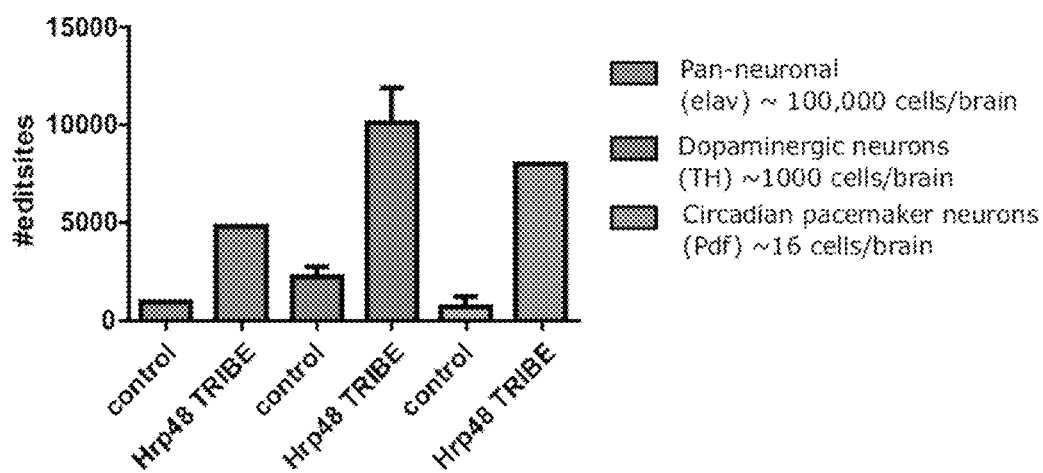
FIG. 12A-12E show Hrp48-TRIBE can identify RBP targets in specific subsets of cells.

Similar to the cell culture result, neuronal expression of the Hrp48-TRIBE protein caused a large increase in the number of editing sites, far more than the level of endogenous editing (range of endogenous editing sites, ~300-2, 000; range of TRIBE editing sites, ~8,000-11,000; FIG. 12A). Neuronal expression of only the ADARcd gave rise to no additional editing. All endogenous editing events detected in any cell type were excluded from downstream analysis of TRIBE expressing neurons. Like in S2 cells, editing events due to Hrp48-TRIBE were enriched in the 30 UTRs of neuronal transcripts, which had even more edits per gene than was typical in cultured S2 cells. This may partly be a result of the extended length of 30 UTRs often observed in neurons compared to other cell types.

Figure 12B:
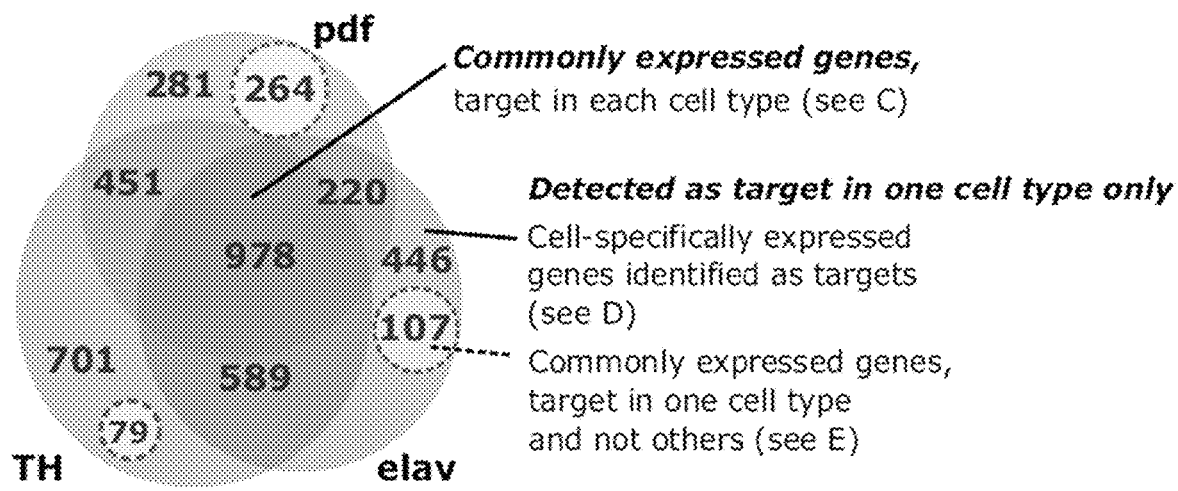
Figure 12C:
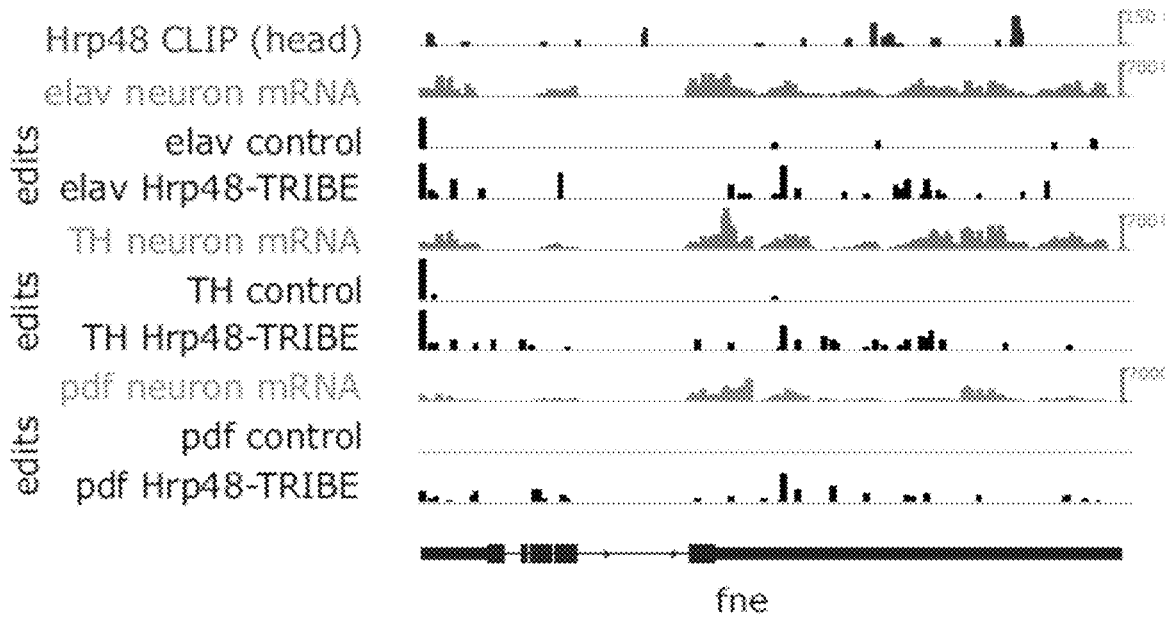

Similar numbers of Hrp48 target genes were identified in each of the three cell types (1743-2798); the target gene sets were overlapping, but not identical (FIG. 12B). Not surprisingly, commonly expressed genes were identified as targets in all three cell types (FIGS. 12B and 12C). For example, the neuronal RBP named "found in neurons," (FNE) was identified as a Hrp48 target in all neuronal subsets, other targets in this class include bru-3, mamo, and pum.

However, some genes were identified as a target in only one or two cell types despite being expressed in all three. For example, the genes galectin, aret, and Spp were expressed in all three cell types, but aret is identified as a target only in TH cells. Galectin was identified as a target in pdf and TH cells, and Spp is a target in pdf and elav cells (FIG. 12E). These "commonly expressed genes" have sufficient sequencing depth at the given base position (minimum 20 reads) in all three cell types to detect an editing event of roughly comparable frequency, indicating that editing is indeed cell-type specific.

Figure 12D:
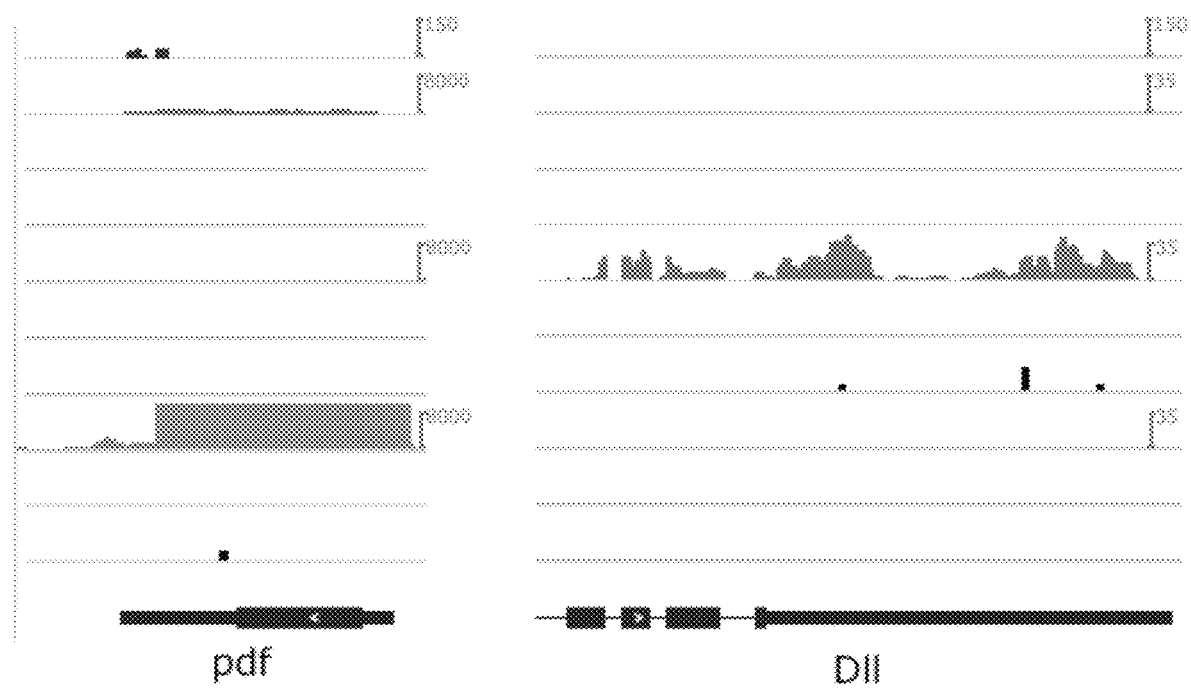
Figure 12E:
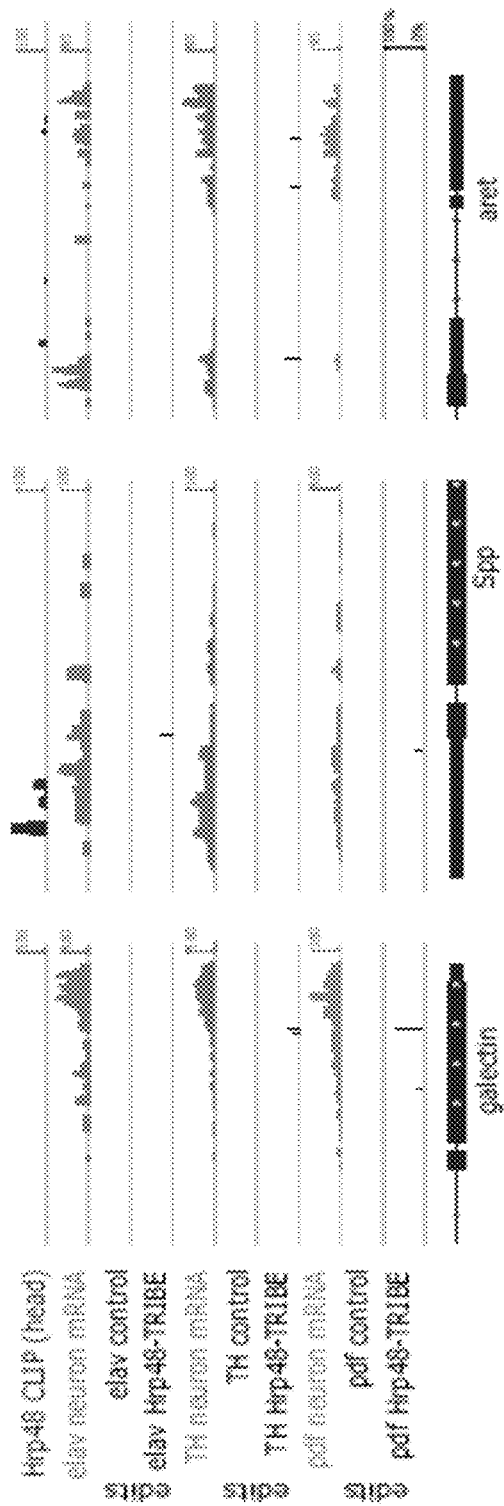

Another set of targets are identified in only one or two cell types due to bonafide cell-type-specific gene expression differences: for example, pdf is only identified as a target in pdf neurons because it is only expressed there; similarly, the transcription factor Dll is only expressed in dopaminergic (TH) neurons where it is also identified as a Hrp48 target (FIG. 12D). Note that there are probably a number of genes inappropriately assigned as cell-specifically expressed (FIG. 12B). This occurs when the specific editing site has insufficient coverage (due to uneven sequencing coverage) despite acceptable overall gene expression.

These Hrp48 target genes were also analyzed by gene ontology (GO) terms. Common target genes are not surprisingly enriched for general neuronal functions, consistent with the newly described role of Hrp48 in axon guidance and branching, whereas cell-specific target gene functions were distinct. This probably reflects cell-specific gene expression patterns as well as cell-specific binding of Hrp48 to commonly expressed genes.

Figure 13A:
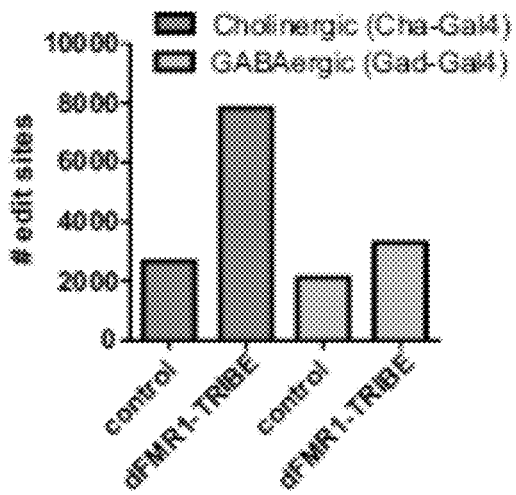
FIGS. 13A-13F show data identifying dFMR1 targets in excitatory and inhibitory neurons FIG. 13A provides a graph indicating the number of editing sites detected in RNA isolated from specific subsets of neurons expressing the dFMR1-TRIBE protein (the bars labeled TRIBE) was greater than the background number of endogenous editing sites (the bars labeled control). Excitatory neurons (cholinergic; Cha-Gal4) and inhibitory neurons (GABAergic; GAD-Gal4) were the cell types examined.
Figure 13B:
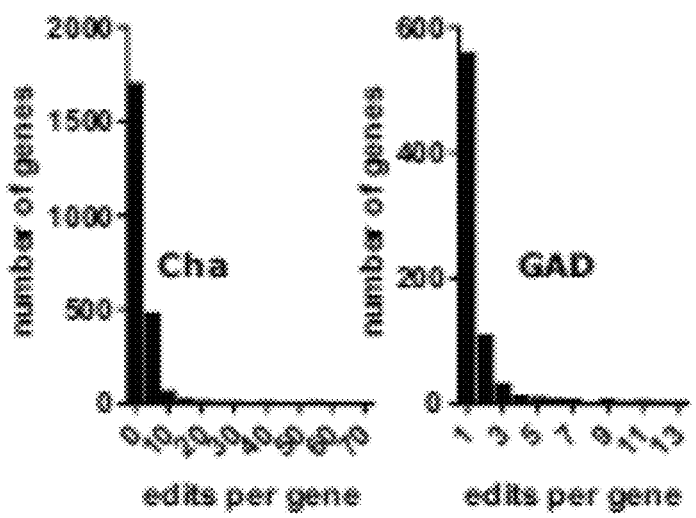
Figure 13C:
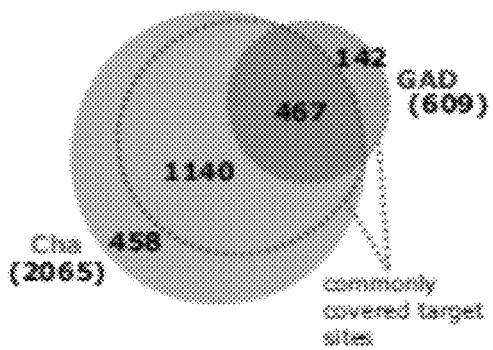
Figure 13D:
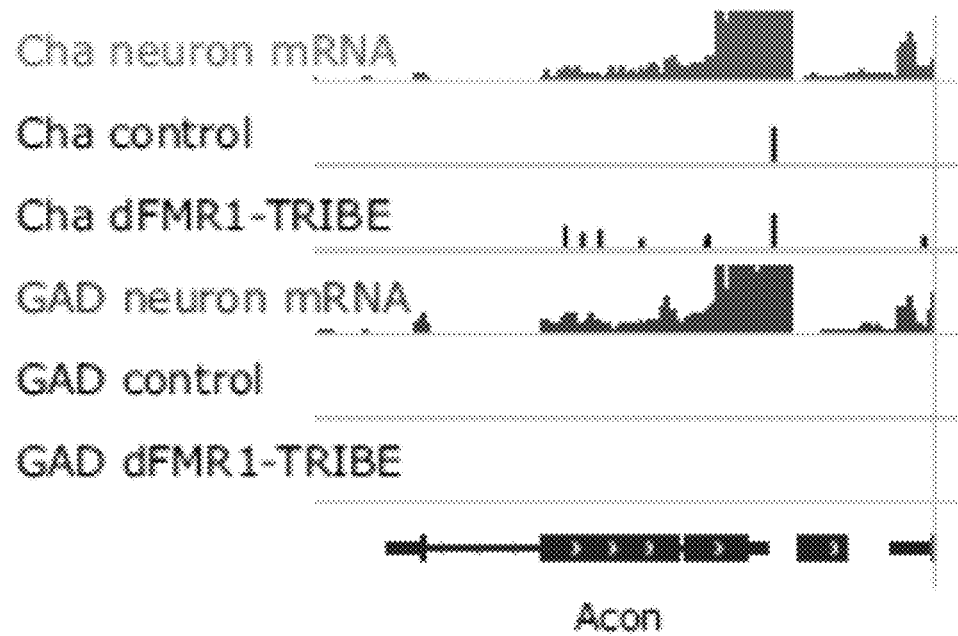
Figure 13E:
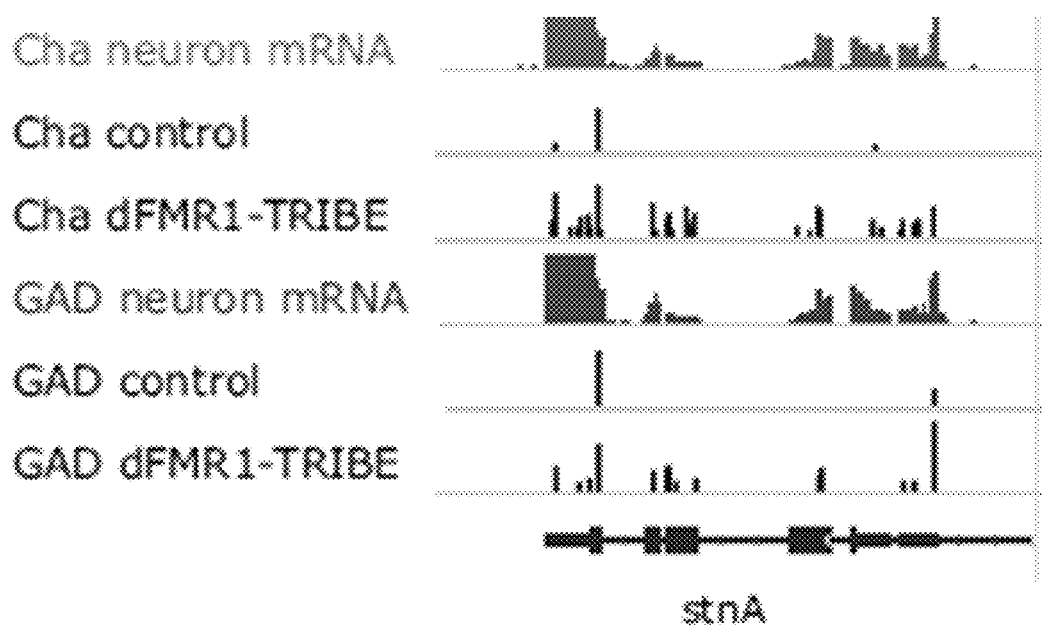
Figure 13F:
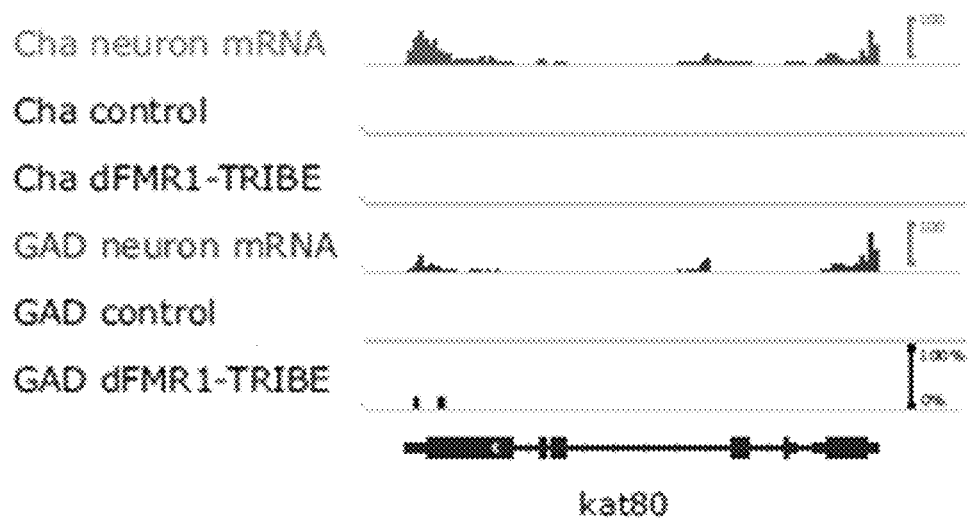

Example 6: DFMR1-Tribe can Identify RBP Targets in Specific Cells dFMR1-TRIBE was also expressed in specific neurons. Based on evidence from mammalian systems where the balance between excitation and inhibition is affected when FMRP is altered (e.g. Human Fragile X syndrome), the targets of dFMR1 in excitatory (cholinergic; Cha-Gal4) and inhibitory (GABAergic; GAD-Gal4) cells were selected for experimentation. They were purified as described above and the resulting isolated mRNA sequenced.

dFMR1-TRIBE editing sites were found throughout coding regions in neurons, which mirrors the cell culture results described above. Many fewer target genes were identified in GABAergic neurons than in cholinergic neurons (FIGS. 13A-13C), possibly due to the lower expression level of the TRIBE protein in GABAergic neurons. Due to this difference, Cha targets may not be truly cell-specific, but the smaller number of GAD-Gal4-specific dFMR1 targets indicate cell-specific targets (FIGS. 13C and 13F).

Figure 8B:
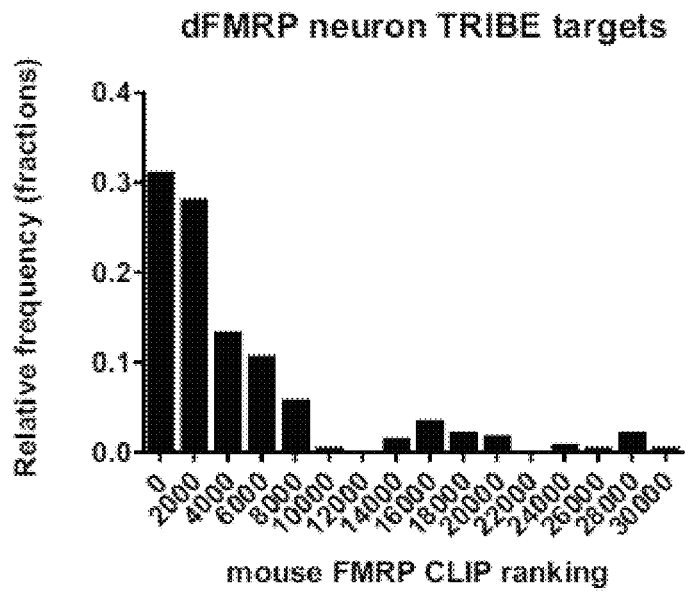
Figure 8C:
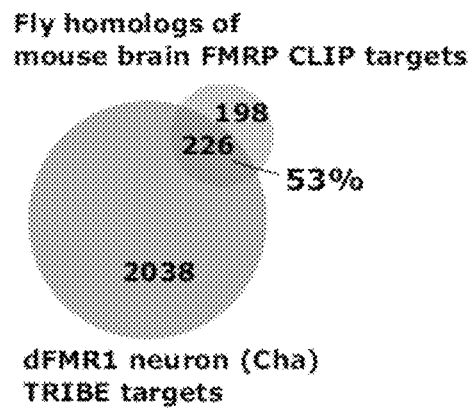

Gene Ontology (GO) analysis indicated that common targets are enriched for general neuronal functions, including genes associated with the known role of FMRP as a regulator of the microtubule network. Overall, 45% of robust mouse brain CLIP targets (Darnell et al.) that have clear fly homologs were also dFMR1 TRIBE targets in excitatory fly neurons (FIGS. 8B and 8C). One of these genes, futsch, the fly homolog of MAP1B, has been identified as a FRMP target by genetic means and was also the third ranked CLIP target in Darnell et al. GAD-specific dFMR1 targets are enriched for nuclear processes including transcription (FIG. 13F). In contrast, the Cha-specific targets are enriched for cytoplasmic functions, signal transduction and the regulation of GTPase activity (FIG. 13E). As described above for the Hrp48 cell-specific targets, dFMR1 cell-specific targets may reflect cell-specific gene expression and/or cell-specific binding of dFMR1 to commonly expressed genes.

Example 7: Tribe Identifies Targets of 4E-BP

The eukaryotic initiation factor eIF4F complex consists of many components including: eIF4E, the subunit that binds to the 5' cap of mRNA, which brings the complex to the mRNA; eIF4G, the scaffolding protein to which the other components bind; mitogen-activated protein kinase-interacting kinase 1 (Mnk1), an eIF4E kinase; and eIF4A, an RNA helicase. The functionality of the eIF4F complex relies on the association between eIF4E and eIF4G. However, the binding of 4E-BP to eIF4E displaces eIF4E from eIF4G and the remainder of the complex, and thus inhibits cap-dependent translation. mTOR complex 1 (mTORC1) controls whether or not 4E-BP binds eIF4E by controlling 4E-BP phosphorylation.

When mTORC1 is active, under positive grow 1 h conditions it phosphorylates 4E-BP, which is then unable to bind to eIF4E. Thus, eIF4E is free to bind to eIF4G, which completes the eIF4F complex on the 5' cap and permits translation to proceed. Under negative growth conditions, for example, during stress or pharmacological inhibition of mTORC1 by rapamycin or torin 1, mTORC1 is inactive and 4E-BP therefore becomes hypophosphorylated. As a consequence of hypophosphorylation, 4E-BP binds efficiently to eIF4E, thereby removing it from the eIF4F complex and inhibiting cap-dependent translation.

Figure 15A:
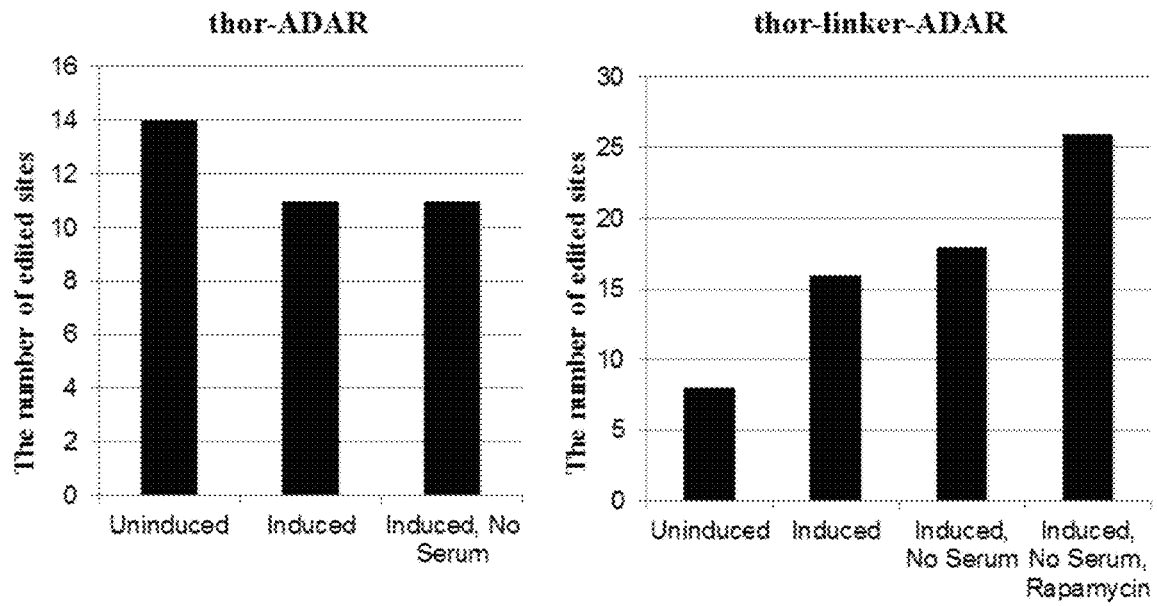
FIG. 15A provides graphs indicating the number of edited sites for Thor-ADAR and Thor-linker-ADAR fusion polypeptides.

To identify the binding partners of Thor, the *Drosophila* RBP that is an ortholog of the mammalian protein eIF4E-BP, additional experiments were conducted as described above. Two fusion polypeptides were generated to operatively link the catalytic domain of an ADAR with Thor, one fusion polypeptide contained a spatial linker region between Thor and the ADAR. Withholding serum or adding rapamycin enhanced target mRNA labeling as predicted from the literature on 4E-BP (FIG. 15A, right panel).

Figure 15B:
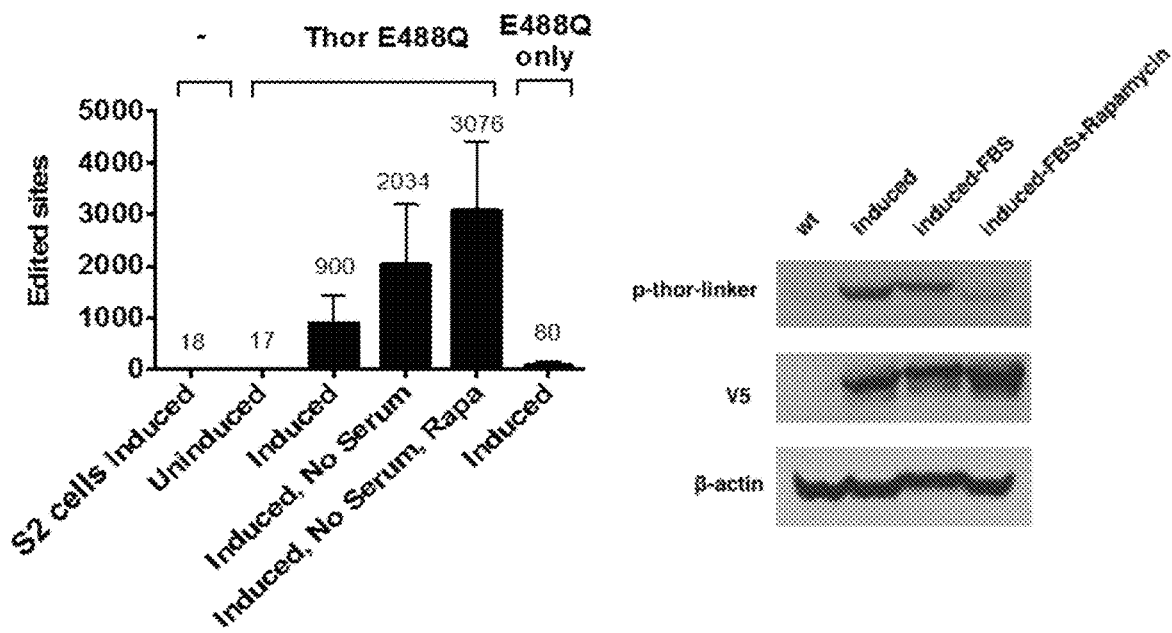
FIG. 15B provides a graph (left panel) indicating the number of edited sites for the Thor-E488Q mutant fusion polypeptide and a blot for p-thor-linker and VS (right panel).
Figure 15C:
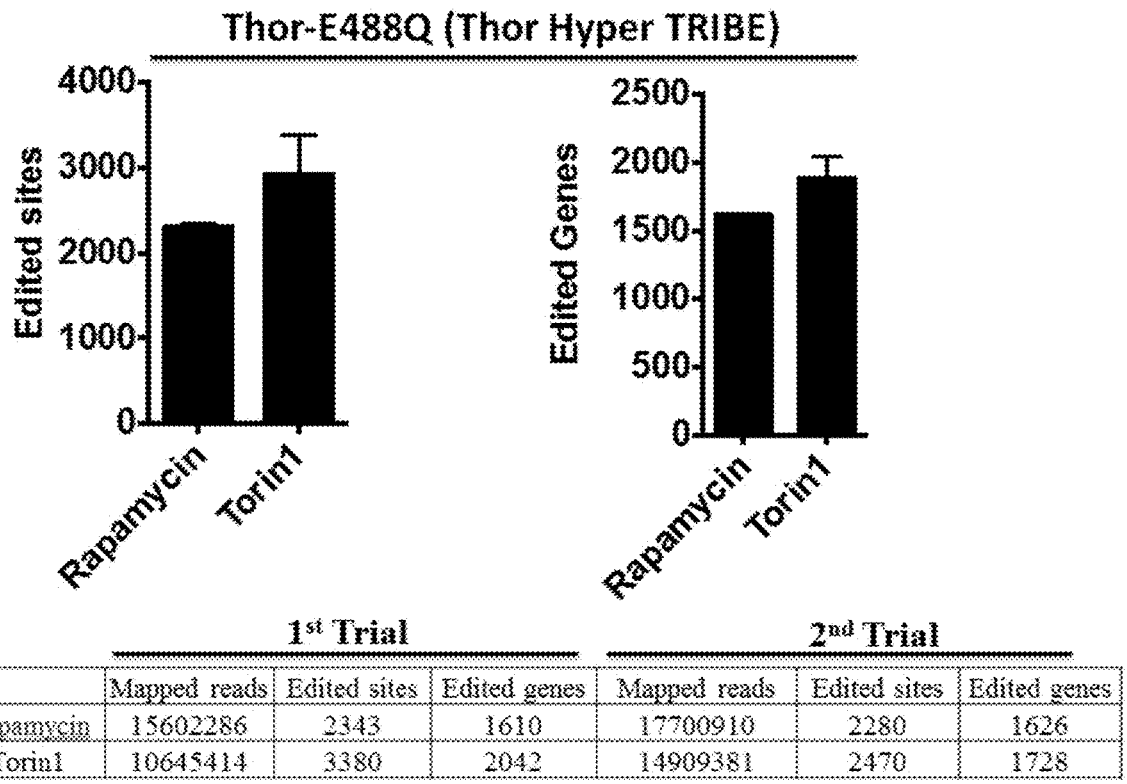
FIG. 15C provides a graph indicating the number of edited sites for the Thor-E488Q mutant fusion polypeptide in rapamycin and torin 1 treatment conditions (upper panel) and a chart provides the data represented in the graphs (lower panel).

Next, a fusion polypeptide was generated by introducing a mutation to the ADAR operatively linked to Thor. The ADAR mutation (E488Q) resulted in dramatically increased target mRNA labeling, especially after activation of Thor by serum depletion or rapamycin treatment (FIG. 15B), thus this method is called Thor-E488Q 'Hyper TRIBE." The mutant Thor-ADAR labeled even more target RNAs following the torin 1 treatment than following rapamycin treatment (FIG. 15C).

Figure 15D:
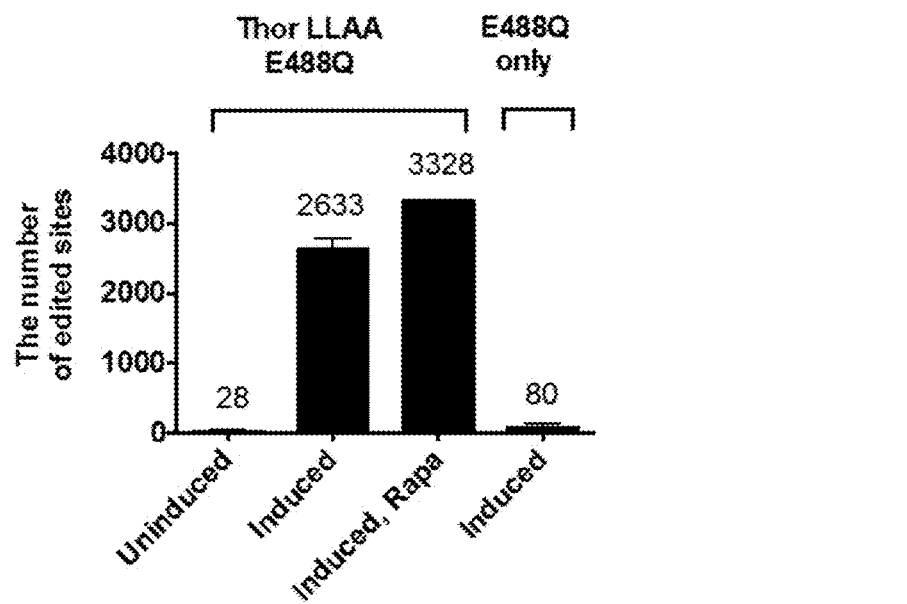
FIG. 15D provides a graph indicating the number of edited sites for the Thor-LLAA-E488Q mutant fusion polypeptide in rapamycin and torin 1 treatment conditions.
Figure 15E:
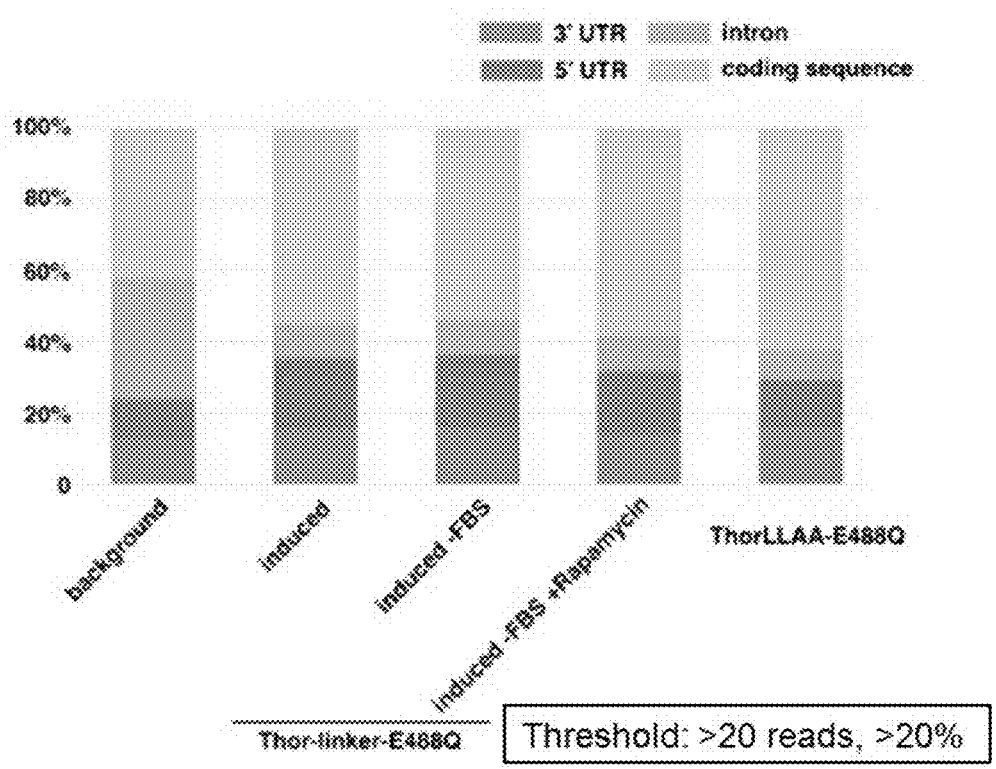
FIG. 15E provides a graph indicating that more edit sites are distributed in the 5' UTR and 3' UTR regions.

In addition to the Thor-ADAR-E488Q mutant, a constitutively active form of Thor (ThorLLAA) was used to label RNA targets. ThorLLAA can label RNA targets well under normal induction conditions in the presence and absence of rapamycin (FIG. 15D). Analysis using the Thor-linker-E488Q and ThorLLAA-E488Q mutant fusion polypeptides revealed that more sites are distributed in the 5' UTR and 3' UTR regions (FIG. 15E).

Figure 15F:
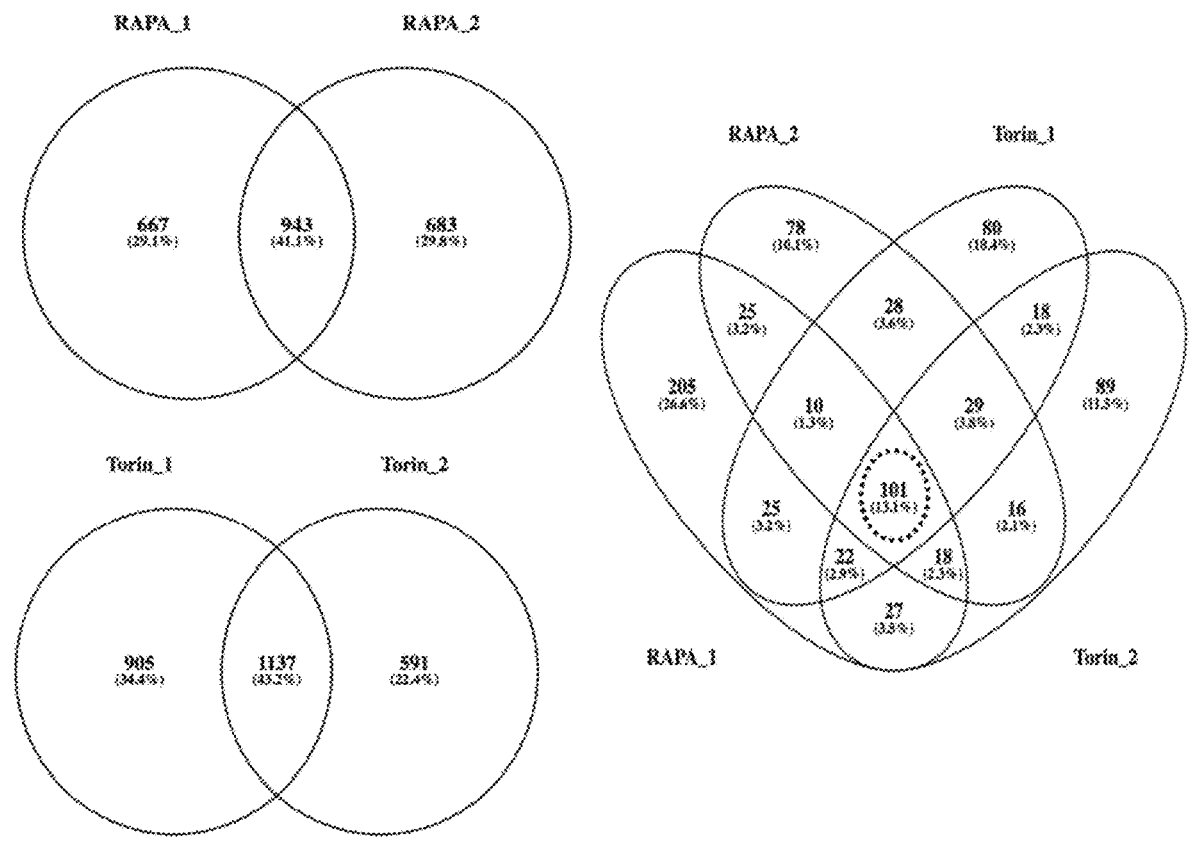
FIG. 15F provides a Venn diagram indicating the frequency distributions of common RNA binding targets of 4E-BP under rapamycin and torin 1 treatment conditions from different replicates.
Figure 15G:
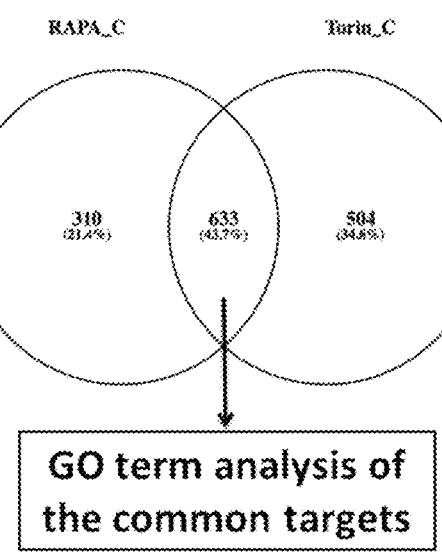
FIG. 15G provides Venn diagram indicating the frequency distributions of common targets of 4E-BP from different rapamycin and torin drug treatments.

Frequency distributions of common RNA binding targets of 4E-BP under rapamycin (RAPA_1, RAPA_2) and torin (Torin_1, Torin_2) treatment conditions from different replicates are shown in the left panel of FIG. 15F, whereas an overlapping target analysis of 5' editing sites is shown in the right panel of FIG. 15. Common targets of 4E-BP from different rapamycin and torin drug treatments were selected for further analysis (FIG. 15G). Thor TRIBE mRNA editing data is provided in Table 2. Thor TRIBE mRNA editing obtained with the E488Q mutant is provided in Table 3.

Furthermore, known binding partners of eIF4E regulated by the mTOR pathway, such as TOP and TOP-like mRNAs, were identified by the Thor analysis. Sequences of interest are provided in Table 4. TOP mRNAs start with a cytidine immediately after the 5' mRNA cap, followed by an uninterrupted segment of 4-14 bp of pyrimidines (underlined regions).

TABLE 4

TOP-LIKE MRNA SEQUENCES IN THOR TARGETS

| mRNA | Sequence |
|---|---|
| CG3164 | TTTCAGTTGCGATCGCGGCGCGAGCG |
| CG11454 | TTATCTTCTGCCATCACTACGT |
| CG4822 | CTTTACTCAGCAGCTCGCCATGCCAC |
| MFS10 | GTTTGTGTGTGTGTGT |

TABLE 2

THOR TRIBE MRNA DATA

|  | mapped reads | >10 reads, 10% edited sites | >20 reads, 10% edited sites |
|---|---|---|---|
| Thor-ADAR, no linker-FACS-160902 | | | |
| 1 pMTA-Thor-Adar, −cu | 16870372 (92.3% of input) | 388 | 14 |
| 2 pMTA-Thor-Adar, +cu | 15572458 (92.9% of input) | 365 | 11 |
| 3 pMTA-Thor-Adar, +cu no FBS | 16905329 (90.6% of input) | 442 | 11 |
| Thor-linker-ADAR, FACS-160323-160407 | | | |
| 1 Thor_linker_TRIBE −cu +FBS | 27227844 (82.3% of input) | 449 | 8 |
| 2 Thor_linker_TRIBE +cu +FBS | 19680364 (77.0% of input) | 471 | 16 |
| 3 Thor_linker_TRIBE +cu −FBS | 21373906 (76.0% of input) | 588 | 18 |
| 4 Thor_linker_TRIBE +cu −FBS +Rapamycin | 15897789 (80.0% of input) | 614 | 26 |
| 5 pMT −cu +FBS | 15897789 | 514 | 11 |

TABLE 3

THOR TRIBE MRNA DATA

| pMT-thor-linker-E488Q | | 1st Mapped reads | reads >20, >20% Edited sites | 2nd Mapped reads | Edited sites | avg edited sites |
|---|---|---|---|---|---|---|
| GFP only | Induced | 16175589 (88.7% of input) | 18 | | | 18 |
| pMT-thor-linker-E488Q | Uninduced | 14945919 (87.8% of input) | 17 | 13890567 (93.1% of input) | | 17 |
| | Induced | 14072457 (80.7% of input) | 373 | 17864090 (91.0% of input) | 1427 | 900 |
| | Induced, Serum starvation | 18714759 (88.3% of input) | 877 | 24724653 (90.4% of input) | 3191 | 2034 |
| | Induced, Serum starvation, Rapamycin | 20420937 (85.9% of input) | 1745 | 30906558 (89.3% of input) | 4406 | 3075.5 |
| ADAR hyper only | Induced | 24135561 (88.6% of input) | 144 | 7690514 (88.2% of input) | 16 | 80 |

TABLE 4-continued

TOP-LIKE MRNA SEQUENCES IN THOR TARGETS

| mRNA | Sequence |
| --- | --- |
| CG14629 | CCAGTTAGTGCGA |
| Ntf-2 | TCGACGTTGTTCCACCC |
| RpL7 | GG<u>TCTTTCTTTCCCTTTCTTTT</u>ACCAG |
| RpL35 | TT<u>CCTTTTCTTTT</u>CGCCGCGTTTCCGGAGAGGT |
| Src42A | AG<u>TCTTTT</u>GGTATTTCTCGAGTCC |
| CoVIb | CGCTATAGCTATCGCCAGGCTCGT |

Gene Ontology (GO) analysis of the common targets of 4E-BP of 4E-BP in rapamycin and torin 1 treatment conditions indicated that 4E-BP is enriched in a translation related pathway. Examples of genes of interest identified by GO term analysis are as depicted in FIG. 16.

Example 8: Tribe Identification of Translating RNAS

Poly(A)-binding polypeptide (PABP) and Ribosomal Protein S2 (RPS2) are important components of the cellular machinery that enables protein synthesis. The TRIBE method was utilized in conjunction with PABP and RPS2 to form fusion polypeptides operatively linked to the catalytic subunit of an ADAR, as described above, to edit and identify translating mRNAs.

PABP is an RNA-binding polypeptide which binds to the poly(A) tail located on the 3' end of mRNA. PABP is also involved in mRNA precursors by helping Polyadenylate polymerase add the Poly(A) nucleotide tail to the pre-mRNA before translation. PABP is also present during stages of mRNA metabolism including Nonsense-mediated decay and nucleocytoplasmic trafficking. PABP may also protect the poly(A)tail from degradation and regulate mRNA production. PABP binding is designed to edit and identify polyadenylated mRNAs engaged in translation.

RPS2 is a component of the 40S subunit of the ribosome. During translation the 40S subunit binds to 70S subunits to form the ribosomal machinery responsible for the translation of mRNAs to form polypeptides. Together the 40S and 70S ribosomal subunits assemble on a strand of mRNA, where additional cellular components such as tRNAs are recruited for translation. RPS2 binding is designed to edit and identify mRNAs engaged in translation.

PABP-E488Q and RPS2-E488Q TRIBE fusion polypeptides were generated and assayed in a similar manner as described above. The PABP-E488Q fusion polypeptide produced a robust response in the induced group, which increased the amount of edited sites (FIG. 15H, left panel). The RPS2-E488Q fusion polypeptide was effective at increasing the amount of edited sites in the induced group (FIG. 15H, right panel). Relative to the RPS2-E488Q fusion protein, the PABP-E488Q TRIBE fusion polypeptide produced a greater increase in the number of edited sites.

TRIBE was developed to allow the identification of RBP targets in small numbers of specific cells in vivo. To show that TRIBE is applicable to different types of RBPs, it was applied to three *Drosophila* RBPs (Hrp48, dFMR1 and NonA). The fusion polypeptides maintain catalytic activity, and expression of all three TRIBE fusion polypeptides results in robust and reproducible introduction of new editing sites. The three REP-fusions have dramatically different editing patterns, indicating that the RBPs play a major role in determining editing specificity. Hrp48-TRIBE editing sites are enriched in the 30 UTR, as is the CLIP signal of both the fusion and endogenous proteins, demonstrating that TRIBE editing correctly reflects the endogenous binding pattern of Hrp48. dFMR1-TRIBE editing sites are dispersed throughout the coding sequence of transcripts, which is the observed binding pattern of mammalian FMRP as reported by Darnell et al. and is consistent with its role as a translation regulator. The third RPB fusion protein, NonA-TRIBE, edits RNA preferentially in introns, consistent with its published role as a splicing factor (Kozlova et al., Exp. Cell Res. 2006, 312, 2619-2630; Kaneko et al., Genes Dev. 2007, 21, 1779-1789).

Negative controls (the truncated ADAR catalytic domain alone and Hrp48-TRIBE with mutagenized RNA-binding domains) do not result in any additional editing sites, further indicating that editing is specified by the RBP. The data confidently indicates that the TRIBE editing sites faithfully mark transcript targets of the RBPs. Additional experiments expressing Hrp48-TRIBE and dFMR1-TRIBE in specific neurons demonstrate the ability to identify cell-specific RBP targets. Comparing these targets between neuronal subtypes illustrates the diversity of cell-type-specific RBP targets and therefore the importance of a method for defining REP-target interactions in individual cell types.

Comparison of Tribe to Clip

The current standard for the identification of RBP targets is CLIP and variants thereof Although most TRIBE sites are within 500 bp of a CLIP site, CLIP is important for determining precise RBP binding position. Nonetheless, the absence of alternative high-resolution methods for measuring in vivo binding has made it difficult to critically assess CLIP data for systematic biases or sources of false positives and false negatives.

CLIP false positives are a particular concern as transcripts that are functionally unaffected by knockdown of the RBP are often identified as targets (Lambert et al., Mol. Cell, 2014, 54, 887-900). Biases include the preferential cross-linking of uridines; the choice of RNase and fragmentation conditions, all of which have a significant impact on the detected targets. Most importantly perhaps, the low efficiency steps of the CLIP protocol necessitate large numbers of cells and as such is not amenable to the study of discrete, small numbers of cells.

Many of these drawbacks are avoided by TRIBE. It is not a biochemical technique and does not require an antibody. Alternatively, "RNA tagging" is a method to identify a target RNA by using a RBP fused to a *Caenorhabditis elegans* poly (U) polymerase, to tag target RNAs by attaching poly U tails bound by the RBP, which are used to identify the identity of the bound not (Lapointe et al., Nat. Methods 12, 1163-1170) Although it is too soon to compare the two methods, RNA tagging fundamentally differs from TRIBE since RNA tagging does not identify the region of the mRNA bound by the RBP, and target identification requires a special library protocol. Furthermore, in contrast to RNA tagging, the method of the present invention uses standard library methods and therefore needs very little RNA Indeed, TRIBE has been used to identify RBP targets in tiny numbers of specific neurons from the fly brain. The smallest group of neurons used in this study is the key circadian pacemaker neurons, the pdf cells, of which there are 16 in a single fly brain. The minimum number of cells required to generate TRIBE sequencing libraries is –150 neurons. Given recent advances and the trajectory of developments in RNA sequencing (RNA-Seq), TRIBE could be applicable to individual cells and provide an unprecedented level of resolution on RBP targets.

TRIBE involves sequencing the transcriptome of specific cells and therefore also captures their specific gene expression features, e.g., alternative splicing and 30 UTR patterns, and therefore it may be possible to correlate transcriptional, post-transcriptional and RBP binding events. However, the expression of the TRIBE fusion polypeptide may affect gene expression, transient expression and gene expression analysis of a parallel sample without TRIBE expression are advisable. In contrast, CLIP is typically done from mixed tissue, making it difficult to correlate the binding data with a specific gene expression state. For example, if CLIP is performed on brain in which the RBP is not ubiquitously expressed (e.g., FMRP is expressed in neurons but not glia or blood vessels), the corresponding transcriptome, expression levels as well as isoform features, are an average of all cell types. This also makes normalization difficult if not impossible, as noted by Darnell et al. As a result, CLIP targets are biased toward highly-expressed and long genes. Although TRIBE requires a minimum expression level of target, above that threshold there is no bias toward highly expressed genes.

Although optimization of CLIP can be challenging (e.g., the optimal crosslinking parameters differ between proteins, over-digestion of crosslinked complexes by RNase can affect the results), TRIBE is comparatively simple to perform and should also be amenable to mammalian systems. It only requires cloning and expression, the RNA is then purified and sequenced, and novel editing events detected via a bioinformatics pipeline.

Potential Shortcomings of Tribe

Figure 14A:
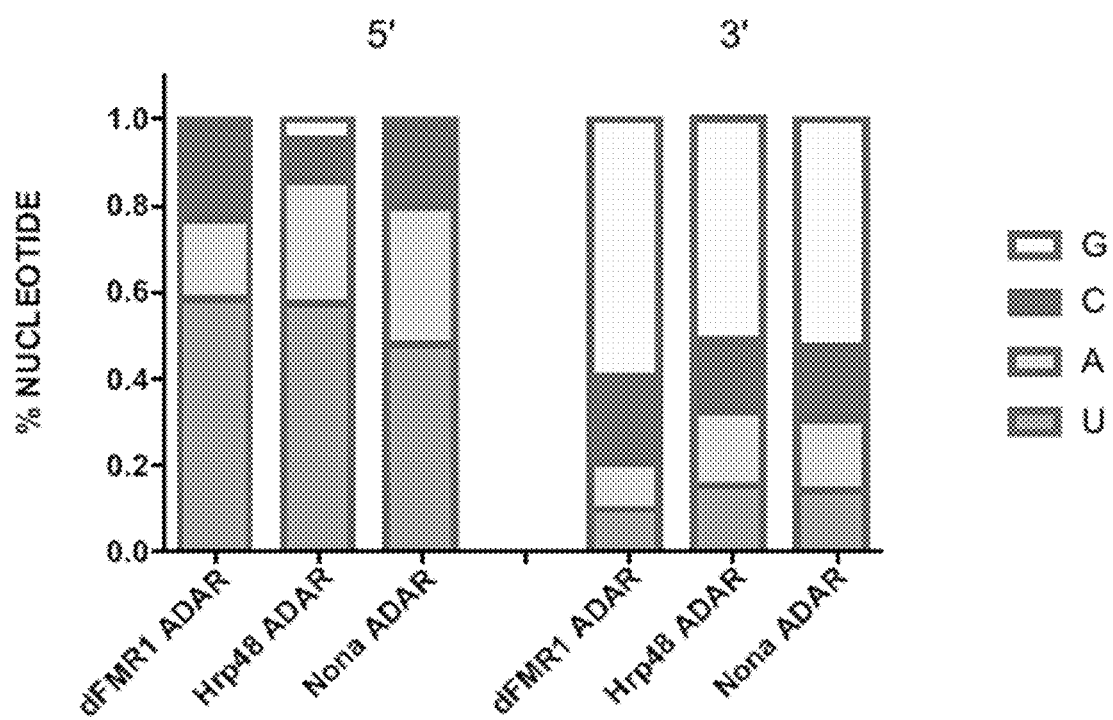
FIGS. 14A-14B show data indicating the nearest-neighbor preference of nucleotide identity proximal to editing sites.
Figure 14B:
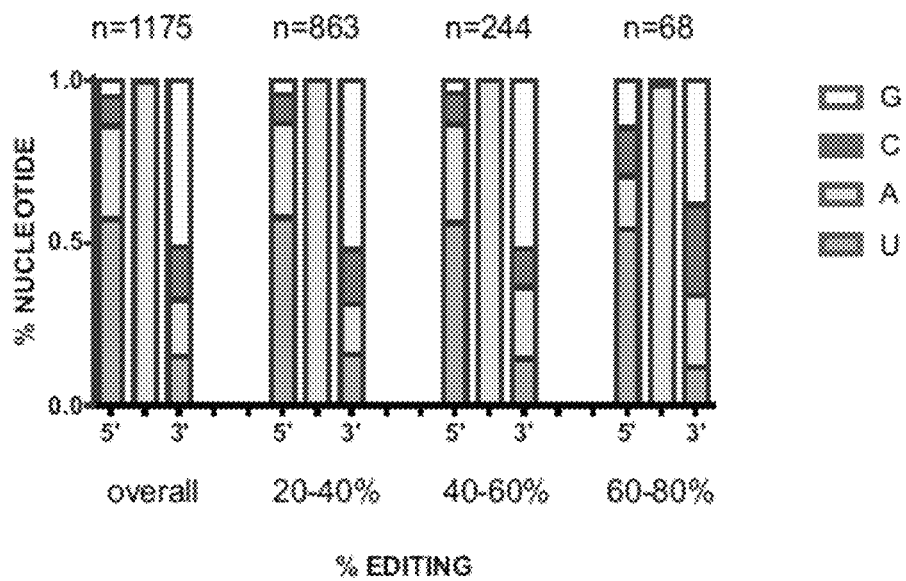
Figure 14C:
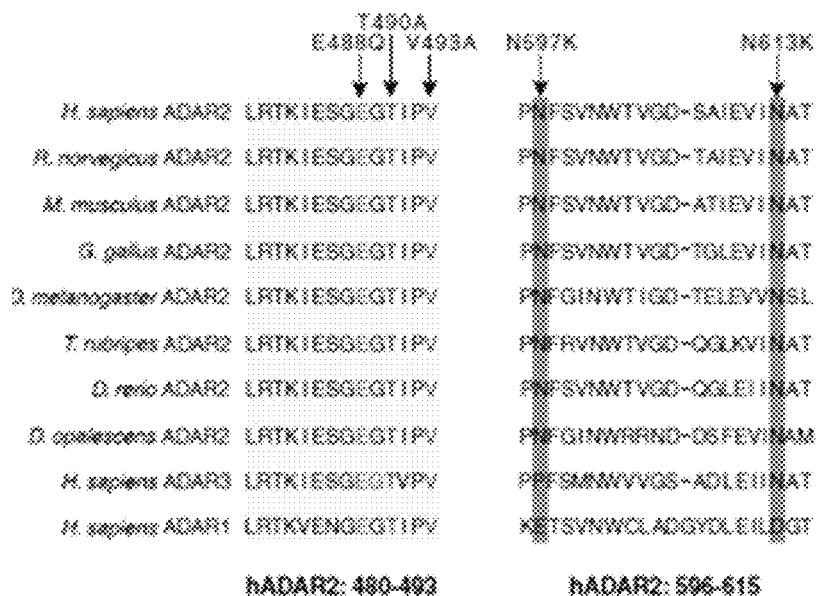
FIG. 14C provides a schematic showing the amino acid sequence alignment of hADAR2 catalytic domains between amino acids 480-493 (left panel; SEQ ID NOs: 38-47 in order of appearance) and 596-615 (right panel; SEQ ID NOs; 48-57, in order of appearance). Mutations in the catalytic domains are indicated by black arrows.

A risk of hijacking the function of ADAR is that some of its own editing selectivity may remain. Obviously the ADARcd-TRIBE protein has an absolute requirement for an editable substrate (an adenosine) proximal to the RBP binding site, the absence of which may preclude the editing of some targets and result in false negatives. In addition, endogenous ADARs have preferences for bases proximal to the editing site and all TRIBE proteins maintain these published preferences (e.g., 50 U enriched, 30 G enriched; FIG. 14) (Eggington et al., Nat Commun., 2011, 2,319; Kuttan and Bass, Proc. Natl. Acad. Sci., 2012, 109, E3295-E3304.; Porath et al., Nat Commun., 2014, 5, 4726). This data indicates that the editing specificity is at least partially dictated by the deaminase domain.

However, the most prominent cause of false negatives is probably the strong preference of the ADAR catalytic domain for double-stranded RNA even without its dsRBDs (Macbeth et al., Science. 2005, 309, 1534-1539; Eggington et al.; Montiel-Gonzalez et al., Proc. Natl. Acad. Sci. 2013, 110, 18285-18290; Vogel et al., Chem Int Ed. Engl. 2014, 53, 6267-6271; Vogel and Stafforst Chem Med Chem 2014, 9, 2021-2025; Phelps et al., Nucleic Acids Res. 2015, 43, 1123-1132) Although endogenous ADAR exhibits considerable plasticity, e.g., it edits regions of highly complex structure as well long stretches of duplex RNA, it was assumed that RBP-ADARcd proteins will not label their bound targets if they are composed exclusively of single stranded RNA Indeed, the comparison of edited regions with those CLIP targets that have no editing (FIG. 6) indicates that the requirement for a bulged A within a dsRNA region (Eifler et al., 2013) explains why TRIBE has fewer targets than CLIP.

Yet the data indicates that 40%-50% of target mRNAs have sufficient double-stranded character near the RBP binding site to be edited by the TRIBE ADARcd (FIGS. 4D and 6). The data therefore indicates that tethering of the ADARcd to its targets by an RBP can take advantage of dynamic structure formation in vivo (Mortimer et al., Nat Rev. Genet 2014, 15, 469-479; Kwok et al., Trends Biochem Sci. 2015, 40, 221-232), especially over a time frame of hours, to edit and permanently mark many substrates at a detectable frequency. Indeed, if the TRIBE ADARcd can take advantage of double-stranded RNA features that are dynamic, TRIBE favors the labeling of long-lived interactions between the RBP and its target RNA CLIP by contrast may take a snapshot that includes many weaker and transient inter-actions that are false positives. Although this interpretation explains the much larger number of CLIP targets for Hrp48, TRIBE targets have much better overlap with the best CLIP targets, indicating that a high fraction of them also reflect more stable and therefore meaningful in vivo interactions.

Improvements and Extensions

The study presented herein is the first demonstration of TRIBE. Possible modifications may be made. For example, an additional editing moiety may be used. Experiments were conducted in an effort to perform TRIBE using cytidine deaminases, which edit single-stranded RNA and catalyze the conversion of cytidine and uridine. Seven characterized and putative cytidine deaminases were tried and the mouse APOBEC1 ADAR was selected. In one embodiment, a characterized ADAR mutant having enhanced catalytic activity and having less of a nearest-neighbor preference than wild-type ADAR (Kuttan and Bass, 2012) may be used. In another embodiment, an endogenous locus knockin may be used to achieve endogenous levels of REP-TRIBE expression. In another embodiment, TRIBE can be extended by fusing the ADARcd to other proteins and expressing them in a cell-type-specific manner, for example, polyA binding polypeptide for transcriptome identification or ribosomes for translational profiling, all of which can be done without any biochemistry. In another embodiment, a light-, biochemical- or chemical-activatable domain to provided spatial and temporal control to TRIBE editing may be used.

Cell Specificity

Experiments expressing Hrp48-TRIBE and dFMR1-TRIBE in specific subsets of neurons identified cell-specific targets. Comparing them between neuronal subtypes illustrates the diversity of cell-type-specific RBP targets and thus the importance of TRIBE for defining REP-target interactions in particular cell types. Although recent advances in sequencing technology have revealed the distinct regulation of individual cell types at the transcriptional and post-transcriptional level, it has been extremely difficult to define the cell-type-specific roles and targets of individual RBPs. TRIBE ameliorates this issue and should therefore contribute to addressing the long-standing question of how more broadly expressed proteins have cell-specific effects. This issue is particularly relevant to several RNA-binding proteins associated with human diseases, e.g., FMRP, FUS, and TDP43.

The results described herein above, were obtained using the following methods and materials.

Molecular Biology

The RBP of interest was cloned upstream of the *Drosophila* ADAR catalytic domain (the whole C terminus downstream of the second dsRBD was used, starting with Y268 to terminal E669 of AHN59262.1) with minimal linker region into a pMT-A vector (Invitrogen, V4120-20, also harboring a blasticidin-resistance gene). Stable S2 cell lines were made by transfecting with the pMT-RBP-ADARcd- VS-Blasticidin plasmid, followed by subsequent blasticidin-resistance selection. Fusion polypeptide expression was induced by introduction of copper sulfate for 24 hr, prior to harvesting protein and RNA. S2 cell expression of all fusion polypeptides was assayed by western blot for the VS tag (Invitrogen, 46-1157). Nascent RNA was extracted from S2 cells, in accordance with Khodor et al., and depleted of ribosomal RNA, in accordance with Pennington et al. (Proc. Natl. Acad. Sci. 2013, 110, 7678-7683), and mRNA (two rounds of pA depletion using Invitrogen Dynabeads® Oligo dT, in accordance with the manufacturer's protocol).

Fluorescently labeled neurons were isolated from dissected, triturated fly brains by manual sorting using a glass micro-pipette, as described in Abruzzi et al. (Methods Enzymol. 2015, 551, 369-386) RNA-Seq libraries from S2 cells were constructed using the standard Illumina® Truseq™ Kit protocol. RNA-Seq libraries from manually sorted neurons were made as described in Abruzzi et al.

RNA-Editing Analysis

RNA-editing events are defined as loci where there are A >80% and zero G in genomic DNA and G >0% in RNA (in the reverse strand, the reverse complement was evaluated). Genomic DNA was also sequenced from either S2 cells or yw flies, to provide a reference which contains SNPs. Analysis of RNA-Seq data was performed as previously published (Rodriguez et al., Mol. Cell 2012, 47, 27-37), with some modifications, described in detail below.

In neurons, removal of endogenous editing events from the analysis was required. A lower threshold (ten reads, 10% editing) was used to define endogenous editing events. All endogenous events identified, including sites from all non-TRIBE expressing negative controls in all lines used in a given experiment were removed from the data from TRIBE-expressing neurons. Gene ontology (GO) analysis was performed using DAVID (Huang da et al, Nat. Protoc. 2009, 4, 44-57).

Clip

CLIP libraries of Hrp48 and Hrp48-ADARcd were constructed as described in Cho et al. (Cell. 2012, 151:765-777), with some modifications as described below. Significant regions of binding were determined using the CLIPper algorithm (Lovci et al., Nat. Struct. Mol. Biol. 2013, 20, 1434-1442) and as described in Moore et al., Nat. Protoc. 2014, 9, 263-293.

Fly Lines

TRIBE flies were generated by cloning the RBP-ADARcd-V5 transgene into a modified pJFRC7-20×UAS construct (RBP in locus of removed mCD8-GFP, Addgene #26220), which was injected by BestGene. UAS-RBP-ADARcd-V5; UAS-eGFP flies (Bloomington stock center #1522) were crossed to a range of driver lines (pdf-Gal4, TH-Gal4, elav-gsg-Gal4, Cha-Gal4, and GAD-Gal4) to achieve cell-type-specific expression of the fusion polypeptide. Constitutive pan-neuronal expression of Hrp48-TR1BE (elav-Gal4 and UAS-Hrp48-ADARcd) was lethal, so adult-specific expression was achieved using the gene-switch system (Osterwalder et al, Proc. Natl. Acad. Sci. 2001, 98, 12596-12601), elav-gsg-Gal4. Young flies (3 days old) were maintained on food containing RU486 (0.2 mg/ml, Sigma #8046) for 5-8 days prior to dissection and cell sorting. Additional details are described below.

Cloning

TRIBE component cDNA clones were acquired from various sources; Hrp48 (P48809) from Donald Rio; dFMR1 (AF305881) provided by Tom Jongens, dADAR provided by Robert Reenan (Palladino et al., 2000), NonA (clone RE58280, *Drosophila* Genomics Resource Centre, Bloomington, IN). Cytidine deaminases assayed were mouse APOBEC1 (BC003792), yeast CDD1 (Gene ID 850946), putative *Drosophila* cytidine deaminases CG5292 (FBgn0038491) and CG6951 (FBgn0036959), human APOBEC3A (Sharma et al., 2015) and plant QED1 and RARE1, (Wagoner et al., 2015). Mutations of the two RNA recognition motifs ofHrp48 (P48809, F50V, F52V and F139V, F141V) were modeled after mutations performed by Mayeda et al. (1994) on hnRNP A1.

Cell Sorting

A detailed description of the cell sorting and RNA-Seq library generation protocol is provided in Abruzzi et al. Briefly, between 20 and 50 fly brains were dissected in the presence of tetrodotoxin only (0.1 uM), digested in L-cysteine-activated papain (Worthington) for 20 minutes, before manual dissociation using fire-polished pipette tips. Dissociated cells are allowed to settle in a large volume of sorting medium on Sylgard coated plates. Using a dissecting microscope fluorescently labeled neurons are then manually aspirated using micropipettes pulled from capillary tubes (World Precision Glass Capillaries #1B100-4, Sutter Instrument Company). Three rounds of sorting are performed until approximately 150-400 fluorescent cells are sorted into 50 ul of Lysis/Binding buffer (Invitrogen; Dynabeads® mRNA direct kit) and frozen at −80° C.

Generation of Sequencing Libraries from Manually Sorted Neurons

Generation of sequencing libraries was performed as is described in Abruzzi et al. It is estimated between 200-500 pg of total or ~5 pg of mRNA is gathered from ~100 manually sorted neurons. mRNA is isolated on poly dT beads (Dynabeads® mRNA direct kit; Invitrogen) using a scaled down version of the manufacturer's protocol, and concentrated by vacuum centrifugation (SpeedVac RC1010, Jouan, Winchester, VA). A modified linear amplification method is then used to amplify this RNA; reverse transcription using random hexamers and dT primers containing T7 promoters generates a cDNA template that is used for one round of in vitro transcription (MEGAscript™ kit, Ambion). The cRNA is isolated (RNA MinElute® column, Qiagen), concentrated by vacuum centrifugation, and used as input for the RNA Tm-Seq library generation kit (Illumina®). Resulting libraries are somewhat 3' biased and approximately 20-60% of reads map to the fly genome (as discussed in Abruzzi et al.). All sequencing was performed on either an Illumina® HiSeq or MiSeq.

Analysis of Sequencing Data for RNA Editing

Analysis of RNA sequencing data was performed as previously published Rodriguez et al., with some modifications. All raw sequencing data and identified RNA editing sites are available for download from NCBI Gene Expression Omnibus (www.ncbi.nlm.nih.gov/geo/), accession number (GSE78065). (Except yw gDNA which is in Series GSE37232, sample GSM914095).

In brief, sequencing reads are trimmed with Trimmomatics (Bolger et al., Bioinformatics, 2014, 30:2114-2120) by 6 bp at each end, additional low quality bases from either end are removed and reads with average quality score of 30 or greater are kept. Genomic DNA reads are aligned using bowtie2 (parameters: —sensitive) to the reference genome (Release 5/dm3) and RNA sequencing reads are aligned using tophat2 (Trapnell et al., Bioinformatics. 2009, 25:1105-1111.) (parameters: -m 1 -p 5-g 2-I 50000—microexon-search—no-coverage-search).

PCR duplicates were not removed for editing analysis. Following re-analysis of a select number of data sets there was only a small change in the number or identity of editing sites and essentially no change in the overlap with CLIP data. The gtf file used throughout the analysis was downloaded from iGenomes (via Illumina, dm3 build). The editing analysis pipeline used RefSeq annotation of genes, which were downloaded from UCSC genome browser. Only uniquely mapped reads are considered for editing analysis. As number of editing events detected will change with sequencing depth, within each experiment each sample was sequenced to roughly the same depth. Initial experiments with Hrp48 TRIBE in S2 cells are an exception, experimental samples were sequenced to ~200 million reads to determine if many events were not being detected with less coverage. 70-90 edit sites were detected in wild type cells and cells expressing the dADARcd alone, and on GEO (these likely represent SNPs, PCR errors, endogenous editing sites and may include sites edited by the dADARcd alone).

Only events with minimum 20 reads and 10% editing were considered to be an editing events, gDNA coverage and uniformity of nucleotide identity were also required to avoid inclusion of single nucleotide polymorphisms. RNA editing data is converted to bedgraph file format for display, where the editing percentage (#edit bases/ #total bases) is the height of the displayed black bar. RNA editing data is manipulated as bed/bedgraph format using bedtools.

Hits-CLIP

The CLIP libraries of Hrp48 were constructed as described previously with slight modification (Cho et al.). S2 cells or head powder of CS flies were irradiated twice for 300 mJ/cm2 at 254 nm (CL-1600 Ultraviolet crosslinker). For RNaseA treatment, 401.11 of 40 ng/ml RNaseA was added to 1 ml of lysate. For Immunoprecipitation of Hrp48, Dynabead® protein A (Invitrogen) and rabbit anti-Hrp48 antibody (a gift from Donald Rio, (Hammond et al., Molecular and cellular biology. 1997, 17:7260-7267) were used. For Immunoprecipitation of Hrp48-ADAR-V5, Dynabeads® protein A (Invitrogen), rabbit anti-mouse IgG antibody (Millipore, 06-371) and mouse monoclonal anti-V5 antibody (Invitrogen, 46-1157) were used. Following linkers and primers were used for making libraries. 3' linker (RA3), /5rApp/ TGGAATTCTCGGGTGCCAAGG/3ddC/; 5' linker (RA5-N4), rGrUrUrCrArGrArGrUrUrCrUrArCrArGrUrCrCrGrArCrGrArUrCrNrNrNrN; RNA RT Primer (RTP), GCCTTGGCACCCGAGAATTCCA; RNA PCR Primer (RP1, forward primer), AATGATACGGCGAC-CACCGAGATCTACACGTTCAGAGTTCTA-CAGTCCGA; RNA PCR Primer-Index 7 (RPI7, reverse primer), CAAGCAGAAGACGGCATACGAGAT-GATCTGGTGACTGGAGTTCCTTGGCACCCG AG AATTCCA; RNA PCR Primer-Index 8 (RPI8, reverse primer), CAAGCAGAAGACGGCATACGAGATT-CAAGTGTGACTGGAGTTCCTTGGCACCCG AG AAT-TCCA; RNA PCR Primer-Index 9 (RPI9, reverse primer), CAAGCAGAAGACGGCATACGAGATCT-GATCGTGACTGGAGTTCCTTGGCACCCG AGAAT-TCCA.

CLIP, Motif Analysis and Gene Ontology

CLIP sequence reads were aligned using Novoalign, (novoalign-t 85-1 23 -s 1 -r None). Subsequent bioinformatic analysis of CLIP data was performed as described in Moore et al. (2014) and using the CLIPper algorithm (available at github.com/YeoLab/clipper) with default settings. To calculate a per gene CLIP enrichment value, the peak heights of each CLIP region were locally normalized to the mRNA-Seq reads extracted for that region, and summed these values across each gene (using CLIPper peaks). Motif analysis using MEME was conducted (Bailey et al., Nucleic acids research. 2009, 37:W202-208), version 4.10.0) (parameters: meme-minw 6-maxw 10-maxsize 1000000-dna-nmotifs 5-mod zoops) around significant CLIP sites as defined by the Darnell pipeline (Moore et al., 2014). MEME analysis for TRIBE data was performed by inputting the region around the editing site. Gene ontology analyses were performed using DAVID (Huang da et al.), TRIBE target genes (in FBgn format) were analyzed against a background of all genes expressed in the fly brain (>2 fpkm, ~8000 genes). Gene expression levels were quantified using Cufflinks2.

RNA Structure Analysis

RNA structure folding with UNAFOLD was carried out on flanking sequences near TRIBE editing sites and CLIP binding sites identified by CIMS analysis (Cross Linking induced Mutation Site) that lack editing by TRIBE. A flanking region of 250nt both 5' and 3' of the site (501nt in total) was folded with UNAFold parameters (hybrid-ss-min—suffix DAT mfold=5,8,200—noisolate), base pairing was counted in the predicted minimum free energy (MFE) and predicted suboptimal structures within L1L1G=5Kcal/mol of the MFE [1] for each site and five nucleotides on either side of the sites to create a profile of double strandedness. All profiles for each site are averaged to create a plot (mean+/−SEM, n=17 TRIBE editing sites) for the TRIBE sites and CIMS CLIP sites.

Notes on Analysis of RNA Editing Data

All analysis of TRIBE data performed here are binary; either a gene has a TRIBE editing site or not, e.g., the mRNA is a target or not. Alternatively, two possible metrics to rank the 'strength' of RBP targets, the number of editing sites in a gene and the extent to which they are edited (editing percentage) could have been used. However, such metrics should be interpreted with caution. First, longer genes obviously have more capacity for harboring more editing sites. Second, editing percentage may be affected by the propensity of the target region to participate in double stranded structures (discussed above) as well as by the strength of interaction between an RBP and its target.

The number of sites caused by a particular RBP-TRIBE protein will presumably vary quite widely so it is difficult to recommend a specific sequencing depth. Factors that could affect the number of editing events include the strength of binding of the endogenous RBP, the strength of binding of the TRIBE-RBP, the structure preference of the RBP, the expression level of the TRIBE-RBP, in addition sequencing depth effects the number of sites detected. The deeper the sequencing depth the more editing sites will be detected. For the experiments the deepest sequencing is ~200 million mapped reads (Hrp48-TRIBE, s2 cells), however, in the data indicates 20-30 million mapped reads can be sufficient (FIG. 10). It is recommended that within an experiment each sample is sequenced to roughly the same depth.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

The invention claimed is:

1. A fusion polypeptide comprising an RNA binding polypeptide or an active RNA binding fragment thereof operably linked to a catalytic domain of an RNA-editing enzyme, wherein the fusion polypeptide is active for binding and editing RNA wherein the catalytic domain of an RNA-editing enzyme is Adenosine Deaminase Acting on RNA 2 (ADAR2) of SEQ ID NO: 4 with a E488Q, a V493A, and/or a T490A mutation.

2. The fusion polypeptide of claim 1, wherein the fusion polypeptide further comprises a poly(A)-binding polypeptide (PABP) which binds to the poly(A) tail located on the 3' end of mRNA, or a Ribosomal Protein S2 (RPS2) operably linked to the fusion polypeptide.

3. The fusion polypeptide of claim 1, wherein the RNA binding polypeptide is selected from the group consisting of Zipcode binding polypeptide 1 (ZBP1), Fus, Tdp43, EIF4EBP1, and HuR.

* * * * *